(12) United States Patent
Jiang et al.

(10) Patent No.: US 10,463,768 B2
(45) Date of Patent: Nov. 5, 2019

(54) COMPOSITE MATERIAL FOR TISSUE RESTORATION

(71) Applicant: The Johns Hopkins University, Baltimore, MD (US)

(72) Inventors: Xuesong Jiang, Baltimore, MD (US); Sashank Reddy, Baltimore, MD (US); Gerald Brandacher, Baltimore, MD (US); Hai-Quan Mao, Baltimore, MD (US); Justin Sacks, Baltimore, MD (US); Xiaowei Li, Henrico, VA (US); Kevin Feng, Baltimore, MD (US); Russell Martin, Baltimore, MD (US); Georgia C. Yalanis, Milcreek, UT (US); Ji Suk Choi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/432,606

(22) Filed: Feb. 14, 2017

(65) Prior Publication Data

US 2018/0050130 A1 Feb. 22, 2018

Related U.S. Application Data

(63) Continuation of application No. PCT/US2015/045494, filed on Aug. 17, 2015.

(60) Provisional application No. 62/038,030, filed on Aug. 15, 2014.

(51) Int. Cl.
| | |
|---|---|
| *A61L 27/52* | (2006.01) |
| *A61L 27/16* | (2006.01) |
| *A61L 27/36* | (2006.01) |
| *A61L 27/18* | (2006.01) |
| *A61L 27/56* | (2006.01) |
| *A61L 27/24* | (2006.01) |
| *A61L 27/58* | (2006.01) |
| *A61L 27/48* | (2006.01) |

(52) U.S. Cl.
CPC .............. *A61L 27/52* (2013.01); *A61L 27/16* (2013.01); *A61L 27/18* (2013.01); *A61L 27/24* (2013.01); *A61L 27/3633* (2013.01); *A61L 27/56* (2013.01); *A61L 27/58* (2013.01); *A61L 27/48* (2013.01); *A61L 2400/06* (2013.01); *A61L 2430/06* (2013.01); *A61L 2430/34* (2013.01)

(58) Field of Classification Search
None
See application file for complete search history.

(56) References Cited

U.S. PATENT DOCUMENTS

| | | |
|---|---|---|
| 1,683,347 A | 9/1928 | Eastman |
| 1,698,049 A | 1/1929 | Eastman |
| 1,880,560 A | 10/1932 | Eastman |
| 1,880,808 A | 10/1932 | Eastman |
| 1,984,147 A | 12/1934 | Eastman |
| 2,129,052 A | 9/1938 | Eastman |
| 3,475,407 A | 10/1969 | Upjohn |
| 3,509,127 A | 4/1970 | Upjohn |
| 3,513,155 A | 5/1970 | Upjohn |
| 3,544,551 A | 12/1970 | Upjohn |
| 3,617,201 A | 11/1971 | Berni et al. |
| 3,989,816 A | 11/1976 | Rajadhyaksha |
| 4,043,331 A | 8/1977 | Martin et al. |
| 4,316,893 A | 2/1982 | Rajadhyaksha |
| 4,405,616 A | 9/1983 | Rajadhyaksha |
| 4,557,934 A | 12/1985 | Cooper |
| 4,568,343 A | 2/1986 | Leeper et al. |
| 4,783,450 A | 11/1988 | Fawzi et al. |
| 4,973,493 A | 11/1990 | Guire |
| 5,258,041 A | 11/1993 | Guire et al. |
| 5,522,879 A | 6/1996 | Scopelianos |
| 5,563,056 A | 10/1996 | Swan et al. |
| 5,637,480 A | 6/1997 | Swan et al. |
| 5,846,558 A | 12/1998 | Nielsen et al. |
| 6,278,018 B1 | 8/2001 | Swan |
| 6,488,872 B1 | 12/2002 | Beebe et al. |
| 2004/0197367 A1 | 10/2004 | Rezania et al. |
| 2007/0202074 A1* | 8/2007 | Shalaby ............... A61K 31/74 424/78.27 |
| 2011/0288199 A1* | 11/2011 | Lowman ............... A61F 2/3872 523/114 |

(Continued)

FOREIGN PATENT DOCUMENTS

| | | |
|---|---|---|
| GB | 2082665 A | 3/1982 |
| WO | 199832675 A2 | 7/1998 |

(Continued)

OTHER PUBLICATIONS

T. G. Kim et al., "Biomimetic Scaffolds for Tissue Engineering," Adv. Funct. Mater. 2012, 22, 2446-2468.*
Ekaputra et al., "The three-dimensional vascularization of growth factor-releasing hybrid scaffold of poly(epsilon-caprolactone)/collagen fibers and hyaluronic acid hydrogel". Biomaterials 32(32): 8108-8117, 2011. (Retrieved on Sep. 28, 2015). Retrieved from the internet<URL:http://www.sciencedirect.com/science/article/pii/S0142961211007939>.
International Search Report issued in corresponding International Application No. PCT/US2015/045494, dated Nov. 6, 2015, 1 page.

(Continued)

*Primary Examiner* — Monica A Shin
(74) *Attorney, Agent, or Firm* — Mintz Levin Cohn Ferris Glovsky and Popeo, P.C.; Peter F. Corless

(57) ABSTRACT

A composite material can include a gel and at least one nanostructure disposed within the gel. A method for healing a soft tissue defect can include applying a composite material to a soft tissue defect, wherein the composite material includes a gel and a nanostructure disposed within the gel. A method for manufacturing a composite material for use in healing soft tissue defects can include providing a gel and disposing nanofibers within the gel.

18 Claims, 29 Drawing Sheets

(56) References Cited

U.S. PATENT DOCUMENTS

| | | | |
|---|---|---|---|
| 2012/0040461 A1* | 2/2012 | Beachley | A61L 27/48 |
| | | | 435/396 |
| 2012/0264190 A1 | 10/2012 | Christman et al. | |
| 2014/0112990 A1* | 4/2014 | Bencherif | A61K 39/0011 |
| | | | 424/486 |
| 2015/0105863 A1* | 4/2015 | Zussman | A61L 27/52 |
| | | | 623/23.72 |

FOREIGN PATENT DOCUMENTS

| | | |
|---|---|---|
| WO | 2009/042829 A1 | 4/2009 |
| WO | 2013/071107 A1 | 5/2013 |
| WO | 2013/172788 A1 | 11/2013 |

OTHER PUBLICATIONS

Written Opinion of the International Searching Authority issued in corresponding International Application No. PCT/US2015/045494, dated Nov. 6, 2015, 1 page.

Chua, et al., Surface-aminated electrospun nanofibers enhance adhesion and expansion of human umbilical cord blood hematopoietic stem/progenitor cells. Biomaterials. 2006, 27, 6043-6051.

Coburn, et al. Biomimetics of the Extracellular Matrix: An Integrated Three-Dimensional Fiber-Hydrogel Composite for Cartilage Tissue Engineering. (2011) Smart Structures and Systems, 7(3), 213.

Ekaputra, et al. The three-dimensional vascularization of growth factor-releasing hybrid scaffold of poly ( 3-caprolactone)/collagen fibers and hyaluronic acid hydrogel. Biomaterials 32 (2011) 8108e8117.

Holloway, et al., Interfacial optimization of fiber-reinforced hydrogel composites for soft fibrous tissue applications. Acta Biomaterialia 2014, 10, 3581-3589.

Jiang, et al.,The effect of nanofibre surface amine density and conjugate structure on the adhesion and proliferation of human haematopoietic progenitor cells. Interface Focus 2011, 1, 725-733.

Kakagia, et al., Autologous Fat Grafting: In Search of the Optimal Technique. (2014) Surgical Innovation, 21(3), 327-336.

Katayama et al., Coil-reinforced hydrogel tubes promote nerve regeneration equivalent to that of nerve autografts. Biomaterials 2006, 27, 505-518.

Khetan, et al. Degradation-mediated cellular traction directs stem cell fate in covalently crosslinked three-dimensional hydrogels. (2013) Nature Materials, 12(5), 458-465.

Li, et al. Engineering In Situ Cross-Linkable and Neurocompatible Hydrogels. (2014) Journal of Neurotrauma, 31(16), 1431-1438.

Wu, et al. In vitro behaviors of hydroxyapatite reinforced polyvinyl alcohol hydrogel composite. (2008) Materials Chemistry and Physics 107.2 (2008): 364-369.

Xu, et al. Material properties and osteogenic differentiation of marrow stromal cells on fiber-reinforced laminated hydrogel nanocomposites. Acta Biomaterialia 2010, 6, 1992-2002.

Yin, et al., "High density of immobilized galactose ligand enhances hepatocyte attachment and function", Wiley Periodicals, Inc., 2002, pp. 1094-1104.

Young, et al., "Injectable hydrogel scaffold from decellularized human lipoaspirate", Acta Biomaterialia, 2011, vol. 7, pp. 1040-1049.

Yusong, et al., "Mechanical properties of nanohydroxyapatite reinforced poly (vinyl alcohol) gel composites as biomaterial", Journal of Materials Science, 2007, vol. 42, pp. 5129-5134.

Zhou, et al. A novel polyacrylamide nanocomposite hydrogel reinforced with natural chitosan nanofibers. (2011) Colloids and Surfaces B: Biointerfaces, 84(1), 155-162.

Shin, et al., "Engineered ECM-like microenvironment with fibrous particles for guiding 3D-encapsulated hMSC behaviours", Journal of Materials Chemistry B, 2015, vol. 3, pp. 2732-2741.

Slevin, et al., "Angiogenic Oligosaccharides of Hyaluronan Induce Multiple Signaling Pathways Affecting Vascular Endothelial Cell Mitogenic and Wound Healing Responses" The Journal of Biological Chemistry, vol. 277, No. 43, Oct. 25, 2002, pp. 41046-41059.

Sommer, et al., "Multiaxial mechanical properties and constitutive modeling of human adipose tissue: A basis for preoperative simulations in plastic and reconstructive surgery" Acta Biomaterialia, 2013, vol. 9, pp. 9036-9048.

Tate, et al., "Fibronectin Promotes Survival and Migration of Primary Neural Stem Cells Transplanted Into the Traumatically Injured Mouse Brain", Cell Transplantation, 2002, vol. 11, pp. 283-295.

Trochon, et al., "Evidence of involvement of CD44 in endothelial cell proliferation, migration and angiogenesis in vitro", International Journal of Cancer, 1996, vol. 66, pp. 664-668.

Varma, et al., "Injectable carboxymethylcellulose hydrogels for soft tissue filler applications", Acta Biomaterialia, 2014, vol. 10, pp. 4996-5004.

Whitesides, et al., "Soft Lithography", Angewandte Chemie International Edition, 1998, vol. 37, pp. 550-575.

Whitesides et al., "Flexible Methods for Michofluids", American Institute of Physics, Jun. 2001, 54(6), pp. 42-48.

Placone, et al., "Human astrocytes develop physiological morphology and remain quiescent in a novel 3D matrix", Biomaterials 2015, vol. 42, pp. 134-143.

Quake, S. R., et al., "From Micro—to Nanofabrication with Soft Materials" Science, Nov. 24, 2000, vol. 290, pp. 1536-1540.

Ren, et al., "Enhanced differentiation of human neural crest stem cells towards the Schwann cell lineage by aligned electrospun fiber matrix", Acta Biomaterialia, 2013, vol. 9, pp. 7727-7736.

Ryu, et al., "Catechol-Functionalized Chitosan/Pluronic Hydrogels for Tissue Adhesives and Hemostatic Materials", Biomacromolecules 2011, vol. 12, pp. 2653-2659.

Salibian, et al., "Stem Cells in Plastic Surgery: A Review of Current Clinical and Translational Applications" Archives of Plastic Surgery, Nov. 2013, vol. 40, No. 6, pp. 666-675.

Seliktar, "Designing Cell-Compatible Hydrogels for Biomedical Applications", Science, Jun. 1, 2012, vol. 336, pp. 1124-1128.

Alkhouli, et al. The mechanical properties of human adipose tissues and their relationships to the structure and composition of the extracellular matrix. (2013) American Journal of Physiology. Endocrinology and Metabolism, 305 (12), E1427-35.

Annabi, et al., Controlling the PorosityPorosityand Microarchitecture of Hydrogels for Tissue Engineering. Tissue Engineering: Part B vol. 16, No. 4, 2010.

Becker, H., et al. "Polymer microfluidic devices." Talanta, 56(2):267-287, 2002.

Beebe, et al., Functional hydrogel structures for autonomous flow control inside microfluidic channels. Nature; 404:588-59 (2000).

Bosworth, et al., State of the art composites comprising electrospun fibres coupled with hydrogels: a review. Nanomedicine: Nanotechnology, Biology, and Medicine 9 (2013) 322-335.

Choi, et al., Pluronic/chitosan hydrogels containing epidermal growth factor with wound-adhesive and photo-crosslinkable properties. Journal of Biomedical Materials Research Part A 2010, 95 (2), 564-573.

Christopherson, et al., The influence of fiber diameter of electrospun substrates on neural stem cell differentiation and proliferation. Biomaterials 30 (2009) 556-564.

Chua, et al., Stable immobilization of rat hepatocyte spheroids on galactosylated nanofiber scaffold. Biomaterials 2005, 26, 2537-2547.

Tsoi, et al., Safety of Tissue Expander/Implant versus Autologous Abdominal Tissue Breast Reconstruction in Postmastectomy Breast Cancer Patients: A Systematic Review and Meta-Analysis. 2014. Plastic and Reconstructive Surgery, 133(2), 234-249.

Patel, et al. Management of Massive Mastectomy Skin Flap Necrosis Following Autologous Breast Reconstruction. (2012) Annals of Plastic Surgery, 69(2), 139-144.

Calobrace, et al. 2014 The Biology and Evolution of Cohesive Gel and Shaped Implants Plastic and Reconstructive Surgery, 134(1 Suppl), 6S-11.

Lim, et al. "Electrospun scaffolds for stem cell engineering" . Advanced Drug Deliver Reviews, 2009, vol. 61, pp. 1084-1096.

(56) References Cited

OTHER PUBLICATIONS

Lim, et al., "The effect of nanofiber-guided cell alignment on the preferential differentiation of neural stem cells", Biomaterials, 2010, vol. 31. pp. 9031-9039.
Lotempio, et al. Breast Reconstruction with SGAP and IGAP Flaps. (2010) Plastic and Reconstructive Surgery, 126 (2), 393-401.
Freeman, et al., "Evaluation of a hydrogel-fiber composite for ACL tissue engineering" Journal of Biomechanics, 2011, vol. 44, pp. 694-699.
European Search Report and European Search Opinion issued in corresponding EP 15831684.4 with EP Claims, dated Jan. 25, 2018, 10 pages.
X. Li et al., "Nanofiber-hyrogel composite-mediated angiogenesis for soft tissue reconstruction", Science Translation Medicine, vol. 11, pp. 1-11 (2019).
European Examination Report dated Jan. 10, 2019, in corresponding EP Application No. 15 831 684.4.
J. Coburn et al., "Biomimetics of the Extracellular Matrix: An Integrated Three-Dimensional Fiber-Hydrogel Composite for Cartilate Tissue Engineering", Smart Struct. Syst., 7(3), pp. 213-222 (2011).
English language summary of JPO Office Action dispatch dated May 8, 2019 issued in counterpart Japanese Application 2017-528772.
Japanese language summary of JPO Office Action dispatch dated May 8, 2019 issued in counterpart Japanese Application 2017-528772.
Saez/Martinez, Journal of Applied Polymer Science, 2011, vol. 120, pp. 124-132(2011).

\* cited by examiner

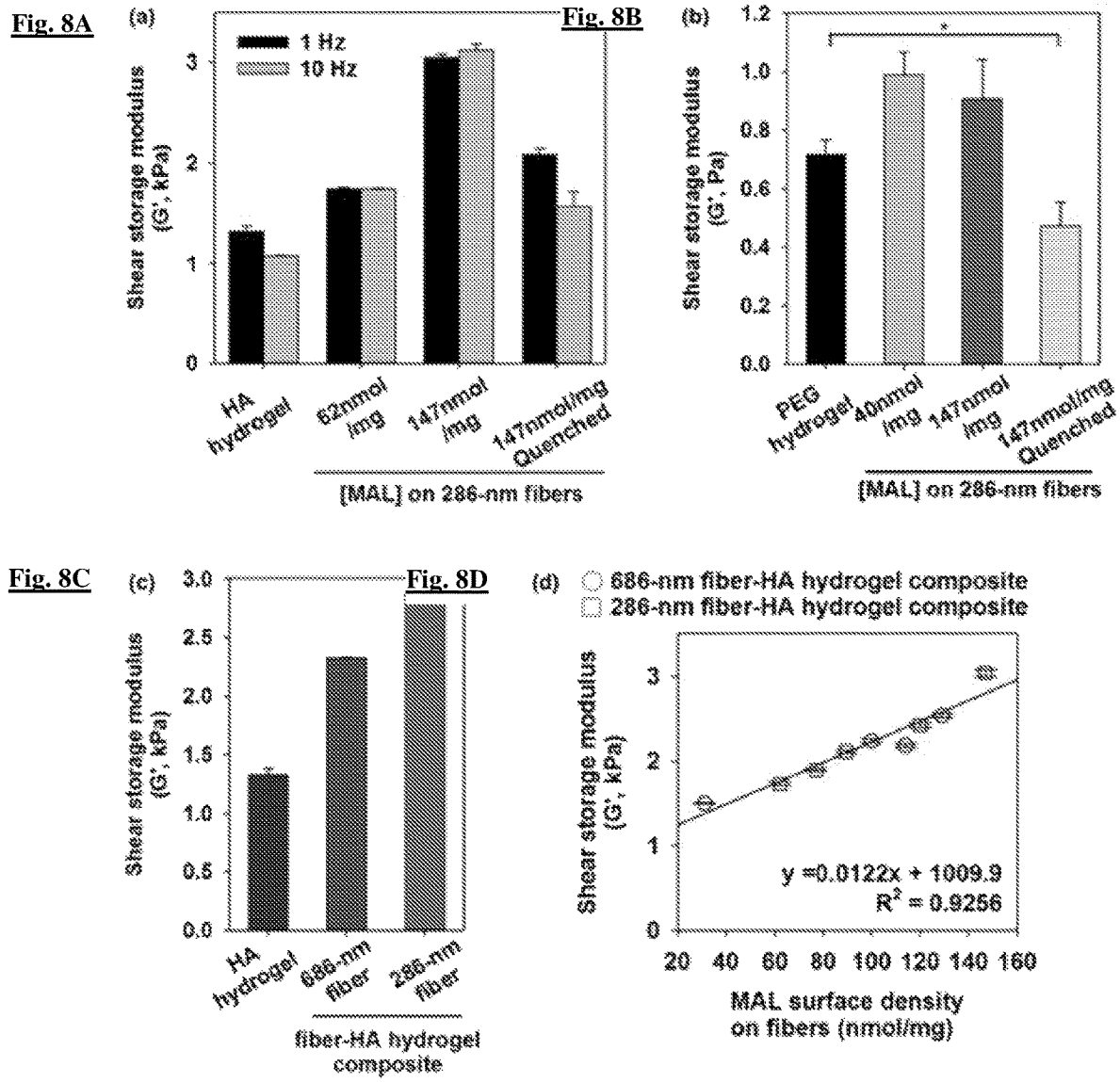

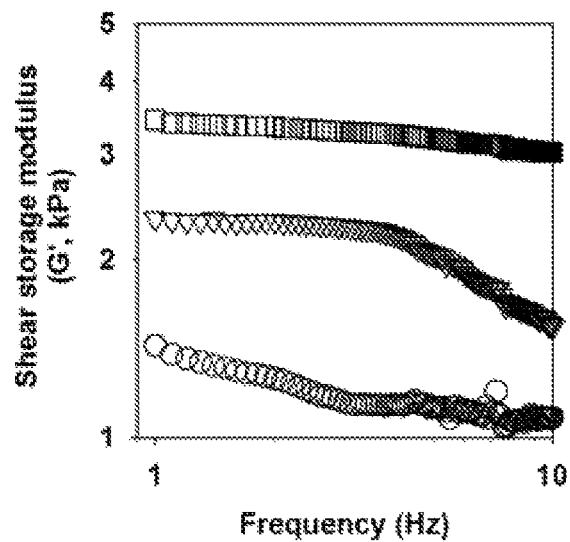
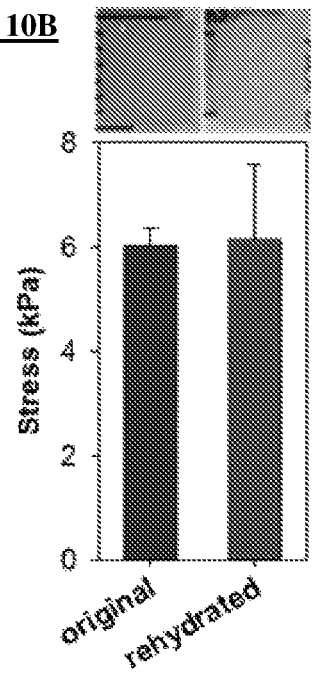
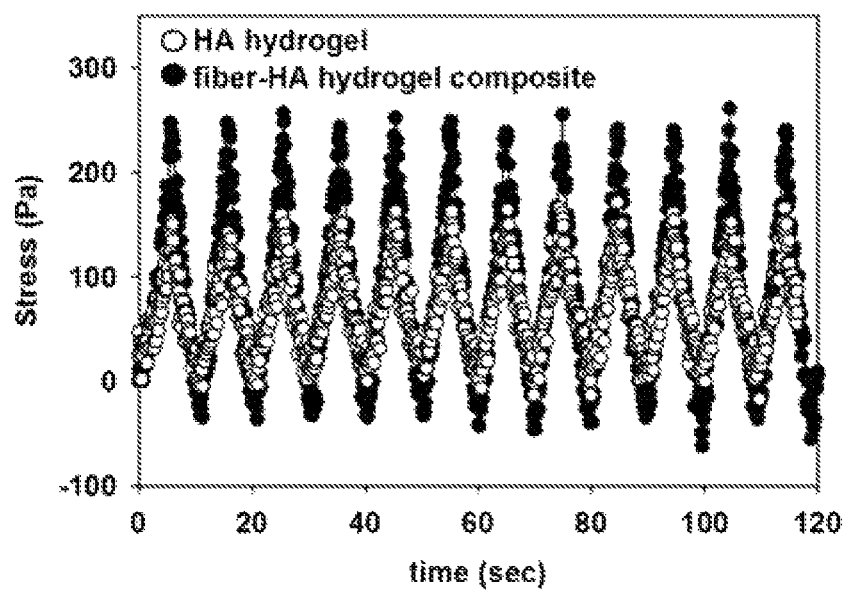
Fig. 10A a) ○ HA hydrogel
▽ 686-nm fiber-HA hydrogel composite
□ 286-nm fiber-HA hydrogel composite
Fig. 10B
Fig. 10C Fig. 11A    Fig. 11B    Fig. 11C
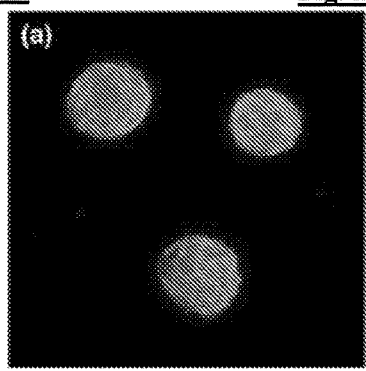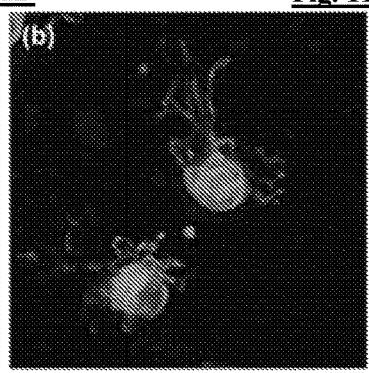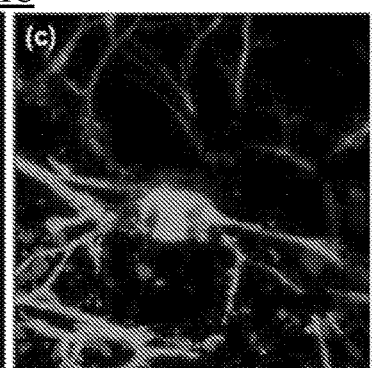
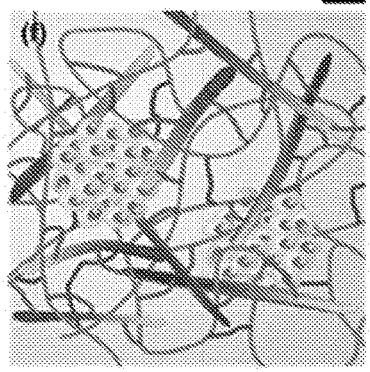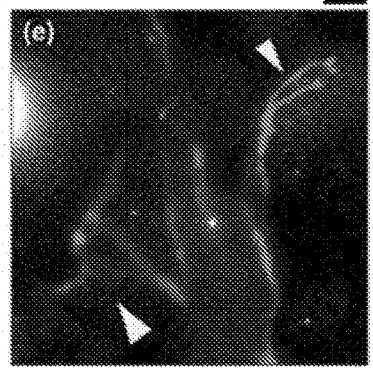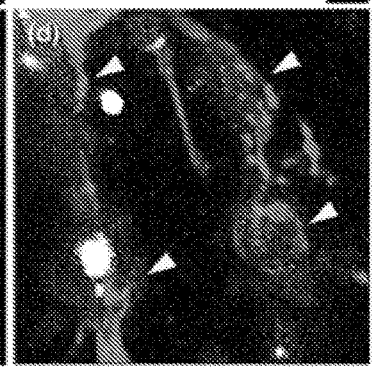
Fig. 11F    Fig. 11E    Fig. 11D Fig. 19A
Fig. 19B
Fig. 19C
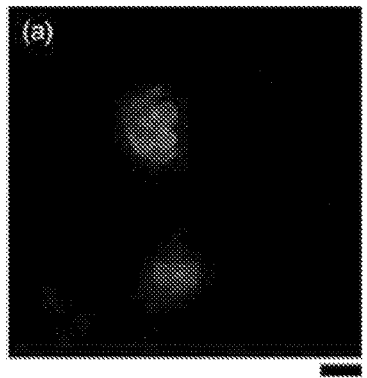
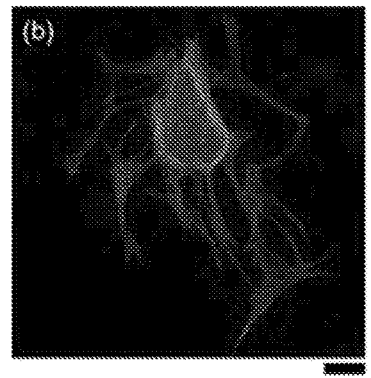
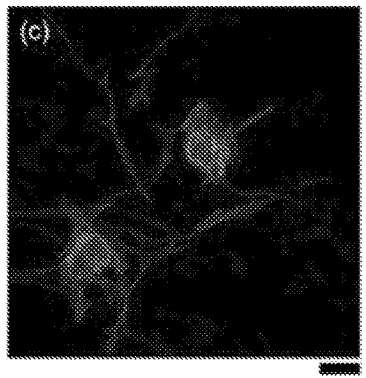

COMPOSITE MATERIAL FOR TISSUE RESTORATION

CROSS-REFERENCE TO RELATED APPLICATIONS

The present application is a continuation, pursuant to 35 U.S.C. § 111(e), of international application Ser. No. PCT/US2015/045494, filed Aug. 17, 2015, designating the United States and published in English on Feb. 18, 2016 as publication No. WO 2016/025945 A1, which claims priority to, and the benefit under 35 U.S.C. § 119(e) of U.S. Provisional Application No. 62/038,030, filed Aug. 15, 2014 and entitled, "Composite Material for Tissue Restoration". The entire contents of the aforementioned patent applications are incorporated herein by this reference.

BACKGROUND

1. Field

The present disclosure relates to composite materials and methods that restore lost soft tissue volume while promoting soft tissue regeneration.

2. Description of Related Art

Soft tissue defects resulting from trauma, oncologic resection, or congenital malformation are difficult to treat by conventional means. Current therapies, including tissue rearrangements or tissue transfer, cause donor site defects. Other therapies, such as prosthetic implants, lead to fibrosis and encapsulation. Existing strategies to promote tissue ingrowth are also inadequate for the treatment of soft tissue defects. Current acellular matrices result in flat, fibrotic sheets of tissue rather than the soft, three-dimensional tissue required for ideal reconstructions. Finally, while fat grafting can restore soft tissue defects, its wider use is hampered by variable graft survival and limited volumes of restoration. An ideal approach to soft tissue reconstruction would encourage regeneration of soft tissues such as adipose tissue in vivo followed by implantation of the tissues to promote regeneration. However, adipose tissue regrowth requires a suitable matrix for cells to attach, migrate, proliferate, differentiate, and organize into new tissue. Much of the native extracellular matrix (ECM) is missing at the repair site. Therefore, recreating a synthetic matrix that not only immediately restores the lost tissue volume, but also reconditions the microenvironment, supports host cell infiltration, and encourages regeneration of soft tissue, becomes an essential task when repairing soft tissue defects using adipose tissue-based reconstruction.

Hydrogels offer several advantages as a filler material for soft tissue reconstruction. However, to achieve sufficient mechanical property, higher crosslinking densities are usually required. Under these conditions, however, host tissue cells (e.g., adipocyte progenitors and endothelial progenitors) are not able to penetrate and grow into the scaffolds. In case of degradable hydrogels, scarring and fibrous tissue formation are typical because ingrowth of host tissue occurs too slowly, or at least at a pace slower than the absorption of the fiber material.

Recently, functionalized nanofibers have been developed to serve as ECM mimics to support various cell activities. FDA-compliant synthetic biodegradable poly-α-esters, such as polycaprolactone (PCL) or poly(lactide-co-glycolide) (PLGA) can be used to generate nanofibers through a process known as electrospinning. Biodegradable sutures and implants prepared from these polymers have been widely used clinically due to their excellent track record on biocompatibility. Various nanofibers of varying diameters and topographies for stem cell engineering applications have been developed. These nanofibers, however, do not offer macroscopic structures, making them difficult to use as 3D scaffolds.

Given the various problems associated with such conventional methods and systems, there is still a need in the art for improved solutions to healing soft tissue defects. The present disclosure provides a solution for this need that overcomes the various problems noted in the art.

SUMMARY

The invention is based, at least in part, upon identification of scaffold complexes having polymeric fiber components that possess improved properties (e.g., improved qualities for reconstruction of soft tissue, as detailed further infra).

In one aspect, the invention provides a scaffold complex that includes a polymeric fiber having a mean diameter of from about 100 nm to about 8000 nm covalently linked to a hydrogel material, where the ratio of fiber to hydrogel material is from about 1:10 to about 10:1 on a component-mass basis, or from about 1 to 50 mg/mL on a concentration basis.

In one embodiment, the polymeric fiber includes a biocompatible biodegradable polyester. Optionally, the polymeric fiber includes polycaprolactone.

In another embodiment, the hydrogel material is present in the complex in a functional network.

In an additional embodiment, the ratio of fiber to anhydrous hydrogel material is from about 1:10 to about 10:1.

In another embodiment, the polymeric fiber includes a non-woven polymeric fiber.

In certain embodiments, the polymeric fiber includes an electrospun polycaprolactone fiber. Optionally, the polymeric fiber includes a synthetic polymeric material comprising a poly(lactic-co-glycolic acid), a polylactic acid, and/or a polycaprolactone, or a combination thereof.

In one embodiment, the complex is formulated to be substantially biocompatible. Optionally, the polymeric fiber includes a biological polymeric material that includes a silk, a collagen, a chitosan, and/or a combination thereof.

In one embodiment, the hydrogel material includes hyaluronic acid. Optionally, the hydrogel material includes a hydrogel material that includes a poly(ethylene glycol), a collagen, a dextran, an elastin, an alginate, a fibrin, a alginate, a hyaluronic acid, a poly(vinyl alcohol), a derivative thereof, or a combination thereof.

In certain embodiments, the hydrogel material includes a processed tissue extracellular matrix.

In one embodiment, the processed tissue extracellular matrix is derivable from an adipose tissue.

In another embodiment, the scaffold complex includes a non-woven polycaprolactone fiber.

In one embodiment, the hydrogel material includes a hyaluronic acid substantially covering at least a portion of an outer surface of the polycaprolactone fiber.

In certain embodiments, the hydrogel material is bonded to the outer surface of the polymer fiber.

In another embodiment, the scaffold complex further includes a crosslinking moiety present in an amount effective to introduce bonding between polymer fiber and hydrogel material.

In certain embodiments, the scaffold complex includes a plurality of pores present on or within a surface of the scaffold complex, where the pores are present at a concentration of at least about 50 pores per cm$^2$ of the surface, and where at least 80% of the pores have an average pore diameter on the surface is at least about 5 microns.

In additional embodiments, the scaffold complex further includes a cross-linking moiety present in an amount effective to induce cross-linking between polycaprolactone fiber and hyaluronic acid.

Optionally, the scaffold complex promotes tissue growth and cell infiltration when implanted into a target tissue present in a human subject.

In certain embodiments, the scaffold complex is substantially biodegradable when implanted into a human tissue.

In one embodiment, the scaffold complex is substantially non-biodegradable when implanted into a human tissue.

In another embodiment, the scaffold complex further includes a therapeutic agent selected from a cell, a small molecule, a nucleic acid, and a polypeptide.

Another aspect of the invention provides an implantable biomaterial that includes a scaffold complex of the invention.

In certain embodiments, the implantable material is substantially acellular and/or is substantially free of polypeptides.

In one embodiment, the implantable material is formulated for administration by injection.

In another embodiment, the implantable material is formulated for subdermal administration.

An additional aspect of the invention provides a kit containing implantable material of the invention.

A further aspect of the invention provides a medical device for retaining tissue shape in a subject undergoing a surgical procedure, that includes the scaffold complex and/or the implantable material of the invention in an amount effective to provide for the retention of a tissue shape when administered to the subject.

Another aspect of the invention provides a method for preparing an implant for tissue or cartilage repair, the method involving the steps of: providing an acellular, three-dimensional scaffold that includes polymeric fibers oriented to produce a plurality of pores, where at least a portion of the polymeric fibers are cross-linked to other polycaprolactone fibers; disposing a composition that includes a hydrogel material on the polymeric fibers to form a complex; and reacting or stabilizing the complex to form a stabilized implant, thereby preparing the implant.

Optionally, the tissue includes a soft tissue.

A further aspect of the invention provides a method for preparing an implant for tissue or cartilage repair, the method involving the steps of: providing an acellular, three-dimensional scaffold that includes polymeric fibers oriented to produce a plurality of pores; disposing a composition that includes a hydrogel material on the polymeric fibers to form a complex; and reacting or stabilizing the complex to form a stabilized implant where at least a portion of the polymeric fibers are cross-linked to the hydrogel material.

In certain embodiments, the three-dimensional scaffold includes reactive polycaprolactone fibers.

A further aspect of the invention provides a method for preparing an implant for tissue or cartilage repair, the method involving the steps of: providing an acellular, three-dimensional scaffold that includes polymeric fibers oriented to produce a plurality of pores; disposing a composition that includes a hydrogel material on the polymeric fibers to form a complex; and reacting or stabilizing the complex to form a stabilized implant where at least a portion of the polymeric fibers are cross-linked to the hydrogel material.

An additional aspect of the invention provides a method for resolving a tissue defect resulting from a trauma or surgical intervention, the method involving distending the tissue, where distending the tissue includes implanting an effective amount of the scaffold complex of the invention into the tissue to thereby distend it.

Another aspect of the invention provides a method for reducing or reversing a tissue defect resulting from an aging-associated disease, disorder or condition, the method involving distending the tissue including the tissue, where distending the tissue includes implanting an effective amount of a scaffold complex of the invention into the tissue to thereby distend it.

Optionally, the tissue defect includes pleural tissue, muscle tissue, skin, or a combination thereof.

In at least one aspect, the invention provides a composite material that includes a gel and at least one nanostructure disposed within the gel. The gel can be hydrogel or any other suitable gel. The nanostructure can be a nanofiber or any other suitable nanostructure. The nanostructure can be covalently bonded to the gel. The nanostructure can be made of polycaprolactone (PCL) or any other suitable material.

In at least another aspect, the invention provides a method for healing a soft tissue defect comprising applying a composite material to a soft tissue defect, wherein the composite material includes a gel and a nanostructure disposed within the gel.

In still another aspect, the invention provides a method for manufacturing a composite material for use in healing soft tissue defects w include providing a gel and disposing nanofibers within the gel.

Where applicable or not specifically disclaimed, any one of the embodiments described herein are contemplated to be able to combine with any other one or more embodiments, even though the embodiments are described under different aspects of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 8A depicts the effect of interfacial bonding density on shear storage modulus of the PCL fiber-HA hydrogel composite. *$p<0.05$ (Student-t test).

FIG. 8B depicts the effect of interfacial bonding density shear storage modulus of the PCL fiber-HA hydrogel. The values of shear storage modulus were measured at 1-Hz frequency. *$p<0.05$ (Student-t test).

FIG. 8C depicts the effect of fiber diameter on shear storage modulus of the PCL fiber-HA hydrogel composite. The values of shear storage modulus were measured at 1-Hz frequency. *$p<0.05$ (Student-t test).

FIG. 8D summarizes the effect of interfacial bonding density and fiber diameter on shear storage modulus of the PCL fiber-HA hydrogel composite. The values of shear storage modulus were measured at 1-Hz frequency. *$p<0.05$ (Student-t test).

FIG. 10A depicts the mechanical strength of the fiber-HA hydrogel composite under different frequencies. Shear storage moduli of the HA hydrogel and the composites are measured against different frequencies of shear loading.

FIG. 10B depicts the mechanical strength of a fiber-HA hydrogel composite following lyophilization and rehydration. Comparison for the compression stress of the composites before and after rehydration was conducted at a strain rate of =40%.

FIG. 10C depicts the mechanical strength of a fiber-HA hydrogel composite under different cyclic loading. The compressive stresses of an HA hydrogel and the corresponding composite are measured against cyclic loading at a strain rate of =25%.

FIG. 11A depicts the migration ability of human ASCs in an HA hydrogel on Day 27. The HA hydrogel control and the two composites are selected to exhibit similar compressive moduli of around 1.9 kPa. F-actin and nuclei of hASCs are stained with Alexa Fluor® 568 phalloidin (red) and DAPI (blue), respectively. Nanofibers are labeled with Alexa Fluor® 647 (white).

FIG. 11B depicts the migration ability of human ASCs in nanofiber-HA hydrogel composite on Day 27. The HA hydrogel control and the two composites are selected to exhibit similar compressive moduli of around 1.9 kPa. F-actin and nuclei of hASCs are stained with Alexa Fluor® 568 phalloidin (red) and DAPI (blue), respectively. Nanofibers are labeled with Alexa Fluor® 647 (white). Scale bar=100 μm.

FIG. 11C depicts the migration ability of human ASCs in RGD-nanofiber-HA hydrogel composite on Day 27. The HA hydrogel control and the two composites are selected to exhibit similar compressive moduli of around 1.9 kPa. F-actin and nuclei of hASCs are stained with Alexa Fluor® 568 phalloidin (red) and DAPI (blue), respectively. Nanofibers are labeled with Alexa Fluor® 647 (white). Scale bar=100 μm.

FIG. 11D depicts the migration ability of human ASCs in RGD-nanofiber-HA hydrogel composite on Day 27. The HA hydrogel control and the two composites are selected to exhibit similar compressive moduli of around 1.9 kPa. Yellow arrows indicate cells adhering to fibers or fibers clusters. F-actin and nuclei of hASCs are stained with Alexa Fluor® 568 phalloidin (red) and DAPI (blue), respectively. Nanofibers are labeled with Alexa Fluor® 647 (white). Scale bar=20 μm.

FIG. 11E depicts the migration ability of human ASCs in nanofiber-HA hydrogel composite on Day 27. The HA hydrogel control and the two composites are selected to exhibit similar compressive moduli of around 1.9 kPa. Yellow arrows indicate cells adhering to fibers or fibers clusters. F-actin and nuclei of hASCs are stained with Alexa Fluor® 568 phalloidin (red) and DAPI (blue), respectively. Nanofibers are labeled with Alexa Fluor® 647 (white). Scale bar=20 μm.

FIG. 11F illustrates human ASC spheroids in the composite structure with interfacial bonding (red) between PCL fibers (green) and HA chain network (blue).

FIG. 19A depicts migration ability of human ASCs in a HA hydrogel with G'=24.85±2.92 Pa on Day 4. The HA hydrogel is prepared with 2.5 mg/ml of HA-SH and 5.0 mg/ml of PEGDA. Scale bar=100 μm.

FIG. 19B depicts migration ability of human ASCs in a fiber-HA hydrogel composite (G'=32.29±2.16 Pa) on Day 4. The composite is prepared with 2.5 mg/ml of HA, 5.0 mg/ml of PEGDA and 10 mg/ml fibers with an average fiber diameter of 1.0 μm. Scale bar=100 μm.

FIG. 19C depicts migration ability of human ASCs in a fiber-HA hydrogel composite (G'=39.56±1.26 Pa) on Day 4. The composite is fabricated with 2.5 mg/ml of HA, 5.0 mg/ml of PEGDA and 10 mg/ml fibers with an average fiber diameter of 286 nm. Scale bar=100 μm.

DETAILED DESCRIPTION

Figure 1A:
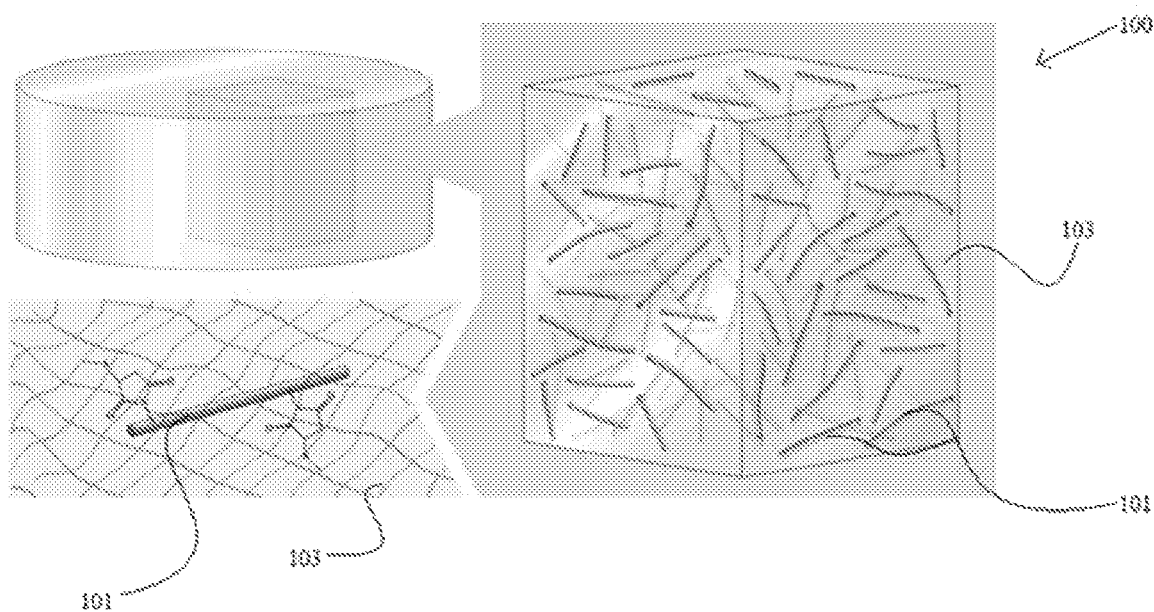
FIG. 1A illustrates the structure of an embodiment of a composite in accordance with this disclosure, showing nanostructures disposed in a gel, and in particular, the covalent attachment of the nanostructure to functional groups in the gel.

The present invention relates to composite materials comprising a hydrogel and a nanostructure for use in methods for reconstruction of soft tissue. The invention also relates to methods for repairing or reconstructing a soft tissue injury using a composition comprising a hydrogel and a nanostructure disposed therein. The invention in other aspects also relates to a method of fabricating a composition for use in soft tissue reconstruction where the composition comprises a hydrogel and a nanostructure disposed therein.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

Definitions

As used herein, a "scaffold complex" includes any covalent association of two components: a polymeric fiber and a hydrogel material. The scaffold complex contains the polymeric fiber and hydrogel material in a "functional network", meaning that the interactions between components results in a chemical, biochemical, biophysical, physical, or physiological benefit. In addition, a functional network may include additional components, including cells, biological materials (e.g., polypeptides, nucleic acids, lipids, carbohydrates), therapeutic compounds, synthetic molecules, and the like. In certain embodiments, the scaffold complex promotes tissue growth and cell infiltration when implanted into a target tissue present in a human subject.

As used herein, the term "hydrogel" is a type of "gel," and refers to a water-swellable polymeric matrix, consisting of a three-dimensional network of macromolecules (e.g., hydrophilic polymers, hydrophobic polymers, blends thereof) held together by covalent or non-covalent crosslinks that can absorb a substantial amount of water (e.g., 50%, 60% 70%, 80%, 90%, 95%, 96%, 97%, 98%, 99% or greater than 99% per unit of non-water molecule) to form an elastic gel. The polymeric matrix may be formed of any suitable synthetic or naturally occurring polymer material. As used herein, the term "gel" refers to a solid three-dimensional network that spans the volume of a liquid medium and ensnares it through surface tension effects. This internal network structure may result from physical bonds (physical gels) or chemical bonds (chemical gels), as well as crystallites or other junctions that remain intact within the extending fluid. Virtually any fluid can be used as an extender including water (hydrogels), oil, and air (aerogel). Both by weight and volume, gels are mostly fluid in composition and thus exhibit densities similar to those of their constituent liquids. A hydrogel is a type of gel that uses water as a liquid medium. The definitions of "hydrophobic" and "hydrophilic" polymers are based on the amount of water vapor absorbed by polymers at 100% relative humidity. According to this classification, hydrophobic polymers absorb only up to 1% water at 100% relative humidity ("rh"), while moderately hydrophilic polymers absorb 1-10% water, hydrophilic polymers are capable of absorbing more than 10% of water, and hygroscopic polymers absorb more than 20% of water. A "water-swellable" polymer is one that absorbs an amount of water greater than at least 50% of its own weight, upon immersion in an aqueous medium.

The term "crosslinked" herein refers to a composition containing intramolecular and/or intermolecular crosslinks, whether arising through covalent or noncovalent bonding, and may be direct or include a cross-linker. "Noncovalent" bonding includes both hydrogen bonding and electrostatic (ionic) bonding.

The term "polymer" includes linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da. Polymers and oligomers may be naturally occurring or obtained from synthetic sources.

Soft Tissue Reconstruction

Devastating soft tissue losses from tumor extirpation, trauma, aging, or congenital malformation affect millions of people each year. The loss of tissues including skin, fat, and muscle lead to major functional and aesthetic disturbances that are difficult to treat by conventional means. As an example, over 300,000 partial mastectomies are performed in the United States each year, leading to disfiguring breast scars from the loss of breast soft tissue. Existing options for soft tissue restoration have significant drawbacks. Autologous tissue flaps requires moving soft tissues from another part of the body in lengthy surgical procedures that leave donor-site deficits LoTempio 2010. *Plastic and Reconstructive Surgery*, 126(2), 393-401; Patel 2012. *Annals of Plastic Surgery*, 69(2), 139-144}. Prosthetic implants are prone to foreign-body response leading to fibrosis and encapsulation {Calobrace 2014 *Plastic and Reconstructive Surgery*, 134(1 Suppl), 6S-11; Tsoi 2014. *Plastic and Reconstructive Surgery*, 133(2), 234-249}. Fat grafting involving placement of adipocytes harvested during liposuction is limited to small volumes and is hampered by poor graft survival {Kakagia 2014 *Surgical Innovation*, 21(3), 327-336; Largo 2014 *British Journal of Plastic Surgery*, 67(4), 437-448}. Finally, injectable hydrogel soft tissue fillers can be used, but these are suitable only for smaller defects and the volume restoration they provide is transient {Young 2011. *Acta Biomaterialia*, 7(3), 1040-1049; Varma 2014 *Acta Biomaterialia*, 10(12), 4996-5004}. A new generation of tissue engineering solutions has been proposed to focus on using hydrogel scaffolds as templates to regenerate soft tissues such as adipose tissue at the site of reconstruction.

Current Tissue Engineering Approaches to Soft Tissue Reconstruction

Adipose-derived stem cells (ASCs) have been identified in wound beds surrounding soft tissue defects {Salibian 2013 *Archives of plastic surgery* 40.6: 666-675}. They can be differentiated into soft tissues such as fat, when supported with a suitable matrix microenvironment. Therefore strategies to fill the repair site with functional materials have the potential to enable the regeneration of new tissue using the endogenous ASCs. Hydrogels have been widely studied as a scaffold matrix for the regeneration of tissue defects due to their three-dimensional (3D) nature and elastic properties, which are similar to those of soft tissues. Various methods have been used to generate hydrogel scaffolds with moduli similar to that of native fat tissues (~2 kPa) {Alkhouli 2013 *American Journal of Physiology. Endocrinology and Metabolism*, 305(12), E1427-35; Sommer 2013 *Acta biomaterialia* 9.11 (2013): 9036-9048} while maintaining their volume and shape against physical stress from the surrounding tissue. This requires higher crosslinking density and smaller average pore size {Ryu 2011 *Biomacromolecules* 12.7 (2011): 2653-2659; Khetan 2013 *Nature Materials*, 12(5), 458-465; Li 2014 *Journal of Neurotrauma*, 31(16), 1431-1438}, leading to low cellular infiltration and poor regeneration. The ability for hydrogel scaffolds to promote cellular infiltration is the key to successful soft tissue restoration. Lack of vascular infiltration is responsible for the failure of large-volume fat grafting and other tissue engineering attempts. No currently available materials can fill the volume lost in soft tissue defects while promoting early vascularization and ASC differentiation to regenerate soft tissue.

Hydrogel Matrix

Over the past few years, Li and Wen have developed a hyaluronic acid (HA) hydrogel conjugated with laminin-derived loop peptide (CCRRIKVAVWLC, 10 µM) with optimized pore size and modulus (10-100 Pa) for stem cell transplantation. They have shown that this hydrogel supports robust neural stem cell (NSC) migration and neurite sprouting from the differentiated cells {Li 2014 Journal of Neurotrauma, 31(16), 1431-1438}. In a rat controlled cortical injury (CCI) model for traumatic brain injury, this hydrogel, when injected on day 3 after the CCI injury, promoted significant vasculature network formation filling the lesion site (>10 mm) at 4 weeks to 6 months post implantation. This improved angiogenesis was attributed to the ability of this hydrogel to retain and present tissue-secreted growth factors, particularly vascular endothelial growth factor (VEGF). Literature reports also revealed that small HA degradation fragments of 3-10 disaccharide units were potent regulators of endothelial cell proliferation, migration, tubule formation, and angiogenesis {Slevin 2002 *Journal of Biological Chemistry*, 277(43), 41046-41059}. In a recent study, the effectiveness of this HA hydrogel to deliver human fetal tissue derived-NSC spheroids in a brain lesion site after CCI injury was tested. This HA hydrogel delivered robust vascular formation inside the scaffold matrix following transplantation. Regenerated blood vessels grew into the lesion and penetrated through the implanted matrix, and supported the survival and growth the neuronal progenitors. Even though these studies are not for adipose tissue regeneration, these results confirmed the unique ability of this optimized HA hydrogel composition in promoting host vascular ingrowth. More importantly, the hydrogel matrix is sufficiently porous to allow robust cell migration inside the hydrogel matrix. However, using this HA hydrogel directly for soft tissue reconstruction is not feasible, as its mechanical property is not sufficiently high to maintain the integrity of the implantation site—the surrounding adipose tissue has a modulus of more than 10-times higher. Increasing crosslinking density to improve its modulus will make it poorly permeable for cell infiltration and migration. A new strategy is needed to increase the mechanical property without significantly decreasing the average pore size of the bulk hydrogel. Provided are hydrogel materials that contain and/or are isolated from a processed tissue extracellular matrix, such as extracellular matrix derived and/or derivable from an adipose tissue.

Scaffold Complexes.

Provided herein are scaffold complexes suitable for use medical devices that are incorporated into a tissue of a human subject to whom the complexes are administered, e.g., by injection or implantation. The scaffold complexes contain a polymeric fiber, generally having a mean diameter of from about 10 nm to about 10,000 nm, such as about 100 nm to about 8000 nm, or about 150 nm to about 5,000 nm, or about 100, 150, 200, 250, 300, 350, 400, 450, 500, 600, 700, 800, 900, 1,000, 1,500, 2,000, 2,500, 3,000, 3,500, 4,000, 4,500, 5,000, 5,500, 6,000, 6,500, 7,000, 7,500, or 8,000. As provided herein, the ratio of polymeric fiber to hydrogel material can be determined my any means known in the art. For example, the ratio of polymeric fiber to hydrogel material is from about 1:100 to about 100:1 on a component-mass basis, such as about 1:50 to about 50:1, or 1:10 to about 10:1, such as 1:5 to about 5:1, such as about 1:3 to about 3:1. The ratio of polymeric fiber to hydrogel material is also provided as a concentration basis, e.g., a given weight of polymeric fiber per volume of hydrogel material. For example the concentration is from about 1 to 50 mg/mL. The hydrogel material is generally disposed on the polymer fiber, such as being bonded to the outer surface (or an outer surface, depending upon the composition and shape) of the polymer fiber. The scaffold complex is not generally a uniform solid material. Instead, scaffold complexes contain a plurality of pores present on or within a surface of the scaffold complex. The presence, size, distribution, frequency and other parameters of the pores can be modulated during the creation of the scaffold complex. Pore size can be from below about 1 micron to up to 100 microns, including 1, 2, 3, 4 5, 10, 15, 20, 30, 40, 50, 60 70, 80, 90 or 100 microns, and the size thereof may be narrowly tailored, e.g., such that at least 40%, such as 50%, 60%, 70%, 80%, 90%, 95% or greater than 95% of the pores are in a desired size or within a desired size range.

The scaffold complexes of the invention are suitable for incorporation into a tissue of a human subject, and thus they are generally "biocompatible", meaning capable of interacting with a biological system (such as found in a human subject) without inducing a pathophysiological response therein and/or thereby. In some embodiments the scaffold complex is provided in order to be durably retained in the tissue. Alternatively, the scaffold complexes are transiently retained in the human subject, and are provided as substantially biodegradable. Preferably, a polymeric fiber contains a biocompatible biodegradable polyester. In a preferred embodiment, the polymeric fiber contains polycaprolactone.

As provided herein, one preferred form of interaction of the complex containing polymer fiber and hydrogel includes a crosslinking moiety, generally present in an amount effective to introduce bonding between polymer fiber and hydrogel material, e.g., to induce cross-linking between polycaprolactone fiber and hyaluronic acid.

Scaffold Design for Soft Tissue Restoration

The composite concept has been widely used as a material-reinforcement mechanism. For example, adding hydroxyapatite particles into hydrogel can increase its stiffness {Wu 2008 *Materials Chemistry and Physics* 107.2 (2008): 364-369}, and the composite tensile modulus increases even more for elongated particles {Yusong 2007 *Journal of Materials Science*, 42(13), 5129-5134}. Electrospun nanofiber meshes have been used widely as a tissue engineering substrate due to their topographical similarity to the native ECM. Of particular interest, the decellularized ECM of adipose tissue is highly fibrous and porous in nature (FIG. 6G) {Young 2011. *Acta Biomaterialia*, 7(3), 1040-1049}. Several recent studies have attempted to recapitulate the fibrous components by introducing fragmented poly (lactide) (PLA) or chitosan fibers to a polyethylene glycol (PEG), polyacrylamide, or alginate hydrogel {Coburn 2011 *Smart Structures and Systems*, 7(3), 213; #37; Zhou 2011 *Colloids and Surfaces B: Biointerfaces*, 84(1), 155-162; Shin 2015 *Journal of Materials Chemistry*}. The fragmented fibers are mixed with hydrogel precursor solutions and incorporated into hydrogel during the gelation process to create a 3D architecture. These fiber-embedded hydrogels have shown improved mechanical properties over the corresponding hydrogels. However, there has been no report on testing host cell infiltration in vivo. In addition, these hydrogels are non-degradable and require adhesive ligands for adipocyte adhesion and differentiation.

Nanofiber-Hydrogel Composite Design

To achieve fiber-reinforcement effect while maintaining high porosity in the hydrogel phase, an electrospun fiber-hydrogel composite that offers superior properties as compared to other scaffolds is provided. Beyond blending nanofibers and a hydrogel matrix, which has been reported previously {Coburn 2011 *Smart Structures and Systems*, 7(3), 213}, introduced here are interfacial bonding between fiber surfaces and the hydrogel crosslinking network (FIG. 6). Such a composite design not only allows stronger mechanical reinforcement from the solid fiber component, but also allows independent tuning of bulk mechanical properties and the average pore size/porosity of the hydrogel phase, enabling both optimal cell infiltration properties and structural integrity. It is further contemplated that fibers can be employed as preferred cell adhesion substrates for ASCs and endothelial progenitors, therefore acting as a guide to support cell migration and ASC differentiation.

Innovation

Figures 6A, 6B, 6C, 6D, 6E, 6F, 6G:
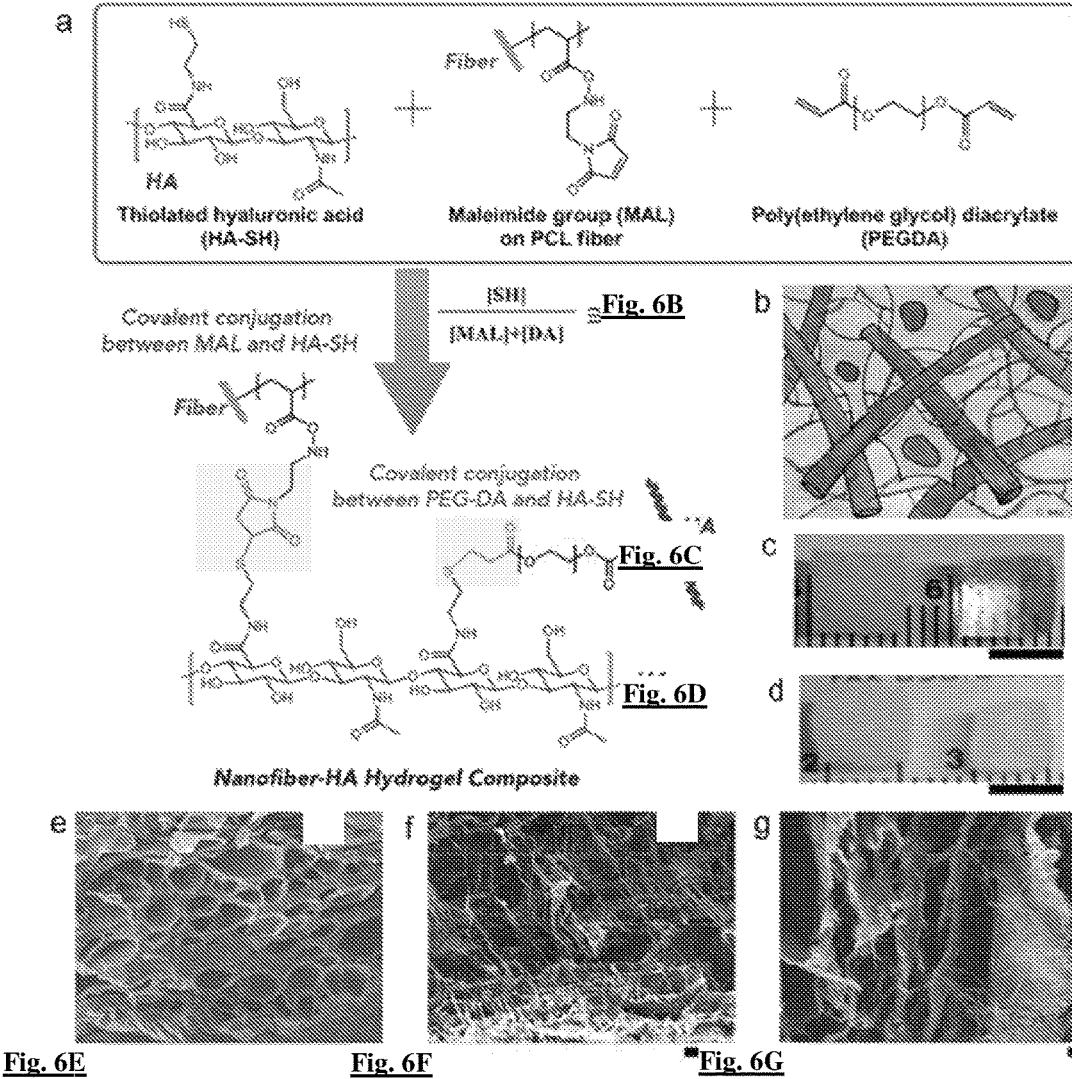
FIG. 6A depicts a synthesis scheme for the polycaprolactone (PCL) fiber-HA hydrogel composite.
FIG. 6B depicts a schematic illustration of the composite structure with interfacial bonding between PCL fibers and HA chain network.
FIG. 6C depicts an optical image showing the general appearance of a freshly prepared, cylindrical fiber-HA hydrogel composite (left) and a HA hydrogel (right) with the same dimensions (scale bar=5 mm).
FIG. 6D depicts an optical image of the same set of samples as shown in FIG. 6C after lyophilization and rehydration.
FIG. 6E depicts an SEM image of a cross-section of an HA hydrogel (scale bar=40 μm).
FIG. 6F depicts an SEM image of a cross-section of the PCL fiber-HA hydrogel composite (scale bar=100 μm); note that this is the same sample and image as FIG. 1D, included here for comparison purposes.
FIG. 6G depicts an SEM image of a cross-section of a decellularized native fat tissue (scale bar=10 μm).

In certain aspects, the key innovation is the nanofiber-hydrogel composite design with interfacial bonding between nanofiber surfaces and the hydrogel network (FIG. 6A). This engineered composite has the potential to drastically improve the mechanical property of the hydrogel without significantly decreasing the average pore size in the hydrogel phase. The introduction of interfacial bonding can offer superior mechanical strengthening effect comparing to just physical blending of the two components. This study will map out the range of mechanical properties (compression and shear moduli) attainable with electrospun polycaprolactone (PCL) fiber-HA hydrogel composites in contrast to blends. The second innovation is the demonstration of such a nanofiber-hydrogel composite to restore soft tissue defects. Preliminary characterization demonstrated that the composite shared structural characteristics with adipose tissue (FIG. 6) {Christman, 2012 US 20120264190 A1; Young 2011. *Acta Biomaterialia*, 7(3), 1040-1049}. It was hypothesized that this composite offers structural integrity and mechanical properties important for soft tissue regeneration. This study has also demonstrated the versatility and efficiency of composites, as compared to hydrogels.

The successful completion of this project will deliver an off-the-shelf solution for the restoration of missing soft tissue volume, particularly for larger defects where establishing vascular network, maintaining tissue repair site integrity, promoting cell migration and organization, and recruiting host cells are all crucial to a sustainable tissue restoration. The extensive clinical track record for the materials components used in this composite design, i.e. HA hydrogel and biodegradable polyester fibers, together with these preliminary data on tissue compatibility, suggested superior tissue compatibility and a straightforward regulatory approval path for clinical translation.

Features:

In some embodiments, the invention provides the interfacial bonding between nanofibers and polymer network in the hydrogel component. This is important for the formation of a "true" composite. It was demonstrated that blending such fibers and hydrogel did not provide the same degree of mechanical enhancement. There are also previous reports on the use of nanofiber-hydrogel blends. In other words, the interfacial bonding importantly differentiates this new work from the art. Furthermore, the interfacial bonding could include covalent bonds as shown in this manuscript, and secondary bonding, such as hydrogen bonds and electrostatic charge interaction.

This is also the first work in the field that demonstrates isotropic reinforcement—the composite is stronger in all orientations, as needed to replace volumetric defects of arbitrary geometry. Designs with nanofiber mats or a small number of aligned filaments are inherently anisotropic. This design is capable of forming both isotropic and anisotropic materials The work presented herein, for at least certain aspects, defines the components used for the formation of composite to be a hydrogel network with sufficient pore size and porosity for cell migration and host tissue ingrowth, and nanofibers which loosely include polymer fibers with diameters ranging from 50 nm to 10 μm.

Gel/Hydrogel Component

The hydrogel composite of the invention can include any type of suitable hydrogel component. The invention contemplate nanostructure/gel composites that include any suitable gel component, including any suitable hydrogel component known in the art. The gel and/or hydrogels can be formed of any suitable synthetic or naturally-occurring materials.

For example, the polymer component of the gels and/or hydrogels can comprise a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000.

The cellulose esters and comprise a mixture of cellulose and cellulose ester monomer units; for example, commercially available cellulose acetate butyrate contains cellulose acetate monomer units as well as cellulose butyrate monomer units and unesterified cellulose units.

The gels/hydrogels of the invention may also be comprised of other water-swellable polymers, such as acrylate polymers, which are generally formed from acrylic acid, methacrylic acid, methyl acrylate, ethyl acrylate, methyl methacrylate, ethyl methacrylate, and/or other vinyl monomers. Suitable acrylate polymers are those copolymers available under the tradename "Eudragit" from Rohm Pharma (Germany), as indicated supra. The Eudragit series E, L, S, RL, RS and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L-30D-55 and Eudragit L-100-55 (the latter copolymer is a spray-dried form of Eudragit L-30D-55 that can be reconstituted with water). The molecular weight of the Eudragit L-30D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-30D-55, L-100-55, L-100, and S-100 can be replaced with other acceptable polymers having similar pH-dependent solubility characteristics.

Any of the herein-described gel/hydrogel compositions may be modified so as to contain an active agent and thereby act as an active agent delivery system when applied to a body surface (e.g., a site of tissue repair) in active agent-transmitting relation thereto. The release of active agents "loaded" into the present hydrogel compositions of the invention typically involves both absorption of water and desorption of the agent via a swelling-controlled diffusion mechanism. Active agent-containing hydrogel compositions may be employed, by way of example, in transdermal drug delivery systems, in wound dressings, in topical pharmaceutical formulations, in implanted drug delivery systems, in oral dosage forms, and the like.

Suitable active agents that may be incorporated into the present hydrogel compositions and delivered systemically (e.g., with a transdermal, oral, or other dosage form suitable for systemic administration of a drug) include, but are not limited to: analeptic agents; analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, antianginal agents, central nervous system (CNS) agents, beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids, including progestogens, estrogens, corticosteroids, androgens and anabolic agents; smoking cessation agents; sympathomimetics; tranquilizers; and vasodilators including general coronary, peripheral and cerebral. Specific active agents with which the present adhesive compositions are useful include, without limitation, anabasine, capsaicin, isosorbide dinitrate, aminostigmine, nitroglycerine, verapamil, propranolol, silabolin, foridone, clonidine, cytisine, phenazepam, nifedipine, fluacizin, and salbutamol.

For topical drug administration and/or medicated cushions (e.g., medicated footpads), suitable active agents include, by way of example, the following:

Bacteriostatic and bactericidal agents: Suitable bacteriostatic and bactericidal agents include, by way of example: halogen compounds such as iodine, iodopovidone complexes (i.e., complexes of PVP and iodine, also referred to as "povidine" and available under the tradename Betadine from Purdue Frederick), iodide salts, chloramine, chlorohexidine, and sodium hypochlorite; silver and silver-containing compounds such as sulfadiazine, silver protein acetyltannate, silver nitrate, silver acetate, silver lactate, silver sulfate and silver chloride; organotin compounds such as tri-n-butyltin benzoate; zinc and zinc salts; oxidants, such as hydrogen peroxide and potassium permanganate; aryl mercury compounds, such as phenylmercury borate or merbromin; alkyl mercury compounds, such as thiomersal; phenols, such as thymol, o-phenyl phenol, 2-benzyl-4-chlorophenol, hexachlorophen and hexylresorcinol; and organic nitrogen compounds such as 8-hydroxyquinoline, chlorquinaldol, clioquinol, ethacridine, hexetidine, chlorhexedine, and ambazone.

Antibiotic agents: Suitable antibiotic agents include, but are not limited to, antibiotics of the lincomycin family (referring to a class of antibiotic agents originally recovered from *streptomyces lincolnensis*), antibiotics of the tetracycline family (referring to a class of antibiotic agents originally recovered from *streptomyces aureofaciens*), and sulfur-based antibiotics, i.e., sulfonamides. Exemplary antibiotics of the lincomycin family include lincomycin, clindamycin, related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself, chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium.

Pain relieving agents: Suitable pain relieving agents are local anesthetics, including, but not limited to, acetamidoeugenol, alfadolone acetate, alfaxalone, amucaine, amolanone, amylocaine, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, .beta.-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and combinations thereof. Tetracaine, lidocaine and prilocaine are referred pain relieving agents herein.

Other topical agents that may be delivered using the present hydrogel compositions as drug delivery systems include the following: antifungal agents such as undecylenic acid, tolnaftate, miconazole, griseofulvine, ketoconazole, ciclopirox, clotrimazole and chloroxylenol; keratolytic agents, such as salicylic acid, lactic acid and urea; vessicants such as cantharidin; anti-acne agents such as organic peroxides (e.g., benzoyl peroxide), retinoids (e.g., retinoic acid, adapalene, and tazarotene), sulfonamides (e.g., sodium sulfacetamide), resorcinol, corticosteroids (e.g., triamcinolone), alpha-hydroxy acids (e.g., lactic acid and glycolic acid), alpha-keto acids (e.g., glyoxylic acid), and antibacterial agents specifically indicated for the treatment of acne, including azelaic acid, clindamycin, erythromycin, meclocycline, minocycline, nadifloxacin, cephalexin, doxycycline, and ofloxacin; skin-lightening and bleaching agents, such as hydroquinone, kojic acid, glycolic acid and other alpha-hydroxy acids, artocarpin, and certain organic peroxides; agents for treating warts, including salicylic acid, imiquimod, dinitrochlorobenzene, dibutyl squaric acid, podophyllin, podophyllotoxin, cantharidin, trichloroacetic acid, bleomycin, cidofovir, adefovir, and analogs thereof; and anti-inflammatory agents such as corticosteroids and nonsteroidal anti-inflammatory drugs (NSAIDs), where the NSAIDS include ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, and tiaprofenic acid.

For wound dressings, suitable active agents are those useful for the treatment of wounds, and include, but are not limited to bacteriostatic and bactericidal compounds, antibiotic agents, pain relieving agents, vasodilators, tissue-healing enhancing agents, amino acids, proteins, proteolytic enzymes, cytokines, and polypeptide growth factors.

For topical and transdermal administration of some active agents, and in wound dressings, it may be necessary or desirable to incorporate a permeation enhancer into the hydrogel composition in order to enhance the rate of penetration of the agent into or through the skin. Suitable enhancers include, for example, the following: sulfoxides such as dimethylsulfoxide (DMSO) and decylmethylsulfoxide; ethers such as diethylene glycol monoethyl ether (available commercially as Transcutol) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclaza-cycloheptan-2-one (available under the trademark Azone from Nelson Research & Development Co., Irvine, Calif; see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones;

and organic acids, particularly salicylic acid and salicylates, citric acid and succinic acid. Mixtures of two or more enhancers may also be used.

In certain other embodiments, the composite compositions of the invention comprising a gel (e.g., a hydrogel component) and a nanostructure may also comprise additional optional additive components. Such components are known in the art and can include, for example, fillers, preservatives, pH regulators, softeners, thickeners, pigments, dyes, refractive particles, stabilizers, toughening agents, detackifiers, pharmaceutical agents (e.g., antibiotics, angiogenesis promoters, antifungal agents, immunosuppressing agents, antibodies, and the like), and permeation enhancers. These additives, and amounts thereof, are selected in such a way that they do not significantly interfere with the desired chemical and physical properties of the hydrogel composition.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon.

The compositions can also include one or more preservatives. Preservatives include, by way of example, p-chlorom-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

The compositions may also include pH regulating compounds. Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of an individual's body surface.

The compositions may also include suitable softening agents. Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

The compositions may also include thickening agents. Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

In certain embodiments, the hydrogel composite of the invention comprising a hydrogel and a nanostructure further comprises a component that promotes angiogenesis. A challenge to achieving clinically relevant soft tissue regeneration prior to the present invention is that the regenerated tissue preferably should be re-vascularized. Therefore, any material that promotes soft tissue regeneration preferably should also encourage angiogenesis. One way to achieve this is through the use of heparin-containing hydrogel components, which can serve as growth factor binding sites to enrich and retain growth factors promoting angiogenesis and tissue formation.

In various other embodiments, the composite materials of the invention can be based on hyaluronic acid (HA) as they hydrogel material. HA is a non-sulfated, linear polysaccharide with repeating disaccharide units which form the hydrogel component. HA is also a non-immunogenic, native component of the extracellular matrix in human tissues, and widely used as a dermal filler in aesthetic and reconstructive procedures.

Breakdown of HA is facilitated by native hyaluronidases whose expression is increased in areas of tissue damage and inflammation. Importantly, studies have shown that small HA degradation fragments of 3-10 disaccharide units are potent regulators of endothelial cell proliferation, migration, tubule formation, and angiogenesis. These biological functions of HA are thought to be mediated via CD44 in a pathway involving Ras and PKC. Blockade of CD44/HA interactions using anti-CD44 antibodies reduced proliferation and migration of human microvascular endothelial cells in vitro. HA hydrogels have been investigated as potential matrices for cell delivery in a variety of models of cell and tissue injury. These hydrogels can serve as a protective and supporting scaffold for cells and can also reduce scarring. Thus, it is believed HA has a critical role in enhancing tissue regeneration by promoting cell infiltration and promoting angiogenesis.

First, the material has three-dimensional integrity and a consistency similar to that of native fat tissue. This renders it suitable for off-the-shelf restoration of missing soft tissue volume. Second, the material preferably may be deposited with a plurality of flexible nanofibers that can serve as substrates for migration of adipocytes and endothelial progenitors. Third, the material has sufficient porosity to allow these precursor cells to rapidly infiltrate and integrate into the scaffold rather than forming a fibrous capsule around it. Fourth, the HA hydrogel component provides compressibility and volumetric expansion while also providing important angiogenic cues. Fifth, the nanofiber and hydrogel components are biodegradable allowing them to be replaced by regenerated soft tissue. Sixth, all component materials have strong safety track records in numerous FDA-approved devices, potentially reducing regulatory hurdles for clinical translation.

The gel/hydrogel/nanostructure composites of the invention can also include tissue-repairing agents, such as, a number of growth factors, including epidermal growth factor (EDF), PDGF, and nerve growth factors (NGF's). For example, the compositions may include EGF. Epidermal Growth Factor (EGF) was discovered after the observation that cutaneous wounds in laboratory mice seemed to heal more rapidly when the mice were allowed to lick them. This was not simply due to some antiseptic agent in saliva (such as lysozyme). A specific growth factor, now known as EGF, was shown to be responsible. EGF is identical to urogastrone, and has angiogenic properties. Transforming growth factor-alpha (TGF-.alpha.) is very similar, binding to the same receptor and is even more effective in stimulating epithelial cell regeneration (epithelisation).

Thus, hydrogels of the present invention comprising EGF/TGF may advantageously be used in the acceleration of wound healing and burns, reduction in keloid scar formation (especially for burns), skin engraftment dressings, and the treatment of chronic leg ulcers.

Tissue-repairing agents useful in the present invention include a number of growth factors, including epidermal growth factor (EDF), PDGF, and nerve growth factors (NGF's). Generally, growth-promoting hormones will affect between one and four tissues. Many of the products developed from such proteins are targeted towards wound repairs of one kind or another, although there are other indications. Some of the most important tissue growth factors are described further below.

The gel/nanostructure compositions of the invention may also include one or more growth factors that may be useful in the tissue repair methods and other applications of the invention.

For example, the invention contemplates include PDGF in the compositions of the invention. Platelet-Derived Growth Factor (PDGF) is a mitogen for almost all mesenchymally-derived cells, i.e. blood, muscle, bone, cartilage, and connective tissue cells. It is a dimeric glycoprotein existing as AA or BB homodimers, or as the AB heterodimer. As with many growth factors, PDGF is now considered to be a member of a larger family of factors. In addition to PDGF, this family includes the homodimeric factors vascular endothelial growth factor (VEGF) and placental growth factor (PlGF), VEGF/PlGF heterodimers, and connective tissue growth factor (CTGF), a PDGF-like factor secreted by human vascular endothelial cells and fibroblasts. Along with NGF, TGF-.beta. and glycoprotein hormones such as human chorionic gonadotropic hormone (hCG), PDGF is now classified as a member of the cysteine-knot growth factor superfamily. All of these factors may be used in conjunction with hydrogels of the present invention.

PDGF is produced by platelets and released in the course of blood clotting. It is just one of the growth factors that derive from these cells. PDGF attracts fibroblasts and white blood cells to the site of the injury, as well as stimulating the growth of replacement connective tissue (mainly fibroblasts and smooth muscle cells). It stimulates cell division in various cells, including those that produce collagen, so encouraging angiogenesis. It also stimulates mitogenesis, vasoconstriction, chemotaxis, enzyme activity and calcium mobilization.

Blood platelet derived growth factors may be used to restore bone and soft tissue regrowth during certain treatments using the compositions of the invention and to accelerate the healing process of chronic and acute wounds. Accordingly, hydrogel/nanostructure compositions of the present invention may advantageously comprise a platelet derived growth factor cocktail.

Hydrogel/nanostructure compositions of the present invention may be used in gene therapy for local delivery of the PDGF gene, for example. Plasmid DNA encoding PDGF is incorporated into the hydrogel matrix and granulation tissue fibroblasts, which originate in viable tissue surrounding the wound, proliferate and migrate into the matrix, acting as targets for plasmid gene transfer and expression.

The hydrogel/nanostructure compositions of the invention may also include VEGF to promote angiogenesis. Vascular Endothelial Growth Factor (VEGF—also known as vascular permeability factor) is another vascular growth factor, and is a multifunctional angiogenic cytokine. It contributes to angiogenesis (blood vessel growth) both indirectly and directly by stimulating proliferation of endothelial cells at the microvessel level, causing them to migrate and to alter their generic expression. VEGF also makes theses endothelial cells hyperpermeable, causing them to release plasma proteins outside the vascular space, which causes changes in the area, contributing to angiogenesis.

The compositions of the invention may also include FGF. Fibroblast Growth Factor (FGF) is actually a family of at least 19 14 18 kD peptides belonging to the heparin-binding growth factors family, and are mitogenic for cultured fibroblasts and vascular endothelial cells. They are also angiogenic in vivo and this angiogenicity is enhanced by TNF. FGF's may be used in a similar manner to EGF. bFGF, also known as FGF-2, is involved in controlling human megakaryocytopoiesis and FGFs have been shown to be effective in stimulating endothelial cell formation, and in assisting in connective tissue repair.

Hydrogel/nanostructure compositions may also comprise Keratinocyte Growth Factor (KGF), also known as FGF-7, for use in wound healing and other disorders involving epithelial cell destruction.

Transforming Growth Factors (TGF's) have the ability to transform various cell lines, and can confer, for example, the ability to grow in culture for more than a limited number of generations, growth in multiple layers rather than monolayers, and the acquisition of an abnormal karyotype. There are at least five members of the TGF family, the two most widely studied being TGF-alpha and TGF-beta. The former is mitogenic for fibroblasts and endothelial cells, angiogenic, and promotes bone resorption. Compositions also may include TGF. TGF-beta is a general mediator of cell regulation, a powerful inhibitor of cell growth, and inhibits the proliferation of many cell types. TGF-beta can antagonise the mitogenic effects of other peptide growth factors, and can also inhibit the growth of many tumour cell lines. TGF-beta also has angiogenic effects, and promotes collagen formation in fibroblasts. Indications for hydrogels of the present invention include chronic skin ulcers, such as neurotrophic foot ulcers in diabetic patients. Other areas include wound healing, bone repair and immunosuppressive diseases.

Hydrogel/nanostructure compositions of the present invention may be used to carry suitable cells, for example. These may be incorporated into the gel just prior to application to a wound, or other suitable area, to maximise efficacy. Suitable cells include autologous fibroblasts and keratinocytes, which are mainly responsible for dermis and epidermis formation. Separate gels each comprising one cell type may be applied consecutively or together, or one gel may comprise both cell types, but this is generally less preferred.

Hydrogel/nanostructure compositions of the present invention may usefully comprise collagen, for example. Although collagen, in this form, is unlikely to serve a useful structural function, it primarily serves as a sacrificial protein where proteolytic activity is undesirably high, thereby helping to prevent maceration of healthy tissue, for example.

Hydrogel/nanostructure compositions can also include certain enzymes. Enzymes are used in the debridement of both acute and chronic wounds. Debridement is the removal of nonviable tissue and foreign matter from a wound and is a naturally occurring event in the wound-repair process. During the inflammatory phase, neutrophils and macrophages digest and remove "used" platelets, cellular debris, and avascular injured tissue from the wound area. However, with the accumulation of significant amounts of damaged tissue, this natural process becomes overwhelmed and insufficient. Build-up of necrotic tissue then places considerable phagocytic demand on the wound and retards wound healing. Consequently, debridement of necrotic tissue is a particular objective of topical therapy and an important component of optimal wound management.

Enzymes, for example, may be incorporated into hydrogels of the present invention for topical application to provide a selective method of debridement. Suitable enzymes may be derived from various sources, such as krill, crab, papaya, bovine extract, and bacteria Commercially available, suitable enzymes include collagenase, papain/urea, and a fibrinolysin and deoxyribonuclease combination.

Enzymes for use in the present invention generally work in one of two ways: by directly digesting the components of slough (e.g., fibrin, bacteria, leukocytes, cell debris, serous exudate, DNA); or, by dissolving the collagen "anchors" that secure the avascular tissue to the underlying wound bed.

Hydrogels of the present invention may comprise Dakin's solution, if desired, generally to exert antimicrobial effects and odour control. As a debridement agent, Dakin's solution is non-selective because of its cytotoxic properties. Dakin's solution denatures protein, rendering it more easily removed from the wound. Loosening of the slough aids facilitates debridement by other methods. Hydrogels comprising Dakin's solution may be changed twice daily if the goal is debridement. Periwound skin protection should generally be provided with ointments, liquid skin barrier film dressings, or solid skin barrier wafers, for example.

The gel of the present invention may be delivered by any suitable method, such as via a syringe or bellows pack (single dose delivery systems) or a multidose system, such as a pressurised delivery system or delivery via a 'bag in the can' type system (such as that published in WO98/32675). An example of a bellows pack is shown in published UK design number 2082665.

As such, the present invention also extends to a single dose delivery system comprising a gel according to the present invention, for the treatment of wounds. The invention also extends to a pressurised delivery system comprising a gel according to the present invention, and a pressurised hydrogel according to the present invention in an aerosol container capable of forming a spray upon release of pressure therefrom. Use of such delivery means allows the gel to be delivered to areas on a patient which are otherwise difficult to reach by direct application, such as on the back of a patient when the patient is lying down.

In certain embodiment, it may be advantageous to render the hydrogel compositions of the invention electrically conductive for use in biomedical electrodes and other electrotherapy contexts, i.e., to attach an electrode or other electrically conductive member to the body surface. For example, the hydrogel composition may be used to attach a transcutaneous nerve stimulation electrode, an electrosurgical return electrode, or an EKG electrode to a patient's skin or mucosal tissue. These applications involve modification of the hydrogel composition so as to contain a conductive species. Suitable conductive species are ionically conductive electrolytes, particularly those that are normally used in the manufacture of conductive adhesives used for application to the skin or other body surface, and include ionizable inorganic salts, organic compounds, or combinations of both. Examples of ionically conductive electrolytes include, but are not limited to, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates. Preferred salts are potassium chloride, sodium chloride, magnesium sulfate, and magnesium acetate, and potassium chloride is most preferred for EKG applications. Although virtually any amount of electrolyte may be present in the adhesive compositions of the invention, it is preferable that any electrolyte present be at a concentration in the range of about 0.1 to about 15 wt. % of the hydrogel composition. The procedure described in U.S. Pat. No. 5,846,558 to Nielsen et al. for fabricating biomedical electrodes may be adapted for use with the hydrogel compositions of the invention, and the disclosure of that patent is incorporated by reference with respect to manufacturing details. Other suitable fabrication procedures may be used as well, as will be appreciated by those skilled in the art.

Crosslinking

For certain applications, particularly when high cohesive strength is desired, the polymers of the gel/hydrogels of the invention may be covalently crosslinked. The disclosure contemplates that crosslinking may be desired as between the polymers of the gel/hydrogel component, but also crosslinking may be desired as between the polymers of the gel/hydrogel and the nanostructure components of the composite materials of the invention. The invention contemplates any suitable means for crosslinking polymers to one another, and crosslinking the gel/hydrogel polymers with the nanostructure components of the invention. The gel/hydrogel polymers may be covalently crosslinked to other polymers or to the nanostructures, either intramolecularly or intermolecularly or through covalent bonds. In the former case, there are no covalent bonds linking the polymers to one another or to the nanostructures, while in the latter case, there are covalent crosslinks binding the polymers to one another or to the nanostructures. The crosslinks may be formed using any suitable means, including using heat, radiation, or a chemical curing (crosslinking) agent. The degree of crosslinking should be sufficient to eliminate or at least minimize cold flow under compression. Crosslinking also includes the use of a third molecule, a "cross-linker" utilized in the cross-linking process.

For thermal crosslinking, a free radical polymerization initiator is used, and can be any of the known free radical-generating initiators conventionally used in vinyl polymerization. Preferred initiators are organic peroxides and azo compounds, generally used in an amount from about 0.01 wt. % to 15 wt. %, preferably 0.05 wt. % to 10 wt. %, more preferably from about 0.1 wt. % to about 5% and most preferably from about 0.5 wt. % to about 4 wt. % of the polymerizable material. Suitable organic peroxides include dialkyl peroxides such as t-butyl peroxide and 2,2bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo compounds include azo bis (isobutyronitrile) and azo bis (2,4-dimethylvaleronitrile). The temperature for thermally crosslinking will depend on the actual components and may be readily deduced by one of ordinary skill in the art, but typically ranges from about 80 C. to about 200 C.

Crosslinking may also be accomplished with radiation, typically in the presence of a photoinitiator. The radiation may be ultraviolet, alpha, beta, gamma, electron beam, and x-ray radiation, although ultraviolet radiation is preferred. Useful photosensitizers are triplet sensitizers of the "hydrogen abstraction" type, and include benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylaceto-phenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthonse such as 2-isopropylthioxanthone, 2-chlorothioxanthone, 2,4 dimethyl thioxanone, 2,4 dichlorothioxanone, and 2,4-diethyl thioxanone, and acyl phosphine oxides. Radiation having a wavelength of 200 to 800 nm, preferably, 200 to 500 nm, is preferred for use herein, and low intensity ultraviolet light is sufficient to induce crosslinking in most cases. However, with photosensitizers of the hydrogen abstraction type, higher intensity UV exposure may be necessary to achieve sufficient crosslinking. Such exposure can be provided by a mercury lamp processor such as those available from PPG, Fusion, Xenon, and others. Crosslinking may also be induced by irradiating with gamma radiation or an electron beam. Appropriate irradiation parameters, i.e., the type and dose of radiation used to effect crosslinking, will be apparent to those skilled in the art.

Suitable chemical curing agents, also referred to as chemical cross-linking "promoters," include, without limitation, polymercaptans such as 2,2-dimercapto diethylether, dipentaerythritol hexa(3-mercaptopropionate), ethylene bis(3-mercaptoacetate), pentaerythritol tetra(3-mercaptopropionate), pentaerythritol tetrathioglycolate, polyethylene glycol dimercaptoacetate, polyethylene glycol di(3-mercaptopropionate), trimethylolethane tri(3-mercaptopropionate), trimethylolethane trithioglycolate, trimethylolpropane tri(3-mercaptopropionate), trimethylolpropane trithioglycolate, dithioethane, di- or trithiopropane and 1,6-hexane dithiol. The crosslinking promoter is added to the uncrosslinked hydrophilic polymer to promote covalent crosslinking thereof, or to a blend of the uncrosslinked hydrophilic polymer and the complementary oligomer, to provide crosslinking between the two components.

The polymers and/or nanostructures may also be crosslinked prior to admixture with the complementary oligomer. In such a case, it may be preferred to synthesize the polymer in crosslinked form, by admixing a monomeric precursor to the polymer with multifunctional comonomer and copolymerizing. Examples of monomeric precursors and corresponding polymeric products are as follows: N-vinyl amide precursors for a poly(N-vinyl amide) product; N-alkylacrylamides for a poly(N-alkylacrylamide) product; acrylic acid for a polyacrylic acid product; methacrylic acid for a polymethacrylic acid product; acrylonitrile for a poly(acrylonitrile) product; and N-vinyl pyrrolidone (NVP) for a poly(vinylpyrrolidone) (PVP) product. Polymerization may be carried out in bulk, in suspension, in solution, or in an emulsion. Solution polymerization is preferred, and polar organic solvents such as ethyl acetate and lower alkanols (e.g., ethanol, isopropyl alcohol, etc.) are particularly preferred. For preparation of hydrophilic vinyl polymers, synthesis will typically take place via a free radical polymerization process in the presence of a free radical initiator as described above. The multifunctional comonomer include, for example, bisacrylamide, acrylic or methacrylic esters of diols such as butanediol and hexanediol (1,6-hexane diol diacrylate is preferred), other acrylates such as pentaerythritol tetraacrylate, and 1,2-ethylene glycol diacrylate, and 1,12-dodecanediol diacrylate. Other useful multifunctional crosslinking monomers include oligomeric and polymeric multifunctional (meth)acrylates, e.g., poly(ethylene oxide) diacrylate or poly(ethylene oxide) dimethacrylate; polyvinylic crosslinking agents such as substituted and unsubstituted divinylbenzene; and difunctional urethane acrylates such as EBECRYL 270 and EBECRYL 230 (1500 weight average molecular weight and 5000 weight average molecular weight acrylated urethanes, respectively—both available from UCB of Smyrna, Ga.), and combinations thereof. If a chemical crosslinking agent is employed, the amount used will preferably be such that the weight ratio of crosslinking agent to hydrophilic polymer is in the range of about 1:100 to 1:5. To achieve a higher crosslink density, if desired, chemical crosslinking is combined with radiation curing.

Nanostructures

The nanostructure components of the invention may be in any suitable form including fibers, filaments, mesh sections, branched filaments or networks, sheets, or shaped particles. The nanostructures may also comprise any suitable chemical functional groups to facilitate the covalent or noncovalent crosslinking between the nanostructures and the polymers of the hydrogels of the invention. Method, techniques, and materials are well known in the art for making and functionalizing nanostructures.

In certain embodiments, microfabrication methods are used to make the nanostructures of the invention. In various embodiments, the disclosed devices can be assembled and/or manufactured using any suitable microfabrication technique. Such methods and techniques are widely known in the art.

Microfabrication processes that can be used in making the nanostructures disclosed herein include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, Introduction to Microelectronic Fabrication (Addison-Wesley Publishing Co., Reading, Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997). The selection of the material that is used as the mold determines how the surface is configured to form the branching structure.

For example, state of the art processes for fabrication of Micro Electro Mechanical Systems (MEMS) utilizing photolithographic processes and methods derived from the semiconductor industry may be used. More recently developed methods include "soft lithography" (Whitesides et al, Angew chem. Int ed, 37; 550-575, (1998)) and microfluidic tectonics (U.S. Pat. No. 6,488,872, Beebe et al., Nature; 404:588-59 (2000)). Reviews and other discussions of polymer microdevice fabrication include Madou, M. J. Fundamentals of Microfabrication: The Science of Miniaturization; 2nd ed.; CRC Press: Boca Raton, 1997; Becker, H., and Locascio, L. E. "Polymer microfluidic devices." Talanta, 56(2):267-287, 2002; Quake, S. R., and Scherer, A. "From micro- to nanofabrication with soft materials." Science, 290(5496):1536-1540, 2000; and Whitesides, G. M., and Stroock, A. D. "Flexible methods for microfluidics." Physics Today, 54(6):42-48, 2001, each of which are incorporated herein by reference.

The nanostructures of the invention may also be fabricated by electrostatic spinning (also referred to as electrospinning). The technique of electrospinning of liquids and/or solutions capable of forming fibers, is well known and has been described in a number of patents, such as, for example, U.S. Pat. Nos. 4,043,331 and 5,522,879. The process of electrospinning generally involves the introduction of a liquid into an electric field, so that the liquid is caused to produce fibers. These fibers are generally drawn to a conductor at an attractive electrical potential for collection. During the conversion of the liquid into fibers, the fibers harden and/or dry. This hardening and/or drying may be caused by cooling of the liquid, i.e., where the liquid is normally a solid at room temperature; by evaporation of a solvent, e.g., by dehydration (physically induced hardening); or by a curing mechanism (chemically induced hardening).

The process of electrostatic spinning has typically been directed toward the use of the fibers to create a mat or other non-woven material, as disclosed, for example, in U.S. Pat. No. 4,043,331. Nanofibers ranging from 50 nm to 5 micrometers in diameter can be electrospun into a nonwoven or an aligned nanofiber mesh. Due to the small fiber diameters, electrospun textiles inherently possess a very high surface area and a small pore size. These properties make electrospun fabrics potential candidates for a number of applications including: membranes, tissue scaffolding, and other biomedical applications.

Electrostatically spun fibers can be produced having very thin diameters. Parameters that influence the diameter, consistency, and uniformity of the electrospun fibers include the polymeric material and cross-linker concentration (loading) in the fiber-forming combination, the applied voltage, and needle collector distance. According to one embodiment of the present invention, a nanofiber has a diameter ranging from about 1 nm to about 100 .mu.m. In other embodiments, the nanofiber has a diameter in a range of about 1 nm to about 1000 nm. Further, the nanofiber may have an aspect ratio in a range of at least about 10 to about at least 100. It will be appreciated that, because of the very small diameter of the fibers, the fibers have a high surface area per unit of mass. This high surface area to mass ratio permits fiber-forming solutions or liquids to be transformed from liquid or solvated fiber-forming materials to solid nanofibers in fractions of a second.

The polymeric material used to form the nanofibers/nanostructures of the invention may be selected from any fiber forming material which is compatible with the cross-linking agents. Depending upon the intended application, the fiber-forming polymeric material may be hydrophilic, hydrophobic or amphiphilic. Additionally, the fiber-forming polymeric material may be a thermally responsive polymeric material.

Synthetic or natural, biodegradable or non-biodegradable polymers may form the nanofibers/nanostructures of the invention. A "synthetic polymer" refers to a polymer that is synthetically prepared and that includes non-naturally occurring monomeric units. For example, a synthetic polymer can include non-natural monomeric units such as acrylate or acrylamide units. Synthetic polymers are typically formed by traditional polymerization reactions, such as addition, condensation, or free-radical polymerizations. Synthetic polymers can also include those having natural monomeric units, such as naturally-occurring peptide, nucleotide, and saccharide monomeric units in combination with non-natural monomeric units (for example synthetic peptide, nucleotide, and saccharide derivatives). These types of synthetic polymers can be produced by standard synthetic techniques, such as by solid phase synthesis, or recombinantly, when allowed.

A "natural polymer" refers to a polymer that is either naturally, recombinantly, or synthetically prepared and that consists of naturally occurring monomeric units in the polymeric backbone. In some cases, the natural polymer may be modified, processed, derivatized, or otherwise treated to change the chemical and/or physical properties of the natural polymer. In these instances, the term "natural polymer" will be modified to reflect the change to the natural polymer (for example, a "derivatized natural polymer", or a "deglycosylated natural polymer").

Nanofiber materials, for example, may include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Exemplary materials within these generic classes include polyethylene, poly(.epsilon.-caprolactone), poly(lactate), poly(glycolate), polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinyl alcohol in various degrees of hydrolysis (87% to 99.5%) in crosslinked and non-crosslinked forms. Exemplary addition polymers tend to be glassy (a Tg greater than room temperature). This is the case for polyvinylchloride and polymethylmethacrylate, polystyrene polymer compositions, or alloys or low in crystallinity for polyvinylidene fluoride and polyvinyl alcohol materials.

In some embodiments of the invention the nanofiber/nanostructure materials are polyamide condensation polymers. In more specific embodiments, the polyamide condensation polymer is a nylon polymer. The term "nylon" is a generic name for all long chain synthetic polyamides. Another nylon can be made by the polycondensation of epsilon caprolactam in the presence of a small amount of water. This reaction forms a nylon-6 (made from a cyclic lactam—also known as epsilon-aminocaproic acid) that is a linear polyamide. Further, nylon copolymers are also contemplated. Copolymers can be made by combining various diamine compounds, various diacid compounds and various cyclic lactam structures in a reaction mixture and then forming the nylon with randomly positioned monomeric materials in a polyamide structure. For example, a nylon 6,6-6,10 material is a nylon manufactured from hexamethylene diamine and a C6 and a C10 blend of diacids. A nylon 6-6,6-6,10 is a nylon manufactured by copolymerization of epsilon aminocaproic acid, hexamethylene diamine and a blend of a C6 and a C10 diacid material.

Block copolymers can also be used as nanofiber materials. In preparing a composition for the preparation of nanofibers, a solvent system can be chosen such that both blocks are soluble in the solvent. One example is an ABA (styrene-EP-styrene) or AB (styrene-EP) polymer in methylene chloride solvent. Examples of such block copolymers are a Kraton-type of AB and ABA block polymers including styrene/butadiene and styrene/hydrogenated butadiene(ethylene propylene), a Pebax-type of epsilon-caprolactam/ethylene oxide and a Sympatex-type of polyester/ethylene oxide and polyurethanes of ethylene oxide and isocyanates.

Addition polymers such as polyvinylidene fluoride, syndiotactic polystyrene, copolymers of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, can be solution spun with relative ease because they are soluble at low pressures and temperatures. Highly crystalline polymer like polyethylene and polypropylene generally require higher temperature and high pressure solvents if they are to be solution spun.

Nanofibers can also be formed from polymeric compositions comprising two or more polymeric materials in polymer admixture, alloy format, or in a crosslinked chemically bonded structure. Two related polymer materials can be blended to provide the nanofiber with beneficial properties. For example, a high molecular weight polyvinylchloride can be blended with a low molecular weight polyvinylchloride. Similarly, a high molecular weight nylon material can be blended with a low molecular weight nylon material. Further, differing species of a general polymeric genus can be blended. For example, a high molecular weight styrene material can be blended with a low molecular weight, high impact polystyrene. A Nylon-6 material can be blended with a nylon copolymer such as a Nylon-6; 6,6; 6,10 copolymer. Further, a polyvinyl alcohol having a low degree of hydrolysis such as a 87% hydrolyzed polyvinyl alcohol can be blended with a fully or super hydrolyzed polyvinyl alcohol having a degree of hydrolysis between 98 and 99.9% and higher. All of these materials in admixture can be crosslinked using appropriate crosslinking mechanisms. Nylons can be crosslinked using crosslinking agents that are reactive with the nitrogen atom in the amide linkage. Polyvinyl alcohol materials can be crosslinked using hydroxyl reactive materials such as monoaldehydes, such as formaldehyde, ureas, melamine-formaldehyde resin and its analogues, boric acids, and other inorganic compounds, dialdehydes, diacids, urethanes, epoxies, and other known crosslinking agents. Crosslinking reagent reacts and forms covalent bonds between polymer chains to substantially improve molecular weight, chemical resistance, overall strength and resistance to mechanical degradation.

Biodegradable polymers can also be used in the preparation of the nanostructures of the invention. Examples of classes of synthetic polymers that have been studied as biodegradable materials include polyesters, polyamides, polyurethanes, polyorthoesters, polycaprolactone (PCL), polyiminocarbonates, aliphatic carbonates, polyphosphazenes, polyanhydrides, and copolymers thereof. Specific examples of biodegradable materials that can be used in connection with, for example, implantable medical devices include polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone). Blends of these polymers with other biodegradable polymers can also be used.

In some embodiments, the nanofibers are non-biodegradable polymers. Non-biodegradable refers to polymers that are generally not able to be non-enzymatically, hydrolytically or enzymatically degraded. For example, the non-biodegradable polymer is resistant to degradation that may be caused by proteases. Non-biodegradable polymers may include either natural or synthetic polymers.

The inclusion of cross-linking agents within the composition forming the nanofiber, allows the nanofiber to be compatible with a wide range of support surfaces. The cross-linking agents can be used alone or in combination with other materials to provide a desired surface characteristic.

Suitable cross-linking agents include either monomeric (small molecule materials) or polymeric materials having at least two latent reactive activatable groups that are capable of forming covalent bonds with other materials when subjected to a source of energy such as radiation, electrical or thermal energy. In general, latent reactive activatable groups are chemical entities that respond to specific applied external energy or stimuli to generate active species with resultant covalent bonding to an adjacent chemical structure. Latent reactive groups are those groups that retain their covalent bonds under storage conditions but that form covalent bonds with other molecules upon activation by an external energy source. In some embodiments, latent reactive groups form active species such as free radicals. These free radicals may include nitrenes, carbine or excited states of ketones upon absorption of externally applied electric, electrochemical or thermal energy. Various examples of known or commercially available latent reactive groups are reported in U.S. Pat. Nos. 4,973,493; 5,258,041; 5,563,056; 5,637,460; or 6,278,018.

For example, the commercially available multifunctional photocrosslinkers based on trichloromethyl triazine available either from Aldrich Chemicals, Produits Chimiques Auxiliaires et de Syntheses, (Longjumeau, France), Shin-Nakamara Chemical, Midori Chemicals Co., Ltd. or Panchim S. A. (France) can be used. The eight compounds include 2,4,6-tris(trichloromethyl)-1,3,5 triazine, 2-(methyl)-4,6-bis(trichloromethyl)-1,3,5-triazine, 2-(4-methoxynaphthyl)-4,6-bis(trichloromethyl)-1,3,5-triazine, 2-(4-ethoxynaphthyl)-4,6-bis(trichloromethyl)-1,3,5-triazine, 4-(4-carboxylphenyl)-2,6-bis(trichloromethyl)-1,3,5-triazine, 2-(4-methoxyphenyl)-4,6-bis(trichloromethyl)-1,3,5-triazine, 2-(1-ethen-2-2'-furyl)-4,6-bis(trichloromethyl)-1,3,5-triazine and 2-(4-methoxystyryl)-4,6-bis(trichloromethyl)-1,3,5-triazine.

Methods of Use and Exemplary Embodiments

The gel/hydrogel/nanostructure compositions of the invention can be used advantageously in numerous tissue repair situations, as well as in other applications, such as providing coatings on catheters and other surgical devices and implants. The gel/hydrogel/nanostructure compositions of the invention can also be used to deliver active agents described herein, such as antibiotics, growth factors, and immunosuppressive agents.

In certain embodiments, the invention provides a method for healing a soft tissue defect comprising applying a composite material to a soft tissue defect, wherein the composite material includes a gel and a nanostructure disposed within the gel.

It will be appreciated that advantageous properties of the hydrogels/nanostructure compositions described herein include the ability to: 1) provide easy characterization and quality control; 2) integrate with existing tissue matrices; 3) directly incorporate into newly formed matrices; 4) directly include cells and bioactive factors; 5) maintain biocompatibility; 6) control bioresorption; 7) cast easily into complicated anatomical shapes due to greater structural rigidity owing to the nanostructures; and 8) exhibit the mechanical properties of native tissues such as articular cartilage.

In one application, the hydrogel/nanostructure composite compositions of the invention can be used to repair cartilage tissue. Current biologically-based surgical procedures for cartilage repair include autologous chondrocyte implantation, drilling, abrasion chondroplasty, microfracture, and mosaic arthroplasty. All these procedures treat only focal articular cartilage injuries, and not cartilage denuded joint surfaces such as seen in severe osteoarthritis and rheumatoid arthritis. Also, they use either cartilage tissue plugs or expanded chondrocytes harvested from the patient to fill cartilage defects. These tissues or chondrocytes are expected to fill the defect by synthesizing entirely de novo material, such as newly synthesized hyaline cartilage, that has integrated with existing cartilage matrices and has the biomechanical properties of normal cartilage. However, such procedures all promote the formation of a reparative tissue (fibrocartilage) rather than true hyaline cartilage with further mechanical damage to fibrocartilage thought to predispose the joint to osteoarthritis. Furthermore, the availability of endogenous cartilage as a repair material is quite limited with its acquisition presenting its own risks and morbidity to the patient. As evident from the foregoing discussion, the resulting hydrogel/nanostructure compositions disclosed herein present practical materials for promising new therapies in patients suffering from cartilage degenerative diseases.

As described herein, the present hydrogel/nanostructure compositions can be prepared having widely varying properties that are suitable for any number of synthetic tissue implantation or augmentation, as well as other clinical applications. As already described, the present materials can be used to repair cartilage defects produced as a result of either injury or disease. Defects due to injury that can be so repaired can be sports- or accident-related, and may involve only the superficial cartilage layer, or may include the underlying subchondral bone. Defects due to disease which can be repaired using the compositions described herein include those resulting from osteoarthritis and rheumatoid arthritis. Whether from injury or disease, such defects may be in either mature or growth plate cartilage. Formulations for hydrogels for synthetic growth plate cartilage may require the inclusion of unsubstituted scaffold material to allow for controlled bioresorption of the biomaterial during growth.

Another field where the hydrogel/nanostructure compositions described herein can be useful is the repair, reconstruction or augmentation of cartilaginous as well as soft tissues of the head and neck. The availability of biomaterials for soft tissue augmentation and head and neck reconstruction has remained a fundamental challenge in the field of plastic and reconstructive surgery. Significant research and investment has been undertaken for the development of a material with appropriate biological compatibility and life span. The outcomes of this research have not been promising. When placed in immunocompetent animals the structural integrity of currently proposed materials has been shown to fail as the framework is absorbed. Furthermore, though conventional synthetic materials offer excellent lifespan, they present certain unavoidable pitfalls. For example, silicones have been fraught with concerns of safety and long-term immune related effects. Synthetic polymers PTFE (gortex) and silastic offer less tissue reactivity but do not offer tissue integration and can represent long term risks of foreign body infections and extrusion. The materials described in this application will be useful to prepare a synthetic soft-tissue scaffold material for the augmentation or repair of soft-tissue defects of the head and neck. In particular, the hydrogel/nanostructure compositions, which are non-inflammatory, non-immunogenic, and which can be prepared having the appropriate degree of viscoelasticity (see description herein), could be used as an effective implantable scaffold material.

In addition, the present hydrogel/nanostructure compositions can be used, for example, as a novel, biocompatible and biocompliant materials to prepare cartilage implants which are frequently used in reconstructive procedures of the head and neck to repair cartilaginous or bony defects secondary to trauma or congenital abnormalities. Applications specific to the ear include otoplasty and auricular reconstruction, which are often undertaken to repair cartilaginous defects due to trauma, neoplasm (i.e., squamous cell carcinoma, basal cell carcinoma, and melanoma), and congenital defects such as microtia. Applications specific to the nose include cosmetic and reconstructive procedures of the nose and nasal septum. Dorsal hump augmentation, tip, shield and spreader grafts are frequently used in cosmetic rhinoplasty. Nasal reconstruction following trauma, neoplasm, autoimmune diseases such as Wegeners granulomatosis, or congenital defects require cartilage for repair. Septal perforations are difficult to manage and often fail treatment. Cartilage grafts would be ideal for these applications, as autologous or donor cartilage is often unavailable. Applications specific to the throat include laryngotracheal reconstruction, which in children usually requires harvesting costal cartilage, which is not without morbidity. Auricular and septal cartilage is often inadequate for this application. Synthetic cartilaginous materials prepared from hydrogels disclosed herein can be synthesized to suit each of the foregoing applications, based on tuning parameters of hydrogel synthesis such as reagent concentration, substitution and cross-linking rates. Laryngotracheal reconstruction is usually performed for airway narrowing due to subglottic or tracheal stenosis. The etiology may be traumatic (i.e., intubation trauma, or tracheotomy) or idiopathic. Other possibilities include chin and cheek augmentation, and use in ectropion repair of the lower eyelid, in addition to numerous craniofacial applications. It should be noted that these applications may not need cartilage with the exacting mechanical properties of articular cartilage. Inclusion of a cell population or bioactive agents may also be desirable.

The hydrogel/nanostructure compositions described herein also can be used for repair and narrowing of the nasal cavity, normally following overly aggressive surgical resection, to prevent the chronic pooling of fluid in the nasal passages that leads to infection and encrustation. Another promising application is in laryngotracheal reconstruction in both children and adults, as a result of laryngotracheal injury due for example to intubation during a surgical procedure such as cardiovascular surgery. Hydrogel/nanostructure compositions as herein described also can be used to provide cricoid ring replacements to protect the carotid artery following neck resection for cancer—the composition of the invention can be placed between the carotid artery and the skin as a protective barrier for the carotid artery against loss of the skin barrier. As a protective coating during neuronal repopulation of a resected nerve—often fibrous tissue forms faster than the neuronal repopulation preventing its eventual formation. Placement of the nerve ends within a hydrogel/nanostructure composition of the invention pre-cast tube could exclude fibrous tissue formation from the site of repopulation.

The hydrogel/nanostructure compositions of the invention can also be used for repair of soft tissue defects of any internal or external organs. For example, the materials of the invention can be used to for chin and cheek augmentation, and use in ectropion repair of the lower eyelid, in addition to numerous craniofacial applications. For cosmetic and reconstructive purposes in sites other than the head and neck, for example use as breast implants for breast augmentation, as a wound sealant, for example to fill the void left after removal of lymph nodes (i.e. due to cancer) in the breast or neck, to seal the lymphatics and abate uncontrolled fluid drainage into the resection site that may lead to infection and other complications.

In addition to the above uses, the hydrogel/nanostructure compositions described herein can be used in other tissue engineering applications to produce synthetic orthopaedic tissues, including, but not limited to, bone, tendon, ligament, meniscus and intervertebral disc, using similar strategies and methodologies as described above for the synthesis of artificial forms of cartilage. The hydrogel/nanostructure compositions also can be used to make synthetic non-orthopaedic tissues including but not limited to vocal cord, vitreous, heart valves, liver, pancreas and kidney, using similar strategies and methodologies as described above for the synthesis of artificial forms of cartilage.

Another field where the hydrogel/nanostructure compositions disclosed herein can be used is in gastrointestinal applications where it is necessary to treat or prevent the formation of scar tissue or strictures in abdominal or gastrointestinal organs. There already are a number of products at various stages of clinical and FDA approval, which generally are termed "hydrogels," that are designed or intended to be useful in the treatment and prevention of scarring and/or stricture formation. The materials of the present invention are superior to other known hydrogels in that the ones disclosed here can include a nanostructure which can provide support, shape, and strength to hydrogel materials. The hydrogel/nanostructure compositions disclosed herein can be used in similar applications as the already known hydrogels are used or intended to be used, including the following: for treatment of strictures or scarring of the gastrointestinal tract. The treatment involves injection of the hydrogel material at the site of an anticipated stricture to prevent scarring, or at a site of existing stricture after therapy to enlarge the narrowed GI tract to prevent the stricture from reoccurring.

The materials of the invention can also be used for the treatment of esophageal strictures. Esophageal strictures are a common complication of gastroesophageal reflux disease (GERD). GERD is caused by acid, bile and other injurious gastric contents refluxing into the esophagus and injuring the esophageal lining cells. Approximately 7-23% of GERD patients develop an esophageal stricture, or fibrous scarring of the esophagus. Esophageal scarring also can be caused by ablative therapies used to treat Barrett's esophagus. The major complication of such ablative therapies is that the ablative injury extends too deeply into the esophageal wall and results in an esophageal scar or stricture. Esophageal strictures prevent normal swallowing and are a major cause of patient morbidity. The materials described herein may be used to treat or prevent esophageal strictures resulting from GERD, Barrett's esophagus, and esophageal ablative therapies.

The composite materials of the invention may also be used for treatment of Crohn's disease. Crohn's disease causes strictures or scars that block off or narrow the lumen of the bowel, preventing normal bowel function. The present materials may be useful to treat or prevent such strictures.

The composite materials can also be used in methods for treating primary sclerosing cholangitis (PSC). PSC is a rare disease of the bile ducts of the liver. The bile ducts form a branching network within the liver and exit the liver via two main branches that are combined into the common bile duct which drains the liver and gallbladder of bile into the duodenum. The bile ducts are very narrow in diameter, measuring only up to 2 mm normally at their largest most distal portions, and yet they must normally drain liters of bile every day from the liver into the duodenum. Any blockage of these ducts can result in a serious condition known as jaundice, which allows many toxins and especially hemoglobin breakdown products to accumulate in the body. PSC is a scarring or structuring disease of the bile ducts within the liver and in the extrahepatic bile ducts described above that connect the liver to the small intestine. The bile duct strictures of PSC may be treated or prevented with the present hydrogel/nanostructure compositions.

The composite materials of the invention can also be used to treat chronic pancreatitis. Chronic pancreatitis is a chronic inflammatory disease of the pancreas that may be complicated by scars or strictures of the pancreatic ducts. These strictures block the drainage of pancreatic juice, which normally must exit the pancreas through a system of ducts or drainage conduits into the small intestine. The pancreatic juice contains many digestive enzymes and other elements important to normal digestion and nutrient absorption. Blockage or narrowing of the pancreatic ducts by chronic pancreatitis can results in severe complications in which the pancreas autodigests and forms life-threatening abdominal infections and or abscesses. The pancreatic strictures of chronic pancreatitis may be treated or prevented with the present hydrogels.

The presently described compositions may also be used for treatment of gallstone-induced bile duct and pancreatic duct strictures. Gallstones are a very common disorder, a principal complication of which is the formation of bile duct and pancreatic duct strictures, which may be treated or prevented with the hydrogels. for treatment of ischemic bowel disease. The intestines are prone to the formation of scars or strictures when their blood supply is compromised. Compromised blood flow is called ischemia, and can be caused by many pathologies, including cardiovascular disease, atherosclerosis, hypotension, hypovolemia, renal or hepatic disease-induced hypoalbuminemia, vasculitis, drug-induced disease, and many others. The end stage result of all of these etiologies can result in intestinal strictures that block off the bowel and prevent its normal function. The present hydrogel/nanostructure composites may be used to treat or prevent ischemic bowel strictures.

The compositions of the invention may also be used for treatment of radiation-induced intestinal strictures. Radiation therapy for cancer is associated with numerous morbidities, important among which is intestinal stricture formation. The present hydrogel composites may be used to treat or prevent radiation-induced intestinal strictures.

In addition to making synthetic tissues or repairing native tissues, the hydrogel/nanostructure composites disclosed here also can be used to provide a coating for non-biological structures or devices to be used in surgery or otherwise for in vivo implantation, such as surgical instruments, or ceramic or metal prostheses. Such a coating would provide a barrier between the non-biologic device material and living tissue. The role of hydrogels as a barrier for non-biologic devices includes, but is not limited to: 1) prevention of absorption of macromolecules and/or cells on the surfaces of non-biologic devices, which can lead to protein fouling or thrombosis at the device surface; 2) presentation of a non-toxic, non-inflammatory, non-immunogenic, biologically compatible surface for devices made from otherwise non-biologically compatible materials; 3) compatibility with device function such as diffusion of glucose for a glucose sensor, transmission of mechanical force for a pressure sensor, or endothelization of a vascular graft or stent; 4) enhancement of device function, such as providing a charge barrier to an existing size barrier in a MEMS based artificial nephron; 5) incorporation into non-biologic devices of a viable cell population entrapped within an aqueous, physiologically compatible environment; and 6) inclusion of drugs or bioactive factors such as growth factors, anti-viral agents, antibiotics, or adhesion molecules designed to encourage vascularization, epithelization or endothelization of the device.

Based on the foregoing, the hydrogel/nanostructure composites of the present invention may be used to provide a non-allergenic coating for a variety of implantable devices including an implantable glucose sensor for management of diabetes. In addition, the hydrogel/nanostructure composites may be used to provide: a charge barrier for the development of MEMS-based artificial nephrons; an aqueous, physiologically compatible environment in which embedded kidney cells such as podocytes can be incorporated into a MEMS-based artificial nephron design; and a coating for implantable MEMS devices designed for a variety of purposes including, but not limited to, drug delivery, mechanical sensing, and as a bio-detection system.

The disclosed hydrogel/nanostructure composites, and particularly a hyaluronan-based hydrogel, also may be covalently attached to silicon-based devices, e.g. through first covalent attachment of the primary amine of tyramine to the silicon surface to provide a hydroxyphenyl coated surface chemistry. This may use the same chemistry used to bind DNA that has been modified with a free amine to silicon surfaces. The HA-based hydrogel then is covalently coupled to the hydroxyphenyl coated surface by the same peroxidase driven chemistry used in its preferred cross-linking mode described above.

The hydrogel/nanostructure composites also can be used for coating non-biologic cardiovascular devices such as catheters, stents and vascular grafts. These would include devices made from materials conventionally not used because of their biological incompatibility, but which have superior design characteristics to those devices currently in use. Bioactive factors could be incorporated into the hydrogels to promote endothelization or epithelization of the hydrogel, and thus of the implanted device.

Although particular examples and uses for the hydrogel/nanostructure composites of the invention have been described herein, such specific uses are not meant to be limiting. The hydrogel/nanostructure composites of the invention can be used for any application generally used for known hydrogels, and in particular, are useful for the repair and/or regeneration of soft tissue anywhere in the body.

Reference will now be made to the drawings wherein like reference numerals identify similar structural features or aspects of the subject disclosure. For purposes of explanation and illustration, and not limitation, an illustrative view of an embodiment of a biodegradable composite in accordance with the disclosure is shown in FIG. 1A and is designated generally by reference character 100. The systems and methods described herein can be used to enhance healing of soft tissue defects.

Referring generally to FIGS. 1A-1D, the biodegradable composite 100 can include a nanofiber 101 reinforced gel 103 that combines the advantages of both gel 103 and nanofibers 101. The gel 103 can include any suitable material, such as, but not limited to, hydrogel. The nanofibers 101 can be made of any suitable nanomaterial, e.g., polycaprolactone (PCL) or any other suitable material, and can take any suitable shape and/or size. The composite 100 includes high porosity (e.g., to mediate cell adhesion and migration) while maintaining sufficient mechanical properties (e.g., to maintain integrity and tissue support).

In at least some embodiments, the nanofibers 101 are covalently conjugated to the hydrogel 103 forming one or more polymer chains. Covalent attachment of hydrogels 103 to the nanofibers 101 can result in a material with a combined set of ideal properties superior to the constituent materials used alone or as a simple blend.

Figure 1B:
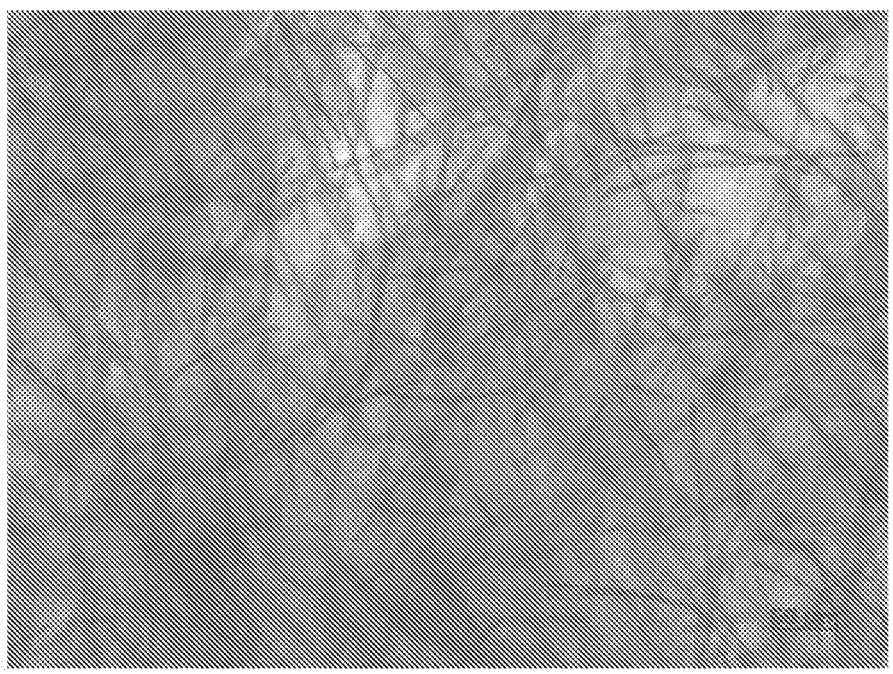
FIG. 1B shows a light microscope image of a fully swollen composite.
Figure 1C:
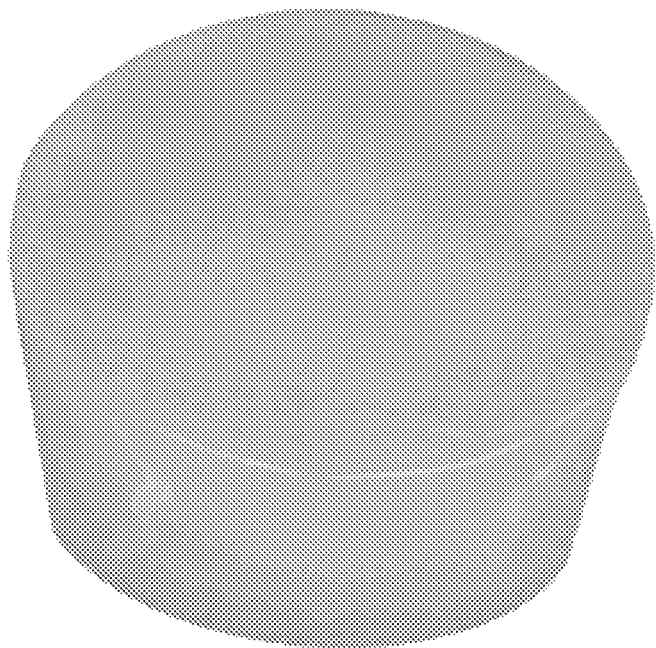
FIG. 1C is an image of the macroscopic appearance of a hydrated composite.
Figure 1D:
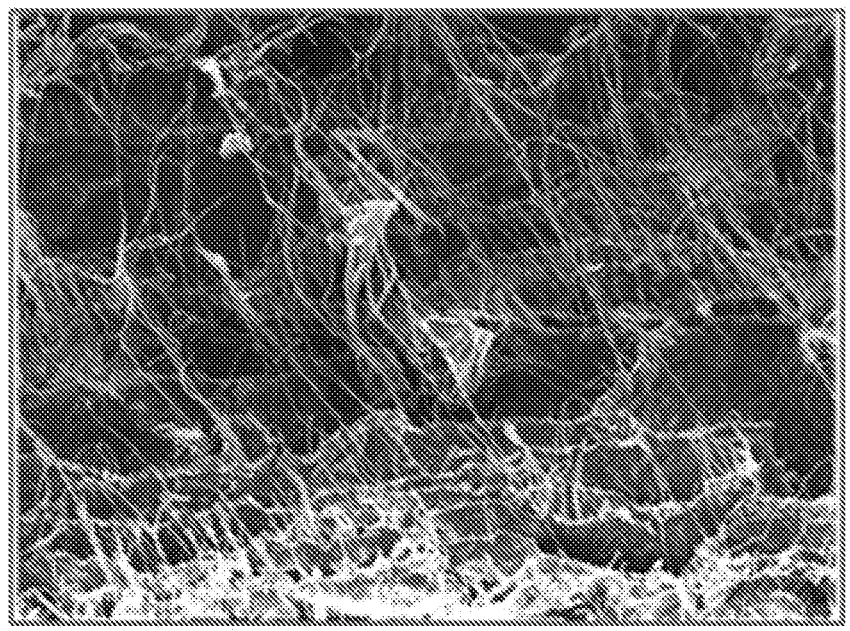
FIG. 1D shows a scanning electron micrography (SEM) image of a dehydrated composite, revealing ultra-structural similarity to the ECM of fat tissue.
Figure 2A:
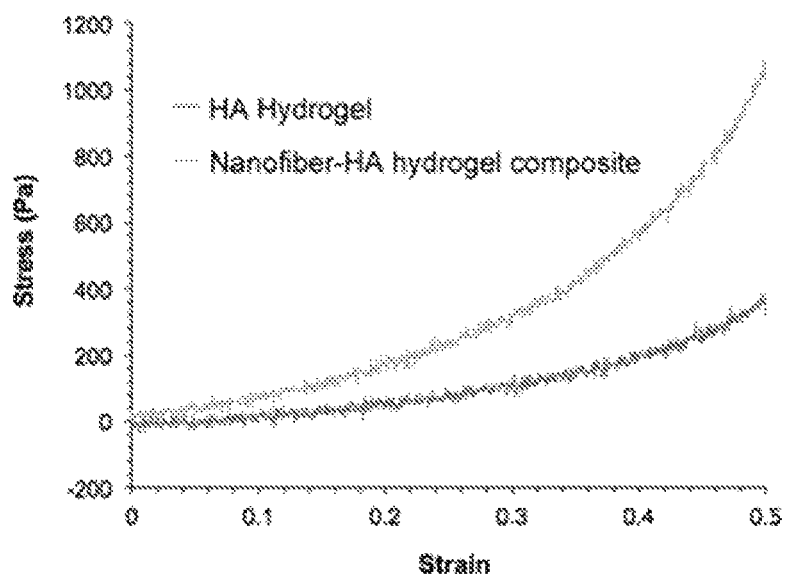
FIG. 2A depicts stress-strain curves of an embodiment of the composite of FIGS. 1A-1C plotted against HA hydrogel alone, revealing improved elastic modulus compared to hydrogel at the same crosslinking density.
Figure 2B:
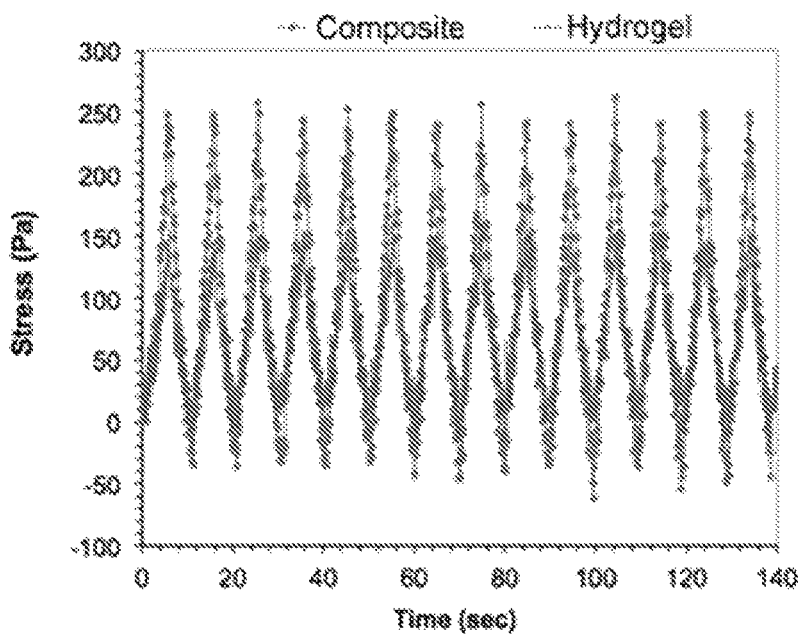
FIG. 2B depicts a fatigue test showing that the embodiment of a composite of FIG. 2A retains similar degree of robustness of mechanical integrity compared to regular hydrogel.

FIG. 2A depicts stress-strain curves of an embodiment of the composite of FIG. 1 plotted against HA Hydrogel alone, revealing improved elastic modulus compared to hydrogel at the same crosslinking density. As shown, the elastic modulus of the tested composite 100 (4.5 mg/ml HA, 10 mg/ml PEG-DA, 6.75 mg/ml PCL fibers) was 750 Pa, and hydrogel alone at the same density was 320 Pa. FIG. 2B depicts a fatigue test showing that the composite as illustrated in FIG. 1 retains similar degree of robustness of mechanical integrity compared to regular hydrogel Referring to FIG. 3A-3B, the composite 100 was shown to support adipose-tissue derived stem cell (ASC) migration. GFP-labelled ASCs from liposuction aspirates were grown into spheroids and then seeded into composite or hydrogel.

Figure 3A:
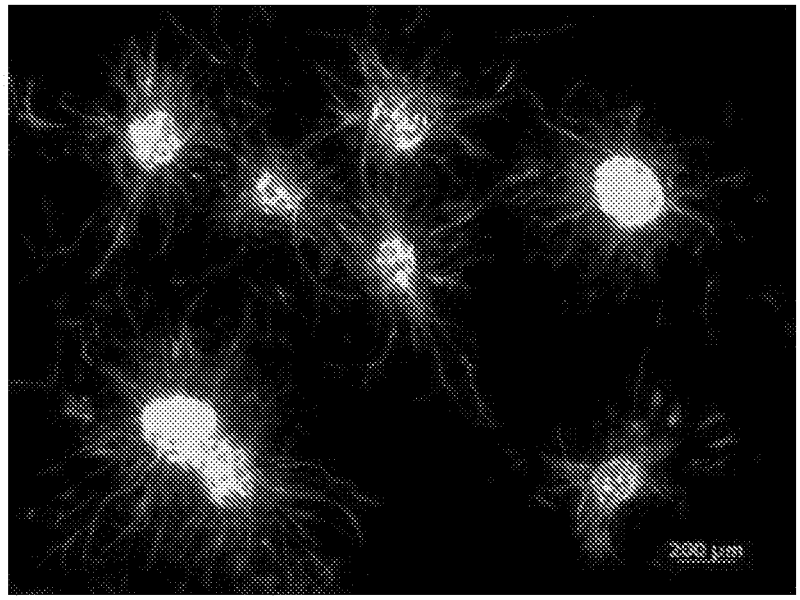
FIGS. 3A and 3B show a fluorescence image (FIG. 3A) and an overlay with the phase contrast image (FIG. 3B) of ASCs cultured in nanofiber-HA hydrogel composite for 4 days.
Figure 3B:
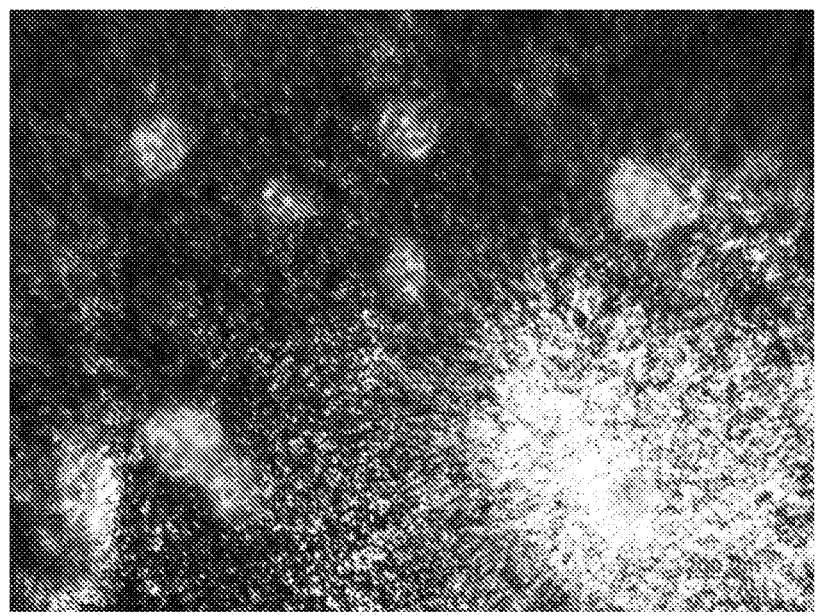

FIGS. 3A and 3B show fluorescence and overlay (FIG. 3A) with phase contrast images (FIG. 3B) of ASCs cultured in nanofiber-HA hydrogel composite for 4 days. The cells migrated outwards with extended long processes and trajectories. In contrast, ASCs cultured in HA hydrogel alone shown in FIGS. 3C and 3D did not show significant cell migration.

Figure 4A:
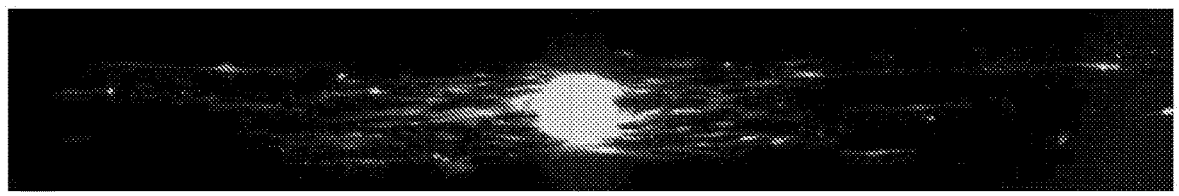
FIGS. 4A and 4B show a fluorescence image (FIG. 4A) and an overlay with the phase contrast image (FIG. 4B) contrasting ASCs migrating from spheroids along aligned 650-nm nanofibers.
Figure 4B:
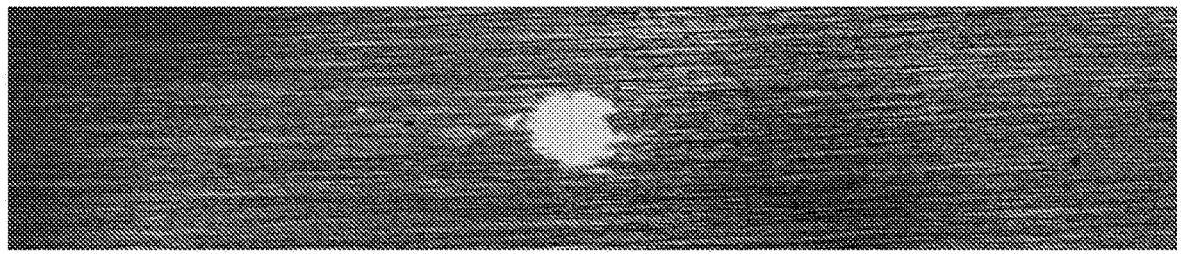

FIGS. 4A and 4B show a fluorescence image and overlay (FIG. 4A) with phase contrast image (FIG. 4B) contrasting ASCs migrating from spheroids along aligned 650-nm nanofibers 101, showing their strong migratory response to the presence of nanofibers 101.

Example 1: Preparation of Nanofiber-Hydrogel Composite

Nanofibers were produced by electrospinning PCL (polycaprolactone, 80 k from Sigma Aldrich). The nanofibers were spun into a random mesh. The spinning parameters were a 10% wt solution of PCL in 90%/1% w/w DCM-DMF, at a flowrate of 0.6 ml/hr through a 27 gauge blunt needle 15 cm from the target metal plate. The needle voltage was +10 kV, with the target plate was negatively biased with a voltage of −3 kV. 1 mL of solution was spun per round.

The fibers are then functionalized with a multistep process. Briefly, the fibers are plasma-treated to have reactive groups on the fiber surface, to which acrylic acid is conjugated by UV photoinitiation. The acrylate groups are then reacted with EDC and diazimine to form primary amines.

These amines can then be reacted with SMCC to attach maleimide groups, which can readily react with the thiol groups in the hydrogel.

The functionalized-fiber mesh was cut into sections of 60 mg or less. A 60 mg sample is soaked in ethanol, and then added to the ceramic mortar that has been partially filled with liquid nitrogen. The fiber sample will become very rigid. Keeping the sample cool enough to maintain rigidity, the fiber sheet is cut into ~5 mm×5 mm sections with scissors. When the full sheet has been cut, the fibers are ground with the mortar and pestle for ~20 min, keeping the mortar partially full with liquid nitrogen. The fiber slurry is then poured into ethanol. ~1 mg of surfactant is added to the slurry to help prevent fiber entanglement. The suspension is centrifuged for min at 300 G, and the supernatant is discarded. The fibers are allowed to dry overnight. The fibers are then weighed into a secondary centrifuge tube, so that a precise concentration of fibers can be suspended. The fibers are then soaked in ethanol to sterilize, centrifuged, had the supernatant discarded, and allowed to dry overnight in a biosafety cabinet. The fibers are then resuspended to the desired concentration in deionized water, usually 15 mg/mL.

To form the hydrogel composite, 1 ml of the fiber-suspension is used to rehydrate 1 vial of Glycosil hyaluronic acid, resulting in a solution of 15 mg/mL fibers and 10 mg/mL of hyaluronic acid. To 900 μL of this solution, 100 μL of 10% PEG-DA stock solution is added, to give a final concentration of 13.6 mg/mL fiber, 9 mg/mL Hyaluronic acid, and 10 mg/mL PEG-DA. This is the formulation for the initial in vivo examples, but other formulations have been made by varying the constituent concentrations.

The resulting composites were milky white in color (FIG. 1C), as opposed to the transparent hydrogels without the fibers. The composite gels maintained their shape and had good handleability, while the hydrogel-alone group was more prone to tearing. The fibers in the hydrogel were disperse and ranged in length from tens to hundreds of microns (FIG. 1B). A SEM image of cross-section of a fractured, lyophilized sample composite shows the close association between the fibers and hydrogel component, as well as the high density of dispersed fibers (FIG. 1D).

Materials and Methods

Materials

Thiolated hyaluronic acid (HA) was purchased from ESI BIO (Alameda, Calif.). Poly(ethylene glycol) diacrylates was purchased from Laysan Bio, Inc (Arab, Ala.). The followings were obtained from Sigma; poly(e-caprolactone), ethylamino-maleimide, acrylic acid, Toluidine blue O, N-hydroxysuccinimide (NHS), cysteine, bovine serum albumin (BSA), acetic acid and Triton™ X-100. Dulbecco's modified eagle medium (DMEM), fetal bovine serum (FBS), penicillin/streptomycin, Alexa Fluor® 568 Phalloidin and 4',6-diamidino-2-phenylindole (DAPI) were purchased from Invitrogen Life Technologies. Ethyl(dimethylaminopropyl) carbodiimide (EDC) was obtained from AnaSpec, Inc. (Fremont, Calif.). All other chemicals and reagents were of analytical grades.

Methods

Electrospinning of PCL Nanofibers for Rheology Experiments:

To fabricate two different diameters of PCL fibers, 11.0 and 8.5% (w/v) PCL solution were prepared in a mixture of dichloromethane and dimethylformamide (9:1, v/v) and a mixture of chloroform and methanol (3:1, v/v), respectively. Each homogenous PCL solution was loaded a syringe with a metallic needle of 27 G. Then, electrospinning was performed with following parameters; 1.0 ml/h of a feeding rate, 15 kV of an applied positive voltage for a metallic needle, and 12 cm of a distance between the end of a needle to a ground. Morphology of fibers was observed using a field-emission scanning electron microscope (FESEM, JEOL 6700F) and a diameter of fibers was measured with FESEM images using ImageJ software (US National Institutes of Health, Bethesda, Md.).

Electrospinning for In Vivo Composites:

Spinning conditions: 16% w/v PCL (95% 45.000 Mn PCL, 5% 80,000 Mn PCL, both from Sigma) in a solvent mixture of dichloromethane and dimethylformamide (9:1, w/w). The fibers were spun at a rate of 5.25 ml/hr through a blunt 27 gauge needle separated 10 cm from the face of the grounded wheel, spinning at 1000 rpm. The applied voltage was 15 kV and the electrospinning pump was rastered back and forth across the 85 mm travel distance for 140 passes at 2 mm/sec (about 4 hours). The fiber sheet was then cut into 14 cm-diameter individual sheets for functionalization.

Preparation of Surface-Functionalized Fibers with MAL:

To surface-functionalize on fibers with MAL, a surface of fibers was induced carboxyl groups by grafting poly(acrylic acid) (PAA) according to the literature with a minor modification [Interface Focus 2011, 1, 725-733]. Briefly, fibers were plasma-treated under 280 mmHg with oxygen atmosphere at room temperature for 10 min to induce free radicals on a surface of fibers. Then 70 mg of fibers in 10 ml of 3 or 10% (v/v) acrylic acid solution in 0.5 mM NaIO3 was exposed to UV (36 mW/cm$^2$, DYMAX Light Curing Systems 5000 Flood, Torrington, Conn.) for 90 s for photo-polymerization of PAA on fibers surface (PAA-fibers). After incubating PAA-fibers at room temperature for 20 min, PAA-fibers were washed with 20 ml of deionized water three times to remove unreacted acrylic acid. After completely air-drying PAA-fibers, a density of carboxyl groups on PAA-fibers were determined by toluidine blue 0 (TBO) assay with the assumption that TBO interacts with a carboxyl group on fibers at 1:1 of molar ratio [J Biomed Mater Res 2003, 67, 1093-1104]. Briefly, PAA-fibers (1×1 cm$^2$) were completely immersed in 1 ml of 0.5 mM TBO solution in 0.1 mM of NaOH (pH 10) after soaking 20 μl of 50% (v/v) ethanol and reacted with gentle shaking at room temperature for 5 h. After washing them with 0.1 mM NaOH (pH 10), adsorbed TBO on a surface of PAA-fibers was desorbed using 1 ml of 50% (v/v) acetic acid with vigorous shaking at room temperature for 1 h. Then an optical density of supernatant was measured at 633 nm using a microplate reader (BioTeck Synergy2, Winooski, Vt.). TBO in 50% (v/v) acetic acid was used as a standard.

PAA-fibers were ground to prepare fiber fragments using a cryogenic mill (Freezer/Mill 6770, SPEX SamplePrep, Metuchen, N.J.) with following parameters; 10 cycles of 1 min for milling and 3 min for cooling in liquid nitrogen. After collecting PAA-fiber fragments into a 50-ml conical tube, PAA-fiber fragments were completely dispersed in 10 ml of a mixture of isopropylacohol and distilled water (1:1, v/v) to modify with aminoethyl-MAL on a surface of fibers. Briefly, PAA-fibers were added NHS and EDC to activate carboxyl groups of PAA on fibers. A molar ratio of carboxyl group to NHS and EDC was 1 to 4 and 4, respectively. The activation was performed with gently shaking at room temperature. After 1 h, aminoethyl-MAL was added into the carboxyl groups-activated fibers with 1 to 2 of molar ratio of carboxyl groups to aminoethyl-MAL. Then the reaction was performed with gently shaking at room temperature for 12 h. Surface-functionalized fibers with MAL were lyophilized after washing with distilled water three times. Here, a density of MAL on fibers was on the assumption that all of carboxyl groups on a surface of fibers were completely substituted by MAL.

Preparation of Fiber-HA Hydrogel Composites:

For preparing a fiber-HA hydrogel composite, thiolated HA and PEGDA were completely dissolved in PBS (pH 7.4) to the desired concentration of 12.5 mg/mL and 100 mg/mL, respectively. MAL-fibers with the desired concentration of 25 mg/mL were completely dispersed in PBS (pH 7.4). The suspension of nanofibers, HA, PEG-DA, and PBS are then serially added to reach the formulation's desired final concentration. After homogenous mixing the composite precursor solution, for rheological studies, 100 µL of the composite precursor solution was poured into a mold (4)=8 mm) and incubated at 37° C. for 2 h for gelation. For compression studies, 200 µL of precursor solution is added to a cylindrical Teflon mold (4)=6.35 mm, h=6.35 mm) and incubated as above. To observe morphology of cross-section of a fiber-HA hydrogel composite and HA hydrogel using FESEM, a composite and HA hydrogel were dehydrated by serial ethanol washing (10 min each at 50%, 70%, 80%, 90%, 100%, and 100% Ethanol) before either critical point drying (Samdri-795, Tousimis, Rockvillle, Md.) or chemical drying (HDMS). The samples were freeze-fractured in liquid nitrogen to reveal the internal pore structure. The structure was sputter coated with a 10-nm layer of platinum (Hummer 6.2 Sputter System, Anatech UDA, Hayward, Calif.), then imaged with a field-emission SEM (JEOL 6700F, Tokyo Japan).

For preparation of the composites for the in vivo animal studies. the thiolated HA was reconstituted to 12.5 mg/mL in PBS. The PEG-DA was dissolved to 100 mg/mL in PBS. The MAL-fibers were resuspended to 25 mg/mL in sterile PBS. The fibers were first combined with the HA solution and allowed to react for 10 min before being combined with the PEG-DA to obtain the desired final concentrations. The suspension was then immediately pipetted into the cylindrical Teflon molds (McMaster-Carr, Robbinsville, N.J.), with 300 µL into cylindrical molds 11.125 mm in diameter and 3 mm in height for the in vivo samples. The gels were then placed into the 37° C. incubator to gel overnight.

To confirm the effect of interfacial bonding between thiol groups of HA and MAL on fibers, MAL on fibers was quenched using cysteine for preparing a quenched fiber-HA hydrogel composite. Briefly, 1 mg of fibers was dispersed in 1 ml of cysteine solution in PBS (pH 8.0) then a molar ratio of MAL to cysteine was 1 to 2. After quenching the MAL with gentle shaking at room temperature for 12 h, MAL-quenched fibers were washed with 1 ml of distilled water five times to remove unreacted cysteine and lyophilized.

Mechanical Properties of Fibers-HA Hydrogel Composites:

Compressive test. The hydrogel precursor suspension was pipetted into the cylindrical Teflon molds (McMaster-Carr, Robbinsville, N.J.), with 200 µL into cylindrical molds 6.35 mm in diameter and 6.35 mm in height for compression testing. The gels were then placed into the 37° C. incubator to gel overnight. The gels were removed from their molds and immediately tested via unconfined uniaxial compression between two parallel plates with the Endura TEC mechanical tester ELF 3200 Series, BOSE ElectroForce, Eden Prairie, Minn.). The samples were compressed to 50% strain, with the elastic modulus determined from the slope of the linear portion of the stress-strain curve from 10% to 20% strain. The samples were tested three times each, and three samples were tested per group for determining the average compressive modulus. To measure compressive modulus of rehydrated fiber-HA hydrogel composites, the composites were lyophilized and rehydrated with 1 ml of PBS (pH 7.4) at 37° C. for 24 h. For fatigue-testing, the compression samples were repeatedly cycled from 0% to 25% strain at 0.1 Hz.

Rheological test. Shear storage modulus (G') of various fiber-HA composites were measured using an oscillating rheometer (ARES-G2 Rheometer, TA Instruments, New Castle, Del.) with a parallel plate (4=8 mm). Oscillatory frequency sweep was employed to monitor variation of G' from 1 Hz to 10 Hz with constant strain of 10%.

Migration of hASCs in Fiber-HA Hydrogel Composites:

Human adipose-derived stem cells (hASCs) were cultured in high glucose DMEM containing 10% of FBS, 1% of penicillin/streptomycin, and 1 ng/ml of bFGF. The culture medium was exchanged three times per a week for optimal growth. To prepare hASC spheroids, 50 µl of hASCs solution ($5.6 \times 10^5$ cells/ml) was poured into a casted micromolded agarose gel (MicroTissues® 3D Petri Dish® micromold spheroids, 96-holes) to prepare hASCs spheroids and incubated with gently shaking at 37° C. for 24 h.

HA and PEGDA were completely dissolved in PBS (pH 7.4) with final concentration of 4.5 and 2.5 mg/ml for HA and 5.0 mg/ml for PEGDA. Fibers pre-wetted with 20 µl of 50% (v/v) ethanol were completely dispersed in PEGDA with final concentration of 10.0 mg/ml, then HA added into a mixture of fibers and PEGDA. 30 µl of composite precursor solution was poured into each well of a 96-well tissue culture plate and incubated to crosslink at 37° C. for 1 h for avoiding to reach hASCs spheroids on a surface of tissue culture plate. Then, 50 µl of composite precursor solution with 3~5 of hASCs spheroids was poured into the each well. After crosslinking at 37° C. for 1 h, 200 µl of fresh media were added into the each well and the media were exchanged every a couple of days. To observe migrated cells from hASCs spheroids inside the composites, F-actin and nuclei of hASCs were stained with Alexa Flour® 568 Phalloidin and DAPI, respectively. Briefly, after 4 days of cultivation, the composites with hASCs spheroids were fixed with 100 µl of 4% (v/v) paraformamide at room temperature for overnight. Then, after washing three times with PBS (pH 7.4), the composites were incubated with 100 µl of 1% (w/v) BSA in PBS to inhibit non-specific staining at 4° C. for overnight and washed three times with PBS. Subsequently, the composites were incubated with 100 µl of 0.1% (v/v) Triton-X 100 in PBS at room temperature for 1 h. After washing three times with PBS, 100 µl of 160 nM Alexa Fluor® 568 Phalloidin was added into each composites and incubated at room temperature for 4 h. Then, after removing the supernatant, the composites were incubated with 100 µl of 0.5 µg/ml DAPI at room temperature for 1 h. After washing three times with PBS, the migrated hASCs were observed using confocal laser scanning microscope (CLSM, Carl Zeiss LSM780, Germany) at ex. 561 nm and em. 570-600 nm for Alexa Fluor® 568 Phalloidin, and ex. 405 nm and em. 385-420 nm for DAPI.

Performance of a Fiber-Hydrogel Composite In Vivo:

The thiolated HA was reconstituted to 12.5 mg/mL in PBS. The PEG-DA was dissolved to 100 mg/mL in PBS. The MAL-fibers were resuspended to 25 mg/mL in sterile PBS. The fibers were first combined with the HA solution and allowed to react for 10 min before being combined with the PEG-DA to obtain the desired final concentrations. The suspension was then immediately pipetted into the cylindrical Teflon molds (McMaster-Carr, Robbinsville, N.J.), with 300 µL into cylindrical molds 11.125 mm in diameter and 3 mm in height. The gels were then placed into the 37° C.

incubator to gel overnight. The two formulations were selected so as to match the 2 kPa stiffness of fat tissue. The HA-alone formulation was 10 mg/mL PEG-DA and 9 mg/mL HA-SH, and the HA-fiber composite formulation was 5 mg/mL PEG-DA, 5 mg/mL HA-SH, and 12.5 mg/mL dispersed nanofibers.

To study the biocompatibility of the composite nanomaterial scaffolds, they were implanted under the inguinal fat pads of Sprague-Dawley rats and observed for varying lengths of time. Under volatile anesthesia, a 1 cm incision was made just proximal to the inguinal crease bilaterally. Following blunt dissection of subcutaneous tissues, the inguinal fat pad was exposed. It was elevated with meticulous hemostasis using electrocautery and with careful preservation of feeding vessels. Scaffolds were implanted under the fat pad on the right side of the animal. The left side received no implant and served as sham surgery control. Both sides were closed in a standard layered fashion. Animals were observed for 7, 14, 30, and 90 days. At timepoints for collection, animals were sacrificed and the inguinal fat pad with and without scaffolds was exposed and fixed in 4% PFA. The specimens were imbedded and sectioned for standard hematoxylin and eosin staining.

Statistical Analysis

All the results are expressed in mean values and the standard deviation. The statistical significance between a pair of groups was determined by conducting a One Way ANOVA with SigmaPlot 12.0 software (SPSS); a value of $p<0.05$ was considered statistically significant.

Any other suitable method for making embodiments of the composite 100 as disclosed herein are contemplated herein.

Example 2: Compression Test of the Nanofiber-Hydrogel Composite

For compression testing, the fiber-hydrogel samples were formed as cylinders 8.5 mm in diameter and ~4 mm in height, allowed to set overnight in molds at 37° C. The elastic moduli were determined via compression testing with a Bose EnduraTEC ELF 3200 (Eden Prairie, Minn.). The sample underwent uniaxial compression between two parallel plates, compressed to 50% Strain. The elastic moduli were determined by measuring the slope of the initial linear region. Two sample groups were tested, with the same hydrogel formulations, with and without fibers. The hydrogel-only sample was formed with 4.5 mg/mL of thiolated hyaluronic acid (Gylcosan Glycosil) and 10 mg/mL PEG-DA (polyethyl-glycol diacrylate, molecular weight 3350). The fiber-hydrogel composite group had the same hydrogel concentrations, but additionally has 6.75 mg/mL PCL nanofibers that have a surface functionalized with maleimide groups that can readily react with the thiolated hyaluronic acid.

Representative stress-strain traces can be seen in FIG. 2A. The hydrogel-only group had an elastic modulus of 320 Pa, while the fiber-hydrogel composite had a higher modulus of 750 Pa. The fiber-hydrogel composite's increased stiffness can be seen in the higher stress values at every strain value. The presence of functionalized nanofibers greatly increased the strength and stiffness of the material. Thus, the overall structure of the composite can have a stiffness matched to the target tissue, while the hydrogel component can have a lower crosslinking density than the density that would be needed to achieve the same stiffness without the benefit of nanofibers. This should result in a better cellular response for a given implant stiffness.

The sample groups were then tested via repeated compression to 25% Strain (20 cycles) at 0.1 Hz. Representative traces can be seen in FIG. 2B. This shows that the hydrogels and composites can tolerate repeated compression, and that the composite is persistently stiffer than the fiberless group.

Example 3: Cell-Materials Interaction

To test for the cellular response to the composite hydrogel, the migratory potential of adipose-derived stem cells (ASCs) was tested in varying formulations of hydrogels, with and without fibers.

Figure 3C:
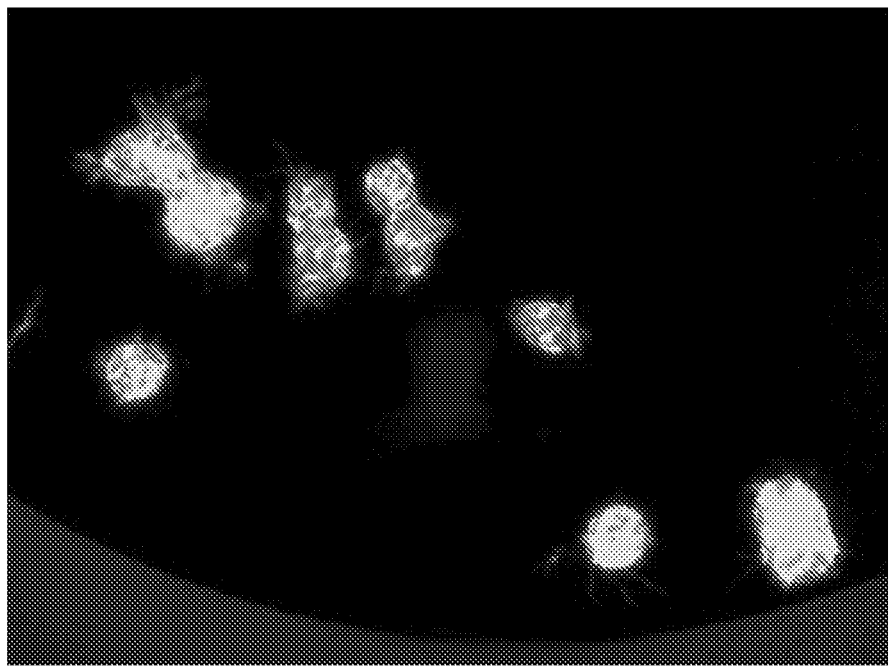
FIGS. 3C and 3D show a fluorescence image (FIG. 3C) and an overlay with the phase contrast image (FIG. 3D) of ASCs cultured in regular HA hydrogel for 4 days.
Figure 3D:
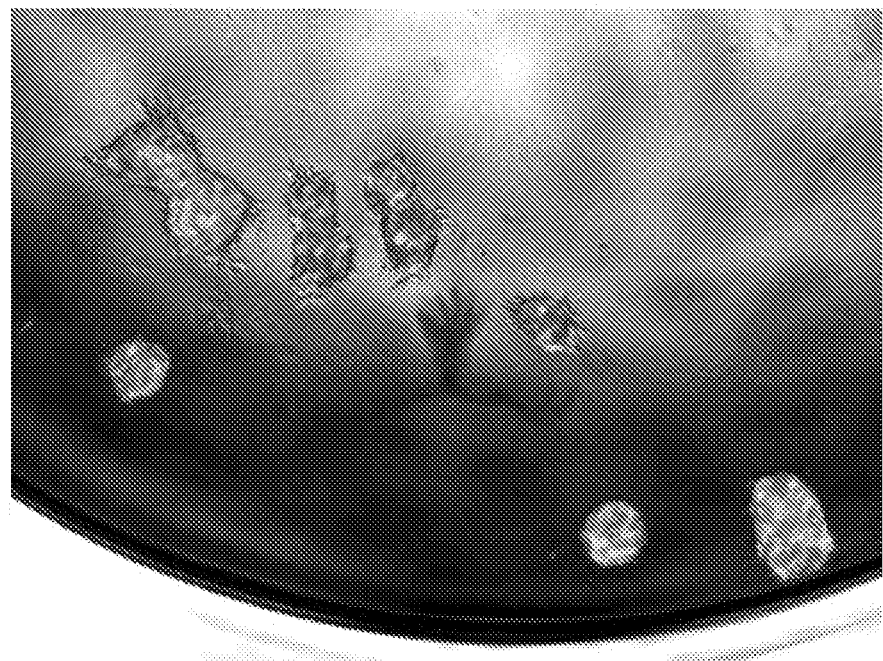

ASCs were transfected to express GFP, then formed into spheroid clusters by seeding the cells overnight in alginate molds made by Microtissues molds. The cells were seeded as spheroids to better evaluate cell motility, as the spheroids are a distinct point source from which migrating cells can be easily measured. The spheroids were mixed in to the hydrogel before being pipetted into a 96-well plate and being allowed to set. The cells were then imaged over the next several days to observe their migration. The cells were able to migrate progressively further as the concentrations of hyaluronic acid and PEG-DA were lowered, due to the respectively increasing pore sizes. At the same hydrogel densities (4.5 mg/mL hyaluronic acid and 2.5 mg/mL PEG-DA), cells were better able to migrate in samples with disperse nanofibers (12 mg/mL, FIGS. 3A and 3B) than without (as shown in FIGS. 3C and 3D). This indicates that the presence of functionalized nanofibers not only improved the mechanical properties of the nanofibers, but also can aid in improving cell migration.

To clearly demonstrate that the ASCs were strongly influenced by the presence of nanofibers, ASC spheroids were cultured on aligned nanofiber sheets, without hydrogel. After 96 hours, the cells (green in FIGS. 3C and 3D) clearly migrated out of the spheroid along the same axis of the aligned nanofibers (shown in FIG. 3D.)

Example 4: Tissue Compatibility of the Nanofiber-Hydrogel Composite

To study the biocompatibility of the composite nanomaterial scaffolds, they were implanted under the inguinal fat pads of Sprague-Dawley rats and observed for varying lengths of time. Under volatile anesthesia, a 1 cm incision was made just proximal to the inguinal crease bilaterally.

Figure 5A:
FIG. 5A is a photograph showing appearance of nanofiber-hydrogel composite implanted under the rat inguinal fat pad.
Figure 5B:
FIG. 5B shows an H&E staining image of a section from the tissue around the composite harvested at 2 weeks after implantation.

FIG. 5A is a photograph showing appearance of nanofiber-hydrogel composite in situ under rat inguinal fat pad. FIG. 5B shows H&E staining images of sections from tissues around the composite harvested at 2 weeks after implantation. Fronds of eosinophilic, dark pink stained mesenchymal cells are shown migrating into the nanomaterial (stained in light pink).

Figure 5C:
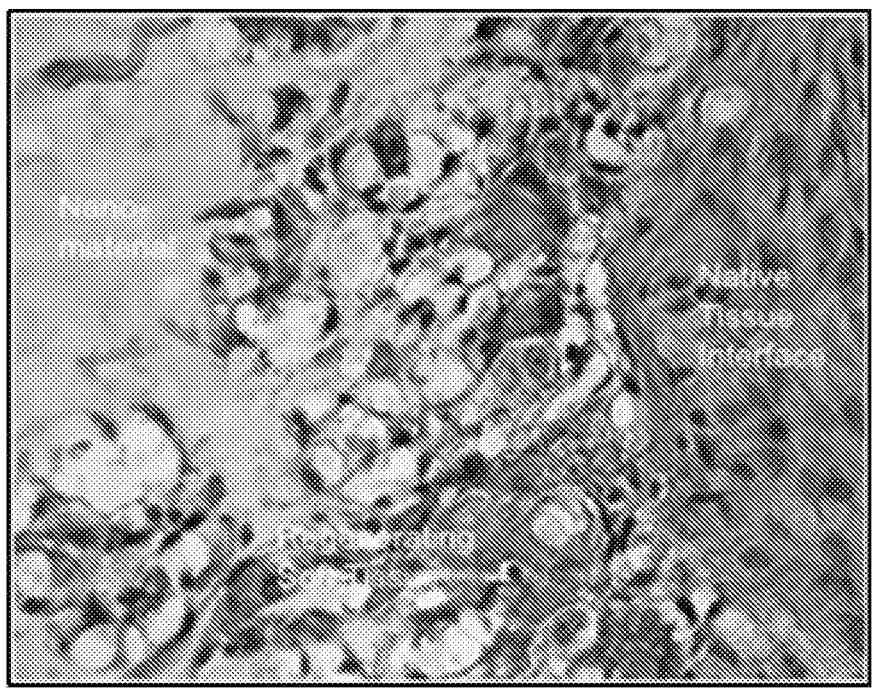
FIG. 5C shows an H& E staining image of a tissue section collected from composite-tissue interface at 4 weeks, showing cell infiltration.

FIG. 5C shows H& E staining images of tissue sections collected from composite-tissue interface at 4 weeks, showing cell infiltration. Mesenchymal tissue surrounding the site of implantation stains dark pink with eosin. The nanomaterial appears light pink. Infiltrating pink mesenchymal cells can be seen at the interface as well as putative adipocytes with clear round vacuoles.

Following blunt dissection of subcutaneous tissues, the inguinal fat pad was exposed. It was elevated with meticulous hemostasis using electrocautery and with careful preservation of feeding vessels. Scaffolds were implanted under the fat pad on the right side of the animal. The left side received no implant and served as sham surgery control. Both sides were closed in a standard layered fashion. Animals were observed for 2, 4, and 6 weeks. At timepoints for collection, animals were sacrificed and the inguinal fat pad with and without scaffolds was exposed and fixed in 4% PFA. The specimens were imbedded and sectioned for standard hematoxylin and eosin staining. At early timepoints (2 weeks), mesenchymal cells from the wound bed were found infiltrating the material suggesting that the material has sufficient porosity to enable native cellular ingrowth (dark pink staining in FIG. 5B).

Importantly cellular in-growth was achieved even in the absence of exogenous growth factors. The presence of cells infiltrating the material rather than merely surrounding it, distinguishes this composite nanomaterial from other alloplastic materials in current use. The latter materials are walled off by fibrous capsule and are therefore less desirable for soft tissue reconstruction. At later timepoints (4 weeks), cellular ingrowth is even more apparent with the appearance of vacuolar areas that may represent nascent adipocyte differentiation (dark pink staining and clear circles in FIG. 5C).

Example 5: Design of a Fiber-HA Hydrogel Composite

Figure 13A:
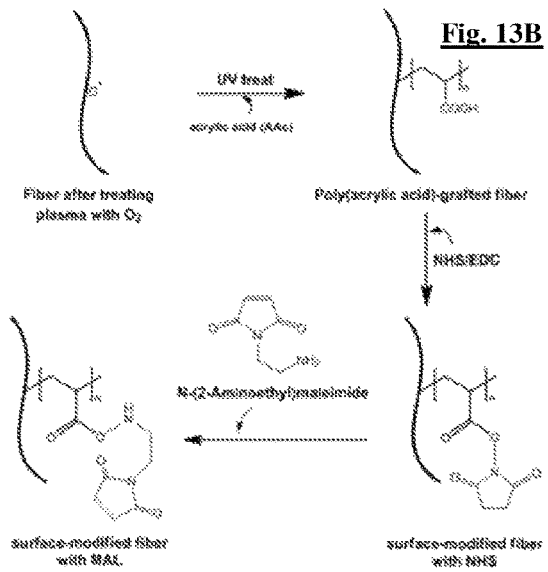
FIG. 13A depicts a schematic diagram of preparing surface-modified fibers with MAL via PAA-grafting method.
Figure 13B:
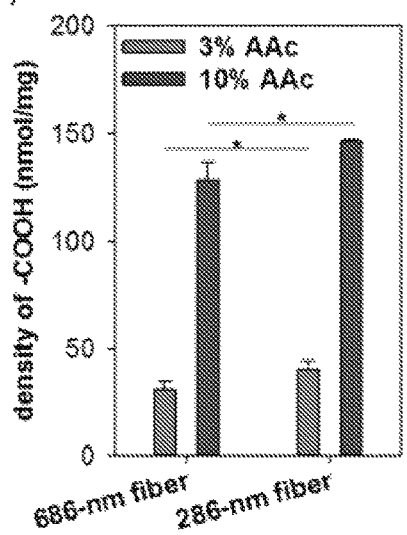
FIG. 13B depicts average densities of carboxyl groups on fibers after the PAA-grafting with 3 and 10% (v/v) of acrylic acid (*p<0.05, n=6).

The fibers could form the fibrous architecture that can often be seen in the native extracellular matrix, aiding cell migration and reinforcing the initially-low mechanical properties of the hydrogel. By introducing interfacial bonding between the hydrogel and fibers (FIG. 6A, FIG. 6B), the composite is strengthened without decreasing the average pore size and porosity (FIG. 6) that would significantly hinder cell migration. It was also expected that the mechanical properties could be tuned by controlling the density of the interfacial bonding between the hydrogel and the surface of fibers. Here, surface-functionalized fibers were prepared with maleimide (MAL) to introduce the interfacial bonding with thiolated hyaluronic acid (HA-SH) (FIG. 6). The surface of electrospun poly(ε-caprolactone) (PCL) fibers was treated with 02 plasma to induce free-radicals onto its surface before grafting poly(acrylic acid) (PAA). The carboxyl groups was activated by coupling reagents, NHS and EDC, then N-(2-aminoethyl)maleimide was reacted to the activated carboxyl groups (FIG. 13). Subsequently, MAL-functionalized fibers were introduced to hydrogel precursor solution composed of HA-SH and PEGDA for fabricating a fiber-hydrogel composite. The thiol groups of the HA were employed to form a gel by reacting with both the MAL groups on the fibers and the DA groups of the PEG linker. Interestingly, a cross-section of a fiber-hydrogel composite showed a fibrous 3D structure with a high porosity (FIG. 6), compared to a cross-section of HA hydrogel with a similar crosslinking density. The resulting composites showed even distribution of nanofibers across both the width and height of the composite, enabling isotropic reinforcement. Also, a rehydrated fiber-HA hydrogel composite showed 99.34% of volume recovery after lyophilization while HA hydrogel showed 70.17% of volume recovery (FIG. 6D).

Example 6: Compressive Modulus of a Fiber-HA Hydrogel Composite

Figures 7A, 7B:
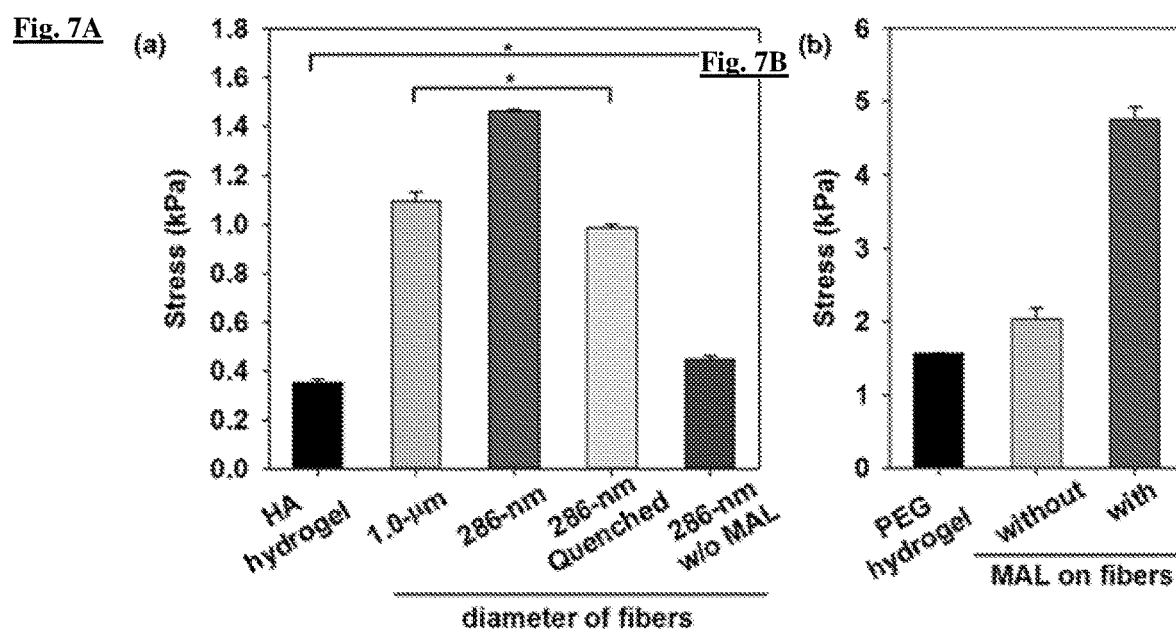
FIG. 7A depicts the effect of fiber diameter and interfacial bonding on reinforcing compressive modulus of the PCL fiber-HA hydrogel composite and HA hydrogel. HA hydrogel and composites were prepared based on 4.5 mg/ml of HA. The values of stress were measured at 50% of strain; *$p<0.05$ (Student-t test).
FIG. 7B depicts the effect of fiber diameter and interfacial bonding on reinforcing compressive modulus of the PCL fiber-HA hydrogel composite in comparison with HA hydrogel. PEG hydrogel and composites were prepared based on 30 mg/ml of PEGSH and 20 mg/ml of PEGDA, and 1.0-μm PCL fibers were used to synthesize the fiber-PEG hydrogel composites. The values of stress were measured at 50% of strain; *$p<0.05$ (Student-t test).

First, the composite was verified to possess its maximal stiffness (under shear) when the reactive groups were equal on a molar basis. The thiol groups on the HA can react with either the MAL groups on the nanofibers or the acrylate groups on the PEG-DA, so when the molar ratio of SH to (DA+MAL) was approximately 1 to 1, the gels showed an optimal shear storage modulus. Therefore, this ratio was maintained for all of the subsequent studies. The gels underwent unconfined compression testing to evaluate the elastic modulus of HA hydrogel and fiber-HA hydrogel composites (FIG. 7). The reinforcing effect of the functionalized nanofibers can be seen in the compressive stress when strained to 50% (FIG. 7A). The compressive stress was 3.1-fold greater in the 1.0-μm fiber group than the hydrogel-only group, showing the effect of mechanical reinforcement. The 286-nm fiber group showed even more pronounced reinforcement effect with a compressive stress of 4.2-fold higher at the 50% strain. Interestingly, the stiffening effect of the 286-nm fibers was greatly reduced to only 1.3-fold over the hydrogel when the maleimide groups were quenched prior to gelation, confirming that the interfacial bonding of the fiber to the hydrogel is crucial to the reinforcement effect of the functionalized fibers. Moreover, when the 286-nm fibers were not functionalized before forming the composite, the reinforcement effect was disappeared, resulting in composites barely stiffer than the hydrogel alone. The same reinforcement effect can be seen when formulating stiffer gels by formulating composites with higher concentrations of HA and PEG-DA (FIG. 7). The interfacial bonding also shows a dose-response in its stiffening of the composite gel, as adding progressively more maleimide groups to the nanofiber surface results in progressively stiffer materials providing more evidence of the importance of the interfacial bonding. The composites were also tested for changes in mechanical properties before and after dehydration and rehydration. The gels, with and without functionalized nanofibers of two different maleimide densities, were mechanically tested under compression. The gels were then lyophilized, then allowed to rehydrate fully and tested for compression again. All samples maintained their stiffnesses after rehydration, indicating that the composites may be suitable for use clinically as a lyophilized product. While the HA-alone gel seemingly maintained its stiffness, the gel itself had compacted significantly during the dehydration-rehydration process, unlike the fiber-containing groups. The composite gels were also subjected to cyclic loading to test for fatigue-effects, with representative traces shown in FIG. 10. With repeated loading to 25% strain, the composite gels maintained their stiffnesses over time and were consistently stiffer than the hydrogel alone.

Example 7: Shear Storage Modulus of a Fiber-HA Hydrogel Composite

Figures 9A, 9B:
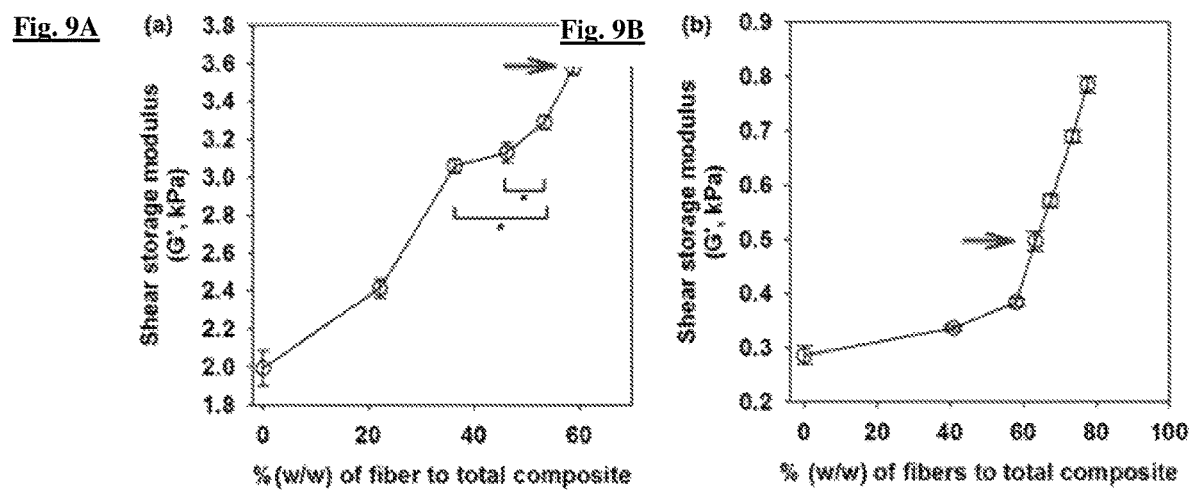
FIG. 9A depicts the effect of fiber-loading amount on shear storage modulus of the PCL fiber-HA hydrogel composite. The HA hydrogel and composites were synthesized using 10 mg/ml of HA. Shear storage moduli are measured at 1-Hz frequency. The arrow indicates the condition for the composite with a 1 to 2 of molar ratio of SH groups in PEGDA to (DA+MAL) groups. *$p<0.05$ (Student-t test).
FIG. 9B depicts the effect of fiber-loading amount on shear storage modulus of the PCL fiber-HA hydrogel composite. The HA hydrogel and composites were synthesized using 4.5-mg/ml of HA. Shear storage moduli are measured at 1-Hz frequency. The arrow indicates the condition for the composite with a 1 to 2 of molar ratio of SH groups in PEGDA to (DA+MAL) groups. *$p<0.05$ (Student-t test).
Figure 12A:
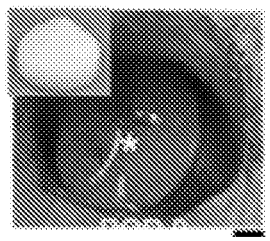
FIG. 12A depicts tissue regeneration mediated by the implanted fiber-HA hydrogel composite and HA hydrogel in 30 days. Macroscopic images of the composite before (insets) and after implantation under the inguinal fat pad (scale bar=2 mm) are shown. White stars indicate the implanted matrices.
Figure 12B:
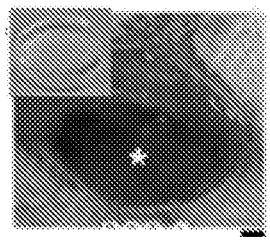
FIG. 12B depicts tissue regeneration mediated by the implanted fiber-HA hydrogel composite and HA hydrogel in 30 days. Macroscopic images of the HA hydrogel before (insets) and after implantation under the inguinal fat pad (scale bar=2 mm) are shown. White stars indicate the implanted matrices.
Figure 12C:
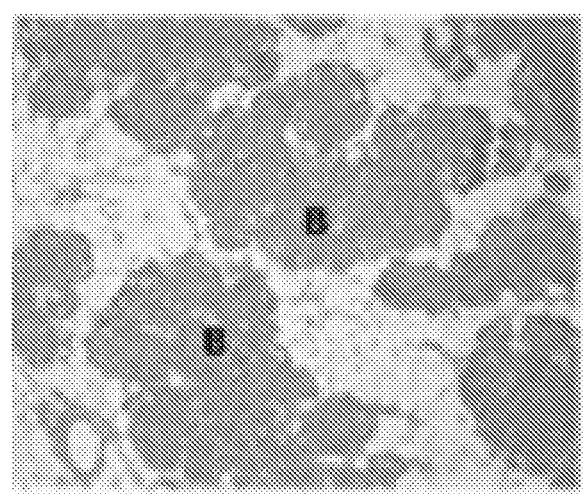
FIG. 12C depicts an H&E-stained image of native fat tissue. In the image, B=brown adipose tissue. Scale bar=200 μm.
Figure 12D:
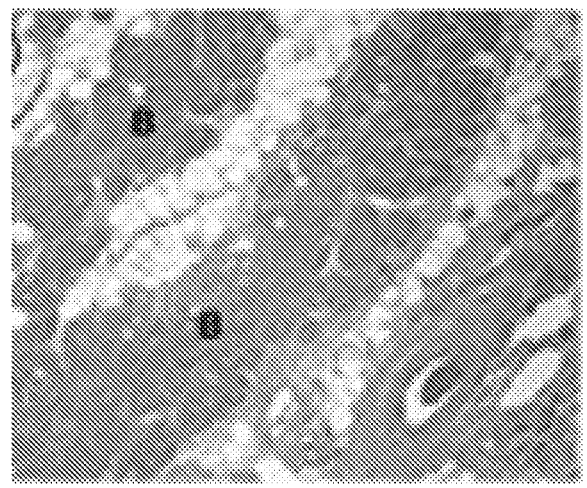
FIG. 12D depicts an H&E image of healed tissue after sham surgery. In the image, B=brown adipose tissue. Scale bar=200 μm.
Figure 12E:
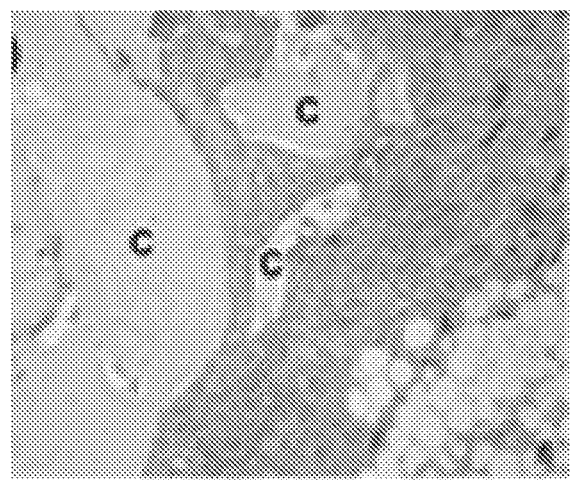
FIG. 12E depicts an H&E-stained image of tissue regeneration mediated by the implanted fiber-HA hydrogel composite after 14 days. In the image, C=fiber-HA hydrogel composite. Scale bar=200 μm.
Figure 12F:
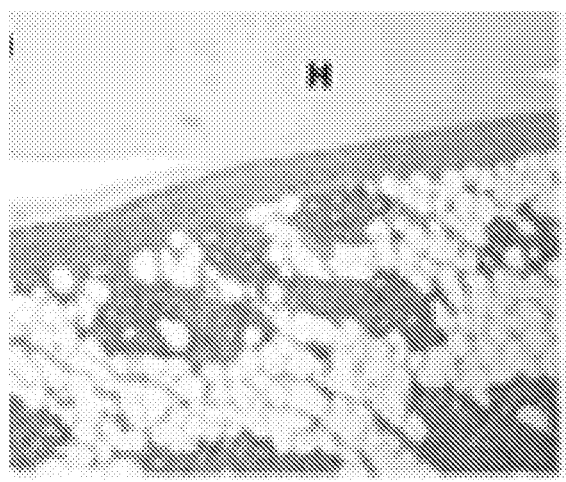
FIG. 12F depicts an H&E-stained image of tissue regeneration mediated by the implanted HA hydrogel (without fibers) after 14 days. In the image, H=HA hydrogel. Scale bar=200 μm.
Figure 12G:
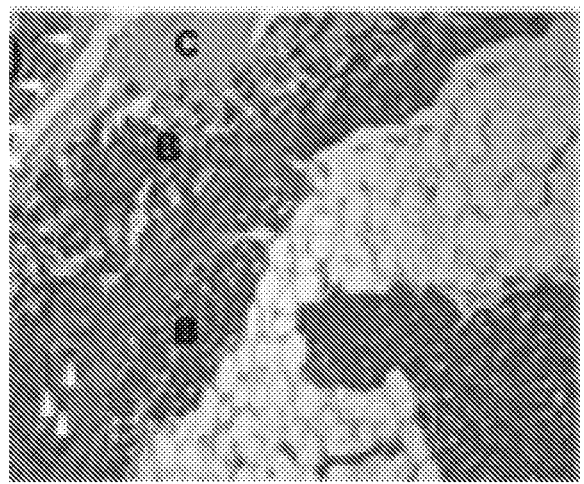
FIG. 12G depicts an H&E-stained image of tissue regeneration mediated by the implanted fiber-HA hydrogel composite after 30 days. In the image, C=fiber-HA hydrogel composite, B=brown adipose tissue, yellow arrows=blood vessels. Scale bar=200 μm.
Figure 12H:
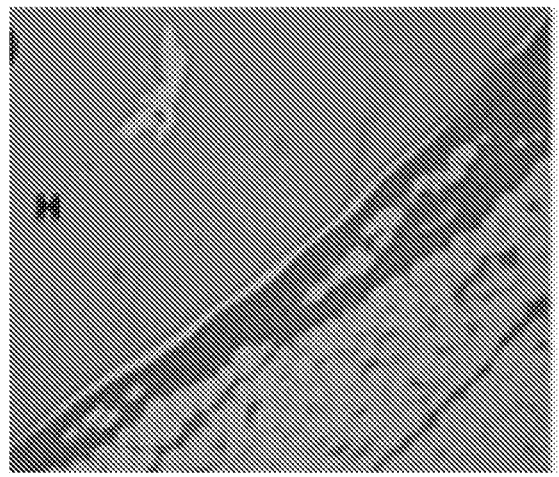
FIG. 12H depicts an H&E-stained image of tissue regeneration mediated by the implanted HA hydrogel (without fibers) after 30 days. In the image, H=HA hydrogel. Scale bar=200 μm.
Figure 12I:
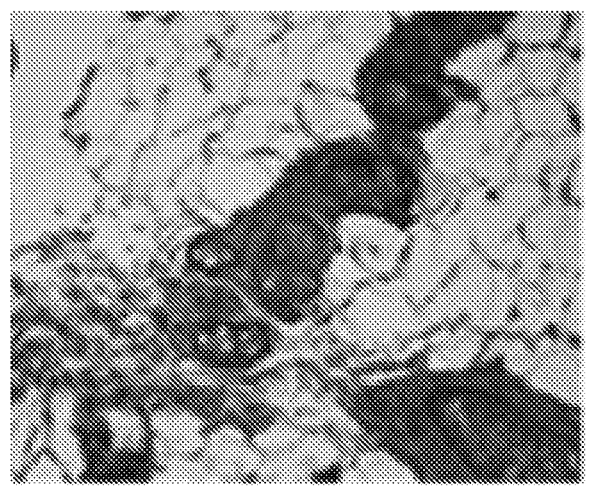
FIG. 12I depicts a Masson's trichrome stained-image of native fat tissue. Blue staining from Masson's trichromatic staining indicates total collagen in examined tissue. Scale bar=200 μm.
Figure 12J:
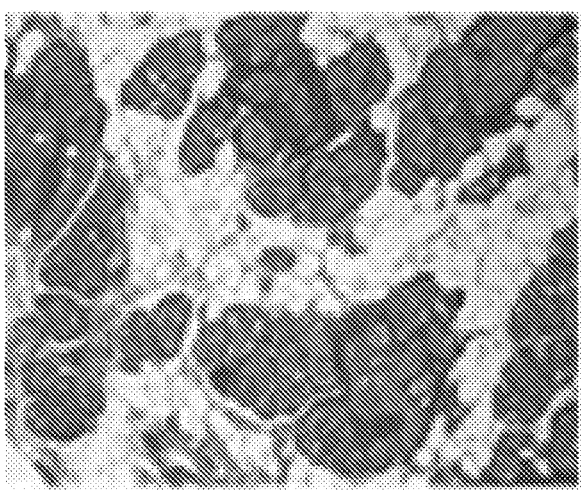
FIG. 12J depicts a Masson's trichrome stained-image of healed tissue after sham surgery. Blue staining from Masson's trichromatic staining indicates total collagen in examined tissue. Scale bar=200 μm.
Figure 12K:
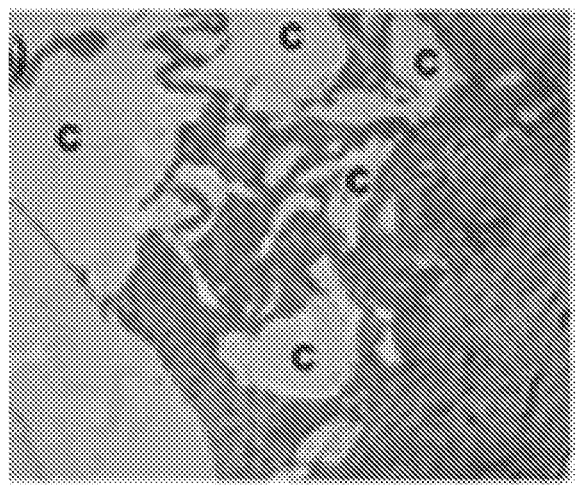
FIG. 12K depicts a Masson's trichrome stained-image of tissue regeneration mediated by the implanted fiber-HA hydrogel composite after 14 days. Blue staining from Masson's trichromatic staining indicates total collagen in examined tissue. In the image, C=fiber-HA hydrogel composite. Scale bar=200 μm.
Figure 12L:
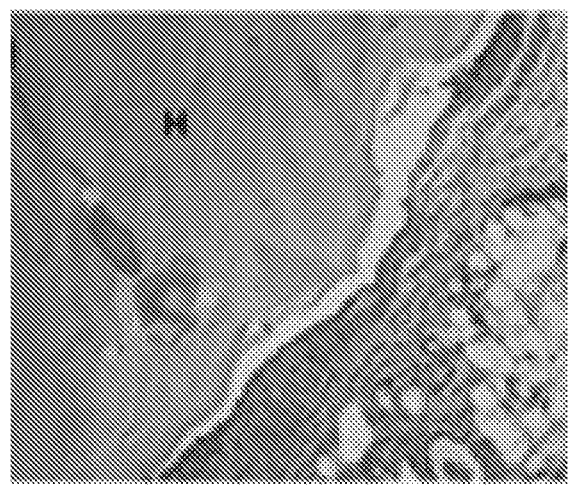
FIG. 12L depicts a Masson's trichrome stained-image of tissue regeneration mediated by the implanted HA hydrogel (without fibers) after 14 days. Blue staining from Masson's trichromatic staining indicates total collagen in examined tissue. In the image, H=HA hydrogel. Scale bar=200 μm.
Figure 12M:
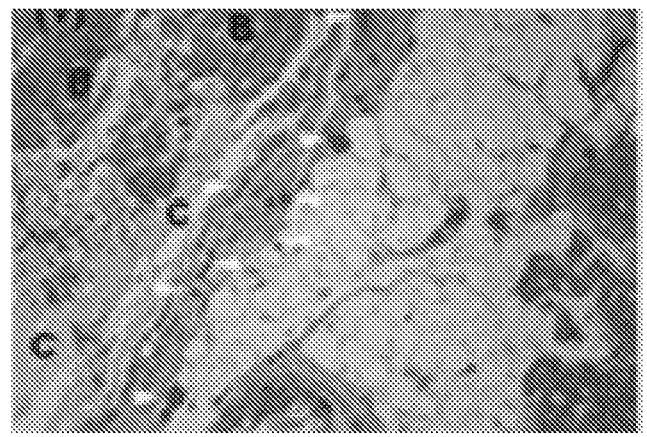
FIG. 12M depicts a Masson's trichrome stained-image of tissue regeneration mediated by the implanted fiber-HA hydrogel composite after 30 days. Blue staining from Masson's trichromatic staining indicates total collagen in examined tissue. In the image, C=fiber-HA hydrogel composite, B=brown adipose tissue, yellow arrow=blood vessel. Scale bar=200 μm.
Figure 12N:
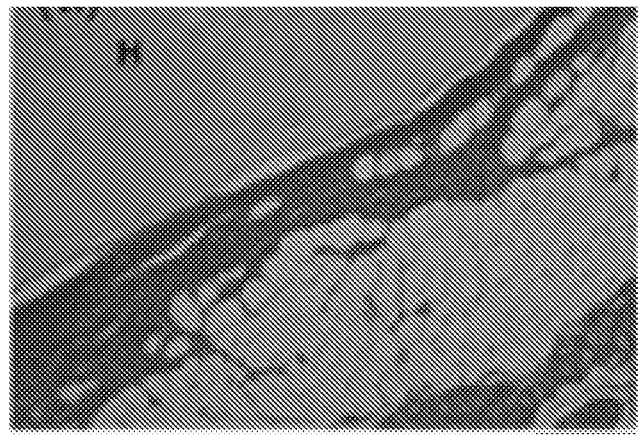
FIG. 12N depicts a Masson's trichrome stained-image of tissue regeneration mediated by the implanted HA hydrogel (without fibers) after 30 days. Blue staining from Masson's trichromatic staining indicates total collagen in examined tissue. In the image, H=HA hydrogel. Scale bar=200 μm.

In addition to the higher compression modulus, the Fiber-HA hydrogel composites showed a significantly higher shear storage modulus than the HA hydrogel alone (FIG. 8A). The shear storage modulus of a composite with 286-nm fibers was higher than that of a composite with 686-nm fibers (FIG. 8C). It was also confirmed that the shear storage modulus of the composites increased by increasing the maleimide surface density on the 286-nm fibers, similar to the modulus under compression testing (FIG. 8D). By introducing fibers with 62 nmol/mg MAL on its surface, the composite showed a 1.3-fold increase in its shear storage modulus compared to that of the HA hydrogel alone. Moreover, the shear storage modulus of a composite with 147 nmol/mg MAL on its fibers was increased 1.8-fold over the modulus of the 62 nmol/mg MAL group, showing a clear dose response to the corresponding 2.4-fold increase in the MAL surface density on the fibers. When the MAL groups on the fibers were quenched prior to gelation, the shear storage modulus correspondingly decreased compared to that of the unquenched fibers, similarly to what was seen in the compression testing. Additionally, the shear storage modulus of the composites was maintained when the frequency increased to 10 Hz while both the HA hydrogel alone and the composite with quenched fibers showed diminishing shear storage moduli at 10 Hz than those at 1 Hz. The shear storage modulus of the composites was increased with increasing MAL surface density on fibers regardless of surface area (diameter) of fibers, indicating that the previously observed effect of fiber diameter on stiffness may have been a function of maleimide density (FIG. 8D). A linear regression was obtained from the correlation between the MAL surface density and shear storage modulus with $R^2=0.93$. Moreover, the composites showed a dose response to fiber loading, as the shear storage modulus of the composites increased with an increasing weight ratio of functionalized fibers to hydrogel components (FIG. 9).

Example 8: Cell Migration in a Fiber-HA Hydrogel Composite In Vitro

Figure 16:
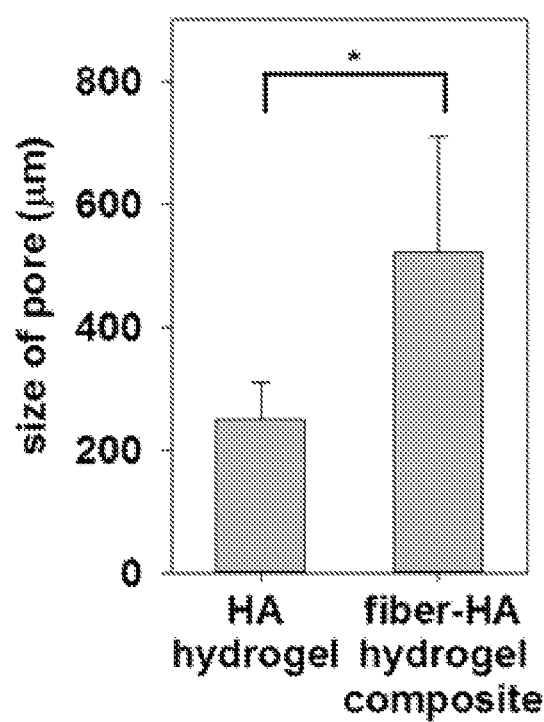
FIG. 16 depicts the average pore size of HA hydrogel and nanofiber-HA hydrogel composite are estimated based on the SEM images of their cross-sections *p<0.05).
Figure 17A:
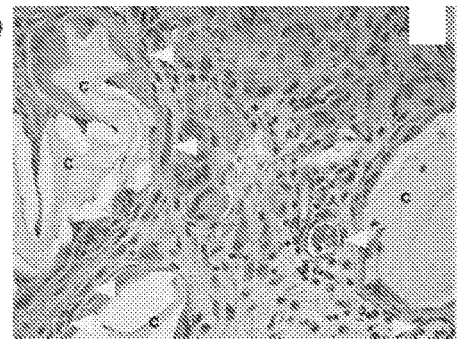
FIG. 17A depicts cell infiltration and tissue in-growth through the fiber-HA hydrogel composite on Day 14. The sectioned tissues are stained by H&E for total collagen (blue). Labels: C=fiber-HA hydrogel composite, yellow arrow=blood vessel. Scale bar=50 μm.
Figure 17B:
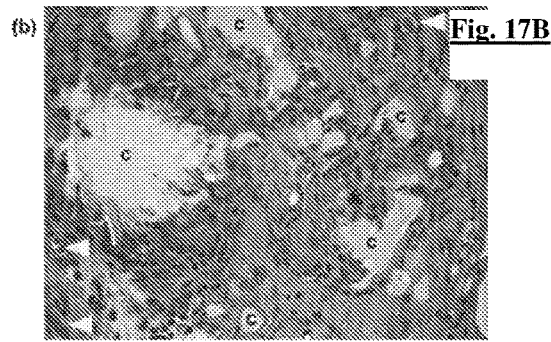
FIG. 17B depicts cell infiltration and tissue in-growth through the fiber-HA hydrogel composite on Day 14. The sectioned tissues are stained by Masson's Trichrome for total collagen (blue). Labels: C=fiber-HA hydrogel composite, yellow arrow=blood vessel. Scale bar=50 μm.
Figure 17C:
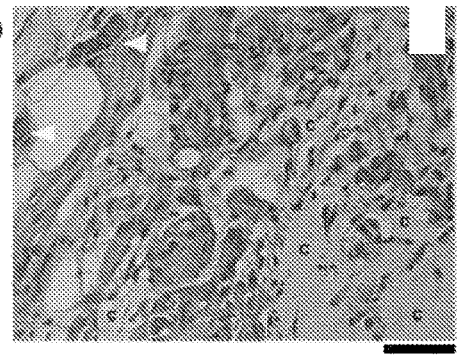
FIG. 17C depicts cell infiltration and tissue in-growth through the fiber-HA hydrogel composite on Day 30. The sectioned tissues are stained by H&E for total collagen (blue). Labels: C=fiber-HA hydrogel composite, yellow arrow=blood vessel. Scale bar=50 μm.
Figure 17D:
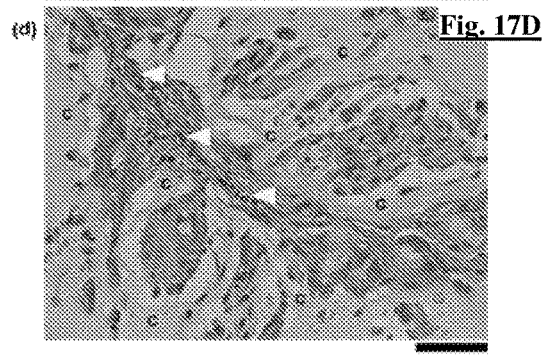
FIG. 17D depicts cell infiltration and tissue in-growth through the fiber-HA hydrogel composite on Day 30. The sectioned tissues are stained by Masson's Trichrome for total collagen (blue). Labels: C=fiber-HA hydrogel composite, yellow arrow=blood vessel. Scale bar=50 μm.
Figure 18A:
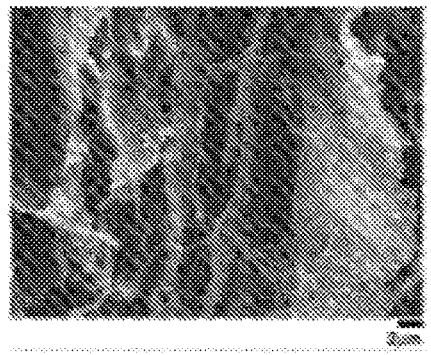
FIG. 18A depicts an SEM image of a cross-section of the decellularized fat tissue; note that this is the same sample and image as FIG. 6G, included here again for comparison purpose.
Figure 18B:
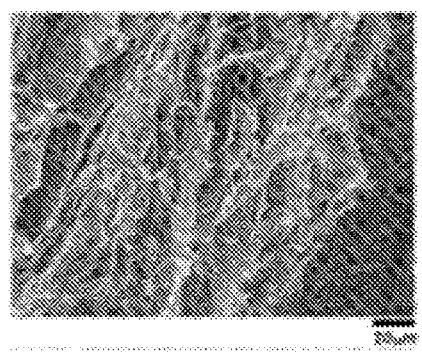
FIG. 18B depicts an SEM image of another cross-section of the decellularized fat tissue.
Figure 18C:
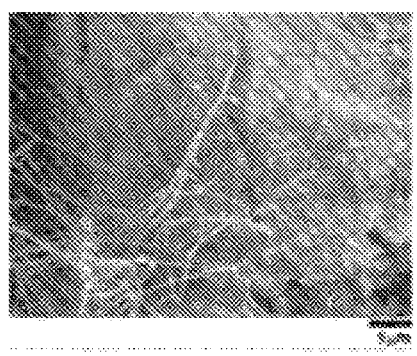
FIG. 18C depicts an SEM image of yet another cross-section of the decellularized fat tissue.
Figure 18D:
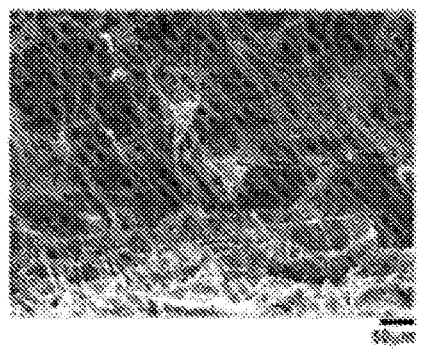
FIG. 18D depicts an SEM image of a cross-section of the fiber-HA hydrogel composite; note that this is the same sample and image as FIG. 1D and FIG. 6F, included here again for comparison purpose.
Figure 18E:
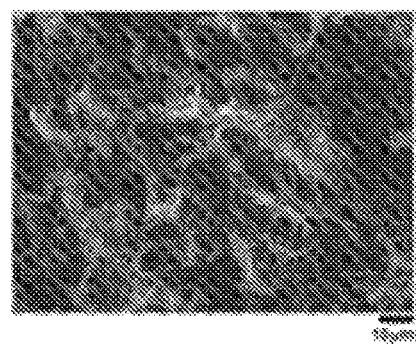
FIG. 18E depicts an SEM image of another cross-section of the fiber-HA hydrogel composite.
Figure 18F:
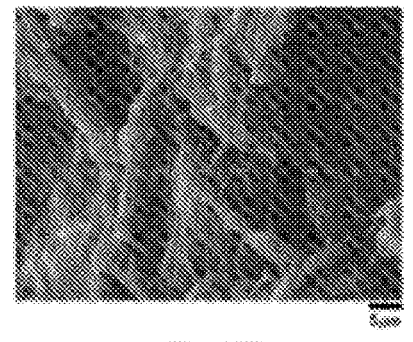
FIG. 18F depicts an SEM image of yet another cross-section of the fiber-HA hydrogel composite.

It was hypothesized that the fiber-HA hydrogel composite enhanced cell migration compared to HA hydrogel because of (i) a higher porosity of the composite with a larger pore size, providing a spatiality for cell migration when they have the same mechanical properties and (ii) an ECM-mimicked fibrous architecture in the composite, allowing to intrinsically guide cell migration. Therefore, for demonstrating the current hypothesis, spheroids of human adipose-derived stem cells (hASCs) as a model cell were seeded and a mimicked tissue chunk inside HA hydrogel and composites, then the hASCs spheroids were cultured for 27 days (FIG. 11). ASCs were chosen due to their presence in fat tissues and importance in both angiogenesis and adipocyte formation. Although the composites have the similar Young's modulus, 1.9 kPa, to the HA hydrogel, the pore size of the composites is 2.08-fold bigger than that of HA hydrogel (FIG. 16). Hence, it was clearly observed that hASCs migrated 3-dimensionally inside the composites (FIG. 11B-11E) because the bigger pores could accommodate to migrate the cells, while hASCs maintained their spheroid shape without any cell migration in HA hydrogel (FIG. 11A). In particular, the cell migration was magnificently enhanced when the fibers were modified with the cell adhesion peptide, RGD, for the composite (FIG. 11C). However, in the in vivo setting, diffusion of factors into the composite from the local milieu should provide additional adhesive cues, lessening this difference. In some instances, partial fibers slightly formed a cluster during gelation due to hydrophobic interaction between PCL fibers, and it was observed bodies of cells preferentially grabbing the fibers clusters inside the composites (FIGS. 11D and 11E). Furthermore, at the same HA and PEG-DA concentrations (FIG. 19), the composites showed enhanced cell migration as compared to the fiberless group, showing that the nanofibers themselves could intrinsically help guide cell migration regardless of the porosity.

Example 9: Tissue Response and Host Tissue Infiltration

To determine the therapeutic potential of these composite implants, the composite implants were tested in vivo in a rat fatpad model. The formulations of the implant groups were formulated to achieve the same initial 2 kPa stiffness as the composite gel and the target adipose tissue. Thusly, the formulation of the HA-gel alone implant had a higher concentration of both thiolated HA and PEG-DA to match the stiffness of the fiber-composite group. Despite the higher concentrations, the HA-alone implants were unable to maintain their shape and volume over the course of the study. Under gross observation after 4 weeks, the HA-alone implants were stretched out and significantly smaller in volume. Considering their gross appearance and their histological lack of infiltration, the HA-alone system cannot be optimized to be able to encourage cell infiltration and maintain a predetermined shape. The fiber-gel composite implants, however, well maintained their original shape under gross observation after 90 days in vivo. Remarkably, however, under histological observation the composites had been so thoroughly infiltrated that the border between implant and native tissue had become difficult to determine.

A soft tissue defect model in Lewis rats has been developed, where the inguinal fat pad is exposed and elevated using microsurgical techniques and the pre-shaped composites are placed underneath. This well-defined model is ideal to address all elements of Aim 3 hypothesis and the scale amenable to the R21 study. Even though this does not directly demonstrate the ability of such a composite for restoring large defects, it will establish the proof-of-principle and confirm all essential functionalities of the composite design, and lay the foundation for larger animal model to test the large defect restoration in more clinically relevant models.

In a pilot study, PCL nanofiber-HA hydrogel composites and HA hydrogels were implanted with similar moduli under the inguinal fat pad of 8-12 week old male Lewis rats (n=3 per time point). Both the HA hydrogel and composite groups showed good tissue compatibility at days 14 and 30 after transplantation (FIG. 12, POD 14, similar observations at POD 30. POD=Post-Operative Date). Histology at POD 30 did not show higher level of inflammatory response than sham surgery group. H&E and Masson's trichrome staining showed septation and cellular infiltration by native fat through the composite, capillary formation around the perimeter, and regeneration of glandular as well as adipocyte portions of native fat (FIG. 12). HA hydrogel control on the other hand, lacked cellular infiltration and formed a thin sheet of fibrotic tissue and foreign body response. This HA hydrogel was prepared with 2 kPa to ensure sufficient mechanical property. This result highlights the importance of porosity of the scaffold for cell infiltration.

At an early time point (2 weeks), mesenchymal cells from the wound bed were found infiltrating the material suggesting that the material has sufficient porosity to enable native cellular ingrowth (dark pink staining in FIG. 12). Importantly, cellular ingrowth was achieved even in the absence of exogenous growth factors. The presence of cells infiltrating the material rather than merely surrounding it, distinguishes this composite nanomaterial from other alloplastic materials in current use. The latter materials are walled off by fibrous capsule and are therefore less desirable for soft tissue reconstruction. At later time points (4 weeks), cellular ingrowth is even more apparent with the appearance of vacuolar areas that may represent nascent adipocyte differentiation.

Example 10: Heparinized Formulation

A composite formulation has also been prepared with heparin conjugated to the hyaluronic acid. This formulation was tested in vivo identically to the preformed scaffold above. The tissue was harvested (n=3) at 7 days, 14 days, 30 days, and 90 days. Many relevant growth factors have heparin-binding domains, such as bFGF, PDGF, and VEGF. The conjugated heparin can serve two purposes; firstly, it can bind many of the endogenous growth factors that will be present at the injection site and serve as a local reservoir and attractive cue to the regenerating tissue. Secondly, the heparinized composite can be used to pre-load the scaffold with growth factors to better potentiate regeneration. The heparinized scaffolds showed enhanced angiogenesis at 7 and 14 days as compared to the unheparinized composite scaffolds, but similar results at 30 and 90 days.

Example 11: Injectable Formulation

Figures 20A, 20B, 20C, 20D:
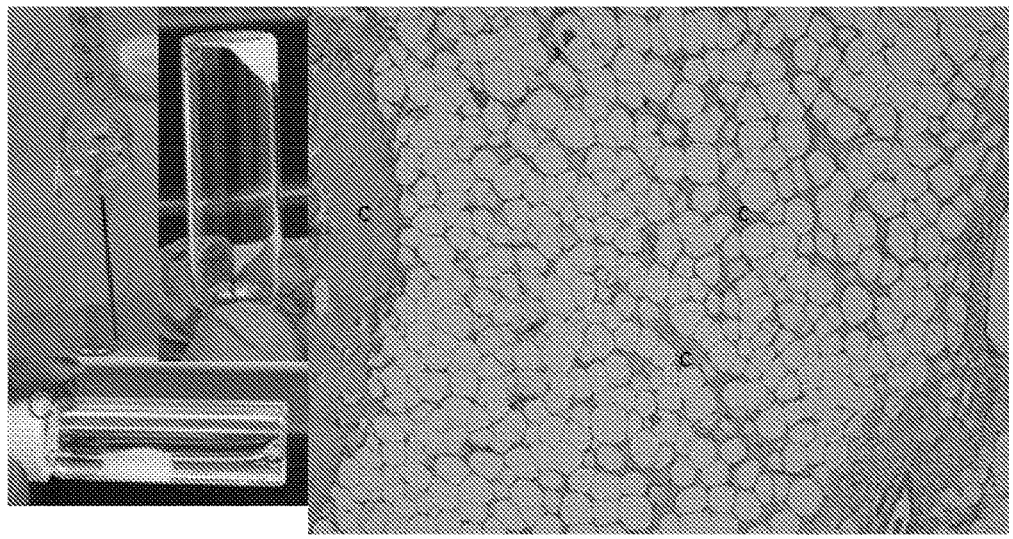
FIG. 20A depicts an injectable formulation. The fiber-hydrogel composite is loaded into a syringe and injected through a hypodermic needle.
FIG. 20B depicts an injectable composite immediately after injection.
FIG. 20C depicts an injectable composite after injection, maintaining its volume and ability to exclude liquid.
FIG. 20D depicts cell infiltration and tissue in-growth through an injectable fiber-HA hydrogel composite on Day 30, showing extensive cellular remodeling and adipocyte formation. The sectioned tissues are stained by H&E. In the image, c=fiber-HA hydrogel composite.

The hydrogel-nanofiber composite has also been formulated into an injectable variant. 200 µL of the same composition as used for the pre-formed composite used in vivo (5 mg/mL thiolated HA, 5 mg/mL PEG-DA, 12.5 mg/mL fibers) was mixed and allowed to partially set in the syringe for 8-10 min. At this time, the composite is a viscous, flowable liquid that can be injected through a surgical needle (FIG. 20). Once injected, the composite maintains its shape when inverted and is non-dispersive, shape-maintaining and non/low-swelling when submersed in water. To test for biocompatibility of the injectable composite, the suspension is then injected into the inguinal fat pad of the rat through a 21-gauge needle. The tissue was then harvested (n=3) at 7 days, 14 days, 30 days, and 90 days and analyzed identically to the previous examples. The composite demonstrated extensive cellular remodeling at 30 days while maintaining volume and without causing fibrotic encapsulation. Early-stage adipocytes can clearly be seen developing within the composite material.

Example 12: Discussion of Examples 5-11

Hydrogels have been widely studied as a filler material for regeneration of tissue defects due to its 3D hydrated environment and high porosity, which facilitate cell migration. However, hydrogels have proven to be poor substitutes for volumetric defects, because the relatively weak mechanical properties of the hydrogel are insufficient to maintain its volume for the entire period of tissue regeneration, as the hydrogel can be easily degraded and collapsed by body fluids and internal and external stresses. To improve the mechanical properties of the hydrogel, the main strategies in the field have been to (i) increase the concentration of hydrogel precursors, (ii) increase the density of the cross-linking network inside the hydrogel, and to (iii) introduce reinforcing materials such as by embedding hydroxyapatite particles or laminating with fiber sheets. [Mater Chem Physics, 2008, 107, 364-369, Biomaterials 2006, 27, 505-518, Acta Biomaterialia 2010, 6, 1992-2002]. Unfortunately, these very strengthening strategies inherently reduced the average pore size and porosity of the resulting hydrogel, preventing cells from being able to migrate into these hydrogels. Therefore, it was sought to strengthen hydrogels by a new mechanism that would still retain the high porosity than allows for rapid cellular infiltration. A composite material was designed by introducing functionalized nanofibers that could strengthen the overall hydrogel composite while leaving the hydrogel phase largely intact, including porosity. The resulting fiber-hydrogel composite improves upon previous soft tissue composites because of two key components. Firstly, the nanofibers needed to be uniformly dispersed at a high loading level within the hydrogel to achieve isotropic strengthening. The tissue-engineering field has generally utilized electrospun nanofibers as flat sheets or mats of fibers. These are then typically made into composites by impregnating the mats with a hydrogel precursor solution.

This greatly constrains the dispersion of the nanofibers throughout the hydrogel and limits the geometry of the composites to 2D sheets or tubes. While these geometries are useful for certain applications such as nerve repair or wound dressings, they are poor choices for repairing volumetric defects. By cryomilling the fiber sheets, it was possible to reduce the average fiber length to the sufficiently short length that allow them to remain in suspension in aqueous solutions. Thus, the samples were then easily pipetted into hydrogel precursor solutions, creating a uniform dispersion of nanofiber fragments throughout the hydrogel volume before gelation. The solution can then be directly used as an injectable formulation, or added to molds to form scaffold gels of any arbitrary geometry, unlike the limited planar geometry of most electrospun nanofiber meshes. The composite structure of dispersed fibers within a hydrogel also recapitulates the fibrous architecture of the extracellular matrix (FIG. 6G), providing adhesion sites that may aide cell migration within the composite.

Secondly, simply dispersing the nanofibers within the hydrogel is insufficient to form a strong composite. These data indicated that merely including the nanofibers themselves provided very little improvement in the elastic modulus of the composite, with improvements occurring only when interfacial bonding was introduced. The interfacial bonding is necessary because without forming a strong linkage between the hydrogel and fiber components, the water and hydrogel components could slide past the fiber components without transferring the loads to the stiffer material. Furthermore, the interface between such disparate materials could lead to delamination and failure in the composite. Further, PCL's initial hydrophobicity makes it difficult to disperse in aqueous solutions, as the fibers preferentially clump together and form clots that fall out of suspension. Plasma treatment and subsequent functionalization with carboxylic acid groups and amine groups greatly increases the hydrophilicity of the fibers and allows dispersion. The dramatic increase in mechanical properties only occurred when interfacial bonding occurred between the maleimide groups on the fiber surfaces and the thiol groups on the hyaluronic acid molecules. This covalent-strength bonding transfers loads more efficiently to the fibers during compression or tension, leading to a stiffer, stronger material. Moreover, the composites show a strong trend of increasing elastic moduli with increasing maleimide density, emphasizing its primacy in the strengthening mechanism, as well as the tunable nature of the reinforcement.

Figure 14:
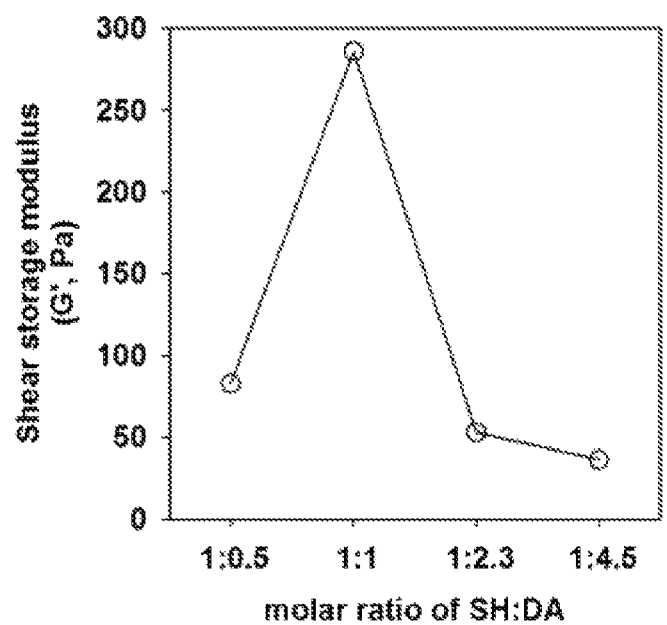
FIG. 14 depicts shear storage moduli of HA hydrogel with various molar ratios of SH to DA prepared with 4.5 mg/ml HA-SH.
Figure 15A:
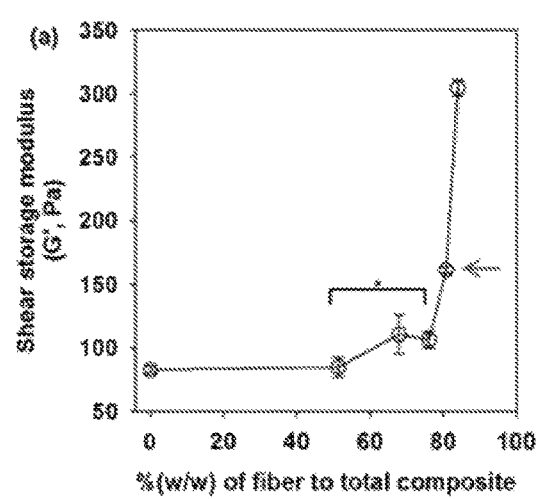
FIG. 15A depicts shear storage moduli of fiber-HA hydrogel composites prepared from various amount of fibers. The average diameter of fibers is 686 nm, MAL surface density on the fibers is 100 nmol/mg, and the composites are prepared with 4.5 mg/ml of HA-SH and 5 mg/ml of PEGDA. Blue arrows indicate 1 to 2 of molar ratio of SH groups to (DA+MAL) groups. *p<0.05 (n=3).
Figure 15B:
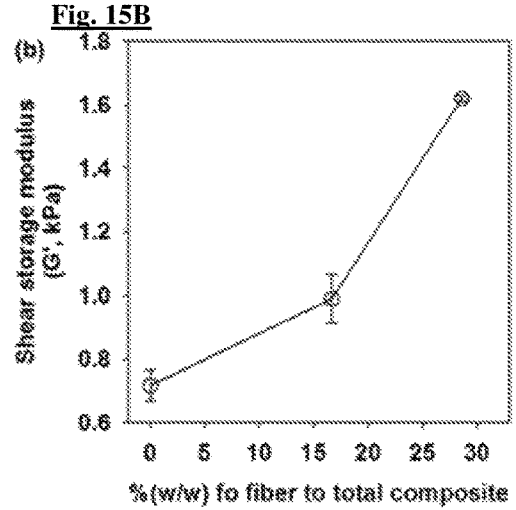
FIG. 15B depicts shear storage moduli of fiber-PEG hydrogel composites with various amounts of loaded fibers. *p<0.05 (n=3).

In this study, it was identified that it was possible to tune the mechanical properties of the fiber-hydrogel composite by various factors, including the total surface area of fibers, the density of the functional maleimide groups on the fiber surface, and the amount of fibers loaded into the hydrogel. Firstly, composites with smaller diameter of fibers showed a higher compressive and shear storage modulus than those of composites with bigger diameter of fibers (FIG. 7A and FIG. 8C). Similarly, in the literature, a single ultra-high molecular-weight polyethylene (UHMWPE) fiber (~25 µm), which was plasma activated using glutaraldehyde, showed approximately 2.36-fold increase of interfacial shear strength in a poly(vinyl alcohol) hydrogel compared to it of a UHMWPE fiber bundle of 60 [Acta Biomaterialia 2014, 10, 3581-3589]. Therefore, it is possible that decreasing the fiber diameter and thus increasing the fiber specific surface area may be an effective in improving the mechanical properties of the composite. However, each fiber group had a slightly different MAL surface density on the fibers (approximately 10-15 nmol/mg), so the effect of surface area of fibers alone cannot definitively be determined. Hence, secondly, composites were fabricated with the same diameter fibers, but with various MAL surface densities on the fibers (FIG. 8). The compression and shear storage moduli of composites were increased with increasing MAL surface density on the fibers. It was confirmed that a composite without the interfacial bonding showed only a slight enhancement of its compressive modulus (FIG. 7) by using fibers modified through the PAA step (carboxyl groups on fibers), but not the further MAL conjugation steps. The importance of the interfacial bonding was additionally confirmed by quenching the MAL groups on the fibers with cysteine prior to gelation. The cysteine conjugates to the maleimide group and prevents interfacial bonding between the fibers and hydrogel, which allows us to isolate just the effect of interfacial bonding, since the fibers were otherwise processed identically to the interfacial-bonding groups. Interestingly, the mechanical properties of the composites with the MAL-quenched fibers were dramatically diminished (FIG. 7A and FIG. 8B), with the MAL-quenched fiber group showing a lower compressive modulus than that of HA hydrogel-alone when the concentration of HA was 10 mg/ml (FIG. 7). It is possible that the MAL-quenched fibers weakened the overall composite by delaminating easily at the interface of the fibers and hydrogel, as is seen in previous studies [Acta Biomaterialia 2014, 10, 3581-3589]. Also, the fibers without functional groups may be acting as an alien substance that inhibits gelation compared to a pure hydrogel composed of one component or without any alien substance during gelation [JMC B 2015, DOI: 10.1039/C3TB21830A, Journal of Biomedical Materials Research Part A 2010, 95 (2), 564-573]. Furthermore, a significant correlation between shear storage modulus and the density of the interfacial bonding by composites with various MAL surface densities was verified (FIG. 8C). These studies provide strong evidence that the mechanical properties of hydrogel could be reinforced and tuned by the interfacial bonding. Thirdly, the shear storage modulus of the composites was enhanced with an increasing weight ratio of fibers to hydrogel (FIG. 9). Thereby, it was confirmed that the weight ratio was another variable that can be used to tune the mechanical properties of a fiber-hydrogel composite. However, here, it was confirmed that with increasing fiber loading, the shear storage modulus increases began to level off and even slightly decreased above 0.6 of the weight ratio. One possibility for this saturation effect may be that the density of interfacial bonding of a composite was diminished by how the excess fibers with MAL reacted with a large fraction of the thiol groups of HA, preventing them from reacting with the PEGDA for gelation. Considering that the highest shear storage modulus of the HA hydrogel was obtained with an equimolar amount of each functional group of HA-SH and PEGDA as well as the decreasing shear storage modulus with excess amounts of either HA-SH or DA (FIG. 14A), the excess MAL on the fibers with the increasing amount of fibers could disrupt the SH-to-DA bonding inside a composite.

Generally, implanted biomaterials have to withstand numerous internal and external stresses during regeneration of the tissue defect. Although the stress is not severe and continuous, stress resistance tests were performed under a repeating condition and a high frequency (10 Hz) to mimic such stresses (FIG. 10 and FIG. 8). Both the HA hydrogel and fiber-HA hydrogel composite withstood without any damage or reduction of their mechanical strength during repeating compressive strain. Noticeably, composites with the interfacial bonding retained their shear storage modulus at 10 Hz of frequency, whereas the shear storage modulus of the HA hydrogel and the composite without the interfacial bonding were diminished at 10 Hz. This trend indicates that the interfacial bonding with the dispersed fibers is crucial to the reinforcement of the composite's mechanical properties. In addition, the fiber-HA composites maintained their dimensions and their Young's moduli after being subjected to lyophilization and subsequent rehydration, while the HA-alone gel shrank substantially under the same process (FIG. 6C and FIG. 10). This shape, volume, and stiffness maintenance after dehydration and rehydration is an important feature for clinical translation of this technology, as having a lyophilized form of the composite would make it easier to sterilize and store the commercial product.

For soft tissue reconstruction, the ideal implanted scaffold would immediately fill the defect void, but would also serve as a substrate for the body's own cells to grow into the scaffold, proliferate and differentiate into the proper tissue phenotype, eventually replacing the artificial scaffold with normal, healthy tissue. Thus, it is critically important that relevant cells would be able to migrate within the hydrogel or composite scaffold To determine the potential for relevant cell types to migrate within the scaffolds, hASC spheroids were seeded inside HA hydrogels and fiber-HA hydrogel composites and evaluated their cell migration. The hASCs could not migrate inside the HA hydrogel-alone because the HA hydrogel was too soft to serve the traction forces for cell migration (FIG. 11A) [Biomaterials 2015, 42, 134-143]. Interestingly, although shear storage modulus of the composites was similar to that of the HA hydrogel, the hASCs were able to significantly migrate away from a spheroid inside the composites (FIG. 11). One hypothesis is that the fibers inside a composite may be providing adhesion sites to guide cell migration similarly to the fibril components of the native ECM of adipose tissue. It was previously demonstrated that aligned and random fibers could be a critical factor for cell adhesion, proliferation, differentiation, and migration in various cell types [Biomaterials 2005, 26, 2537-2547/2006, 27, 6043-6051/2009, 30, 556-564/2010, 31, 9031-9039, Acta Biomaterialia 2013, 9, 7727-7736]. Especially, it was observed that cells recognized fibers as a guide matrix, as their cytoskeletons aligned with and followed along the underlying fibers [Biomaterials 2006, 30, 6043-6051/2009,30, 556-564]. However, the diameter of the fibers inside the composites did not affect the migrating cells, as they migrated robustly in composites with either 1000-nm or 286-nm nanofibers (FIG. 19).

The porosity and cell migration effects seen in benchtop testing and in vitro cell culture translated into profound differences during in vivo testing of the composites. The hydrogels formulated to fat-mimicking 2 kPa stiffness without fibers had a porosity too low for cellular infiltration. The cellular response was to wall off the hydrogel with a thick layer of collagen, with the lack of infiltration or remodeling typical of a foreign body response. The nanofiber-hydrogel composite, however, had sufficient porosity to facilitate cellular ingrowth, vascularization, and cellular remodeling without the foreign body response. This offers the prospective of permanently filling the volumetric defect in the body with what will ultimately be the body's own tissue. The results were even more pronounced in the injectable formulation, which can form a tighter interface with the host tissue and showed signs of robust adipogenesis.

CONCLUSION

The dispersion of functionalized nanofibers within a hydrogel forms a composite structure with the combined strengths of the two components. The interfacial bonding between the nanofibers and the hydrogel components is critical to making a strong composite, while maintaining high porosity and pore size to facilitate tissue and cell ingrowth. The resulting composite properties can be easily tuned by varying the fiber diameter, fiber loading level, maleimide density level, and the loading levels of the hydrogel components. This allows for lower crosslinking and higher porosity at a targeted overall stiffness, increasing cellular infiltration and subsequent tissue remodeling. The fibers themselves may also directly improve cellular migration by providing adhesion sites similar to that seen in the native ECM. The resulting composite implant can be tuned to match the stiffness of native fat tissue, yet remain permeability for cellular infiltration and remodeling. This novel composite is strong enough to immediately fill a volumetric defect of any arbitrary shape. The composite implant then serves as a permissive scaffold for the body's own cells to infiltrate into the composite, form blood vessels, and differentiate into cells like adipocytes. The scaffold will be slowly degraded away during tissue remodeling, until the initial defect void has been replaced fully by normal, healthy tissue. The composite structure has great potential for reconstructive and aesthetic surgery potential.

EQUIVALENTS

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. An injectable scaffold complex comprising a polymeric fiber or fragments thereof having a mean diameter of from about 100 nm to about 8000 nm covalently linked to a hydrogel material,
    wherein the hydrogel material is capable of forming a network,
    wherein the polymeric fiber or fragments comprise functional groups and the surface density of the functional groups on the polymeric fiber or fragments is from about 10 nmole/mg of fibers to about 160 nmole/mg of the fiber or fragments,
    wherein the ratio of polymeric fiber or fragments to hydrogel material is from about 1:10 to about 10:1 on a component-mass basis or from about 1 to 50 mg/mL on a concentration basis,
    wherein the scaffold complex comprises a plurality of pores, and
    the polymeric fiber or fragments thereof comprise a mean length of less than 500 micrometers.

2. The scaffold complex of claim 1, wherein the scaffold complex is capable of being injected through a 21 gauge or smaller gauge needle.

3. The scaffold complex of claim 1, wherein the scaffold complex is capable of forming an elastic gel prior to, during, or following injection.

4. The scaffold complex of claim 1, wherein the scaffold complex is isotropically reinforced.

5. The scaffold complex of claim 1, wherein the scaffold can form a gel comprising an arbitrary volumetric geometry.

6. The scaffold complex of claim 1, wherein the polymeric fiber or fragments thereof are uniformly dispersed.

7. The scaffold complex of claim 1, wherein the hydrogel material is bonded to the outer surface of the polymeric fiber or fragments.

8. The scaffold complex of claim 1, further comprising a polymeric fiber or fragments thereof non-covalently linked to a hydrogel material,
    wherein the hydrogel material is capable of forming a network,
    wherein the non-covalent link comprises (i) electrostatic interactions and/or (ii) hydrogen-bonding.

9. The scaffold complex of claim 1, wherein the polymeric fiber or fragments thereof comprises an electrospun fiber.

10. The scaffold complex of claim 1, wherein the polymeric fiber or fragments thereof comprises a synthetic polymeric material comprising a poly(lactic-co-glycolic acid), poly(lactic acid), and/or a polycaprolactone, or a combination or derivatives thereof; or a biological polymeric material selected from the group consisting of a silk, collagen, elastin, hyaluronic acid, chitosan, a derivative thereof, and a combination thereof.

11. The scaffold complex of claim 1, wherein the hydrogel material comprises a poly(ethylene glycol), a collagen, a dextran, an elastin, an alginate, a hyaluronic acid, a poly(vinyl alcohol), a derivative thereof, or a combination thereof.

12. The scaffold complex of claim 1, wherein the hydrogel material comprises a processed tissue extracellular matrix, wherein the processed tissue extracellular matrix is derivable from an adipose tissue.

13. The scaffold complex of claim 1, wherein the polymeric fiber or fragments thereof comprise a synthetic polymeric material comprising a poly(lactic-co-glycolic acid), poly(lactic acid), a polycaprolactone, or a combination or derivative thereof,
    and wherein the hydrogel material comprises a poly(ethylene glycol), a collagen, a dextran, an elastin, an alginate, a hyaluronic acid, a poly(vinyl alcohol), a derivative thereof, or a combination thereof.

14. The scaffold complex of claim 1, wherein the plurality of pores are present on a surface of the scaffold complex and within the scaffold complex,
    wherein the pores are present at a concentration of at least about 50 pores per square centimeters of the surface,
    and wherein at least 80% of the pores have an average pore diameter of at least 5 micrometers.

15. A medical device for retaining tissue shape in a subject undergoing a surgical procedure, comprising the scaffold complex of claim 1 in an amount effective to provide for the retention of a tissue shape when administered to the subject.

16. An injectable scaffold complex comprising a polymeric fiber or fragments thereof having a mean diameter of from about 100 nm to about 8000 nm covalently linked to a hydrogel material,
- wherein the hydrogel material is capable of forming a network;
- the ratio of polymeric fiber to hydrogel material is from about 1:10 to about 10:1 on a component-mass basis or from about 1 to 50 mg/mL on a concentration basis;
- wherein the polymeric fiber or fragments comprise functional groups and the surface density of the functional groups on the polymeric fiber or fragments is from about 10 nmole/mg of fibers to about 160 nmole/mg of the fiber or fragments
- the hydrogel material is bonded to the outer surface of the polymeric fiber or fragments; and
- the polymeric fiber or fragments thereof comprises an electrospun fiber.

17. The scaffold complex of claim 1, wherein the scaffold complex further comprises a crosslinking agent, wherein the crosslinking agent comprises poly(ethylene glycol) diacrylate (PEGDA), thiolated poly(ethylene glycol) (PEGSH), or combination thereof.

18. The scaffold complex of claim 1 wherein the functional groups comprise maleimide groups.

* * * * *